US009535071B2

(12) United States Patent
Landi et al.

(10) Patent No.: US 9,535,071 B2
(45) Date of Patent: Jan. 3, 2017

(54) METHODS AND COMPOSITIONS FOR DIAGNOSIS OF INFLAMMATORY LIVER DISEASE

(71) Applicants: The Governors of the University of Alberta, Edmonton (CA); Medizinische Hochschule Hannover, Hannover (DE)

(72) Inventors: Abdolamir Landi, Edmonton (CA); Michael Houghton, Edmonton (CA); D. Lorne Tyrrell, Edmonton, CA (US); Tim Lankisch, Hannover (DE); Tobias Weismueller, Hannover (DE); Michael Manns, Isernhagen (DE)

(73) Assignees: The Governors of the University of Alberta, Edmonton (CA); Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 14/423,998

(22) PCT Filed: Sep. 6, 2013

(86) PCT No.: PCT/IB2013/002611
§ 371 (c)(1),
(2) Date: Feb. 25, 2015

(87) PCT Pub. No.: WO2014/037811
PCT Pub. Date: Mar. 13, 2014

(65) Prior Publication Data
US 2015/0219664 A1 Aug. 6, 2015

Related U.S. Application Data

(60) Provisional application No. 61/718,134, filed on Oct. 24, 2012, provisional application No. 61/698,412, filed on Sep. 7, 2012.

(51) Int. Cl.
*C40B 30/04* (2006.01)
*G01N 33/48* (2006.01)
(Continued)

(52) U.S. Cl.
CPC ...... *G01N 33/6827* (2013.01); *G01N 33/6893* (2013.01); *G06F 19/24* (2013.01);
(Continued)

(58) Field of Classification Search
CPC ................... G01N 33/6827; G01N 33/6893; G01N 33/48; G06F 19/24; G06F 19/3431; G06F 19/345; C40B 30/04
(Continued)

(56) References Cited

U.S. PATENT DOCUMENTS 6,329,159 B1   12/2001   Andrew et al.
6,673,908 B1   1/2004    Stanton, Jr.
(Continued)

FOREIGN PATENT DOCUMENTS

WO   2004/045525   6/2004

OTHER PUBLICATIONS

Angulo and Lindor (1999) "Primary biliary cirrhosis and primary sclerosing cholangitis", *Clinics in liver disease*; 3(3):529-570.
(Continued)

*Primary Examiner* — T. Victor Oh
(74) *Attorney, Agent, or Firm* — Carol L. Francis; Bozicevic, Field & Francis LLP

(57) ABSTRACT

The present disclosure provides methods and compositions that find use in facilitating a diagnosis of inflammatory liver disease in a subject. The methods and compositions generally involve detection of eotaxin-3 (E3) levels, either alone or with levels of eotaxin-1 (E1), and optionally, with levels of CCL22 and, further optionally, with levels of IL15. These levels can be used to facilitate a diagnosis of a liver disease
(Continued)

of at least one of autoimmune hepatitis (AIH), primary biliary cirrhosis (PBC), and primary sclerosing cholangitis (PSC), and/or to facilitate a differential diagnosis between AIH, PBC, and PSC. The methods and compositions of the present disclosure also find use in facilitating treatment decisions for a subject.

31 Claims, 18 Drawing Sheets

(51) Int. Cl.
G01N 33/68 (2006.01)
G06F 19/24 (2011.01)
G06F 19/00 (2011.01)
(52) U.S. Cl.
CPC ........ G06F 19/345 (2013.01); G06F 19/3431 (2013.01); G01N 2333/521 (2013.01); G01N 2333/523 (2013.01); G01N 2333/5443 (2013.01); G01N 2333/916 (2013.01); G01N 2800/085 (2013.01)
(58) Field of Classification Search
USPC .......................... 514/627, 894; 506/9; 702/19
See application file for complete search history.

(56) References Cited

U.S. PATENT DOCUMENTS

| | | |
|---|---|---|
| 6,689,570 B2 | 2/2004 | Andrew et al. |
| 6,884,574 B2 | 4/2005 | Andrew et al. |
| 6,905,827 B2 | 6/2005 | Wohlgemuth et al. |
| 6,936,248 B1 | 8/2005 | Andrew et al. |
| 6,946,134 B1 | 9/2005 | Rosen et al. |
| 6,946,546 B2 | 9/2005 | Vaughan et al. |
| 7,026,121 B1 | 4/2006 | Wohlgemuth et al. |
| 7,235,358 B2 | 6/2007 | Wohlgemuth et al. |
| 7,381,412 B2 | 6/2008 | Andrew et al. |
| 7,485,301 B2 | 2/2009 | Andrew et al. |
| 7,501,123 B2 | 3/2009 | Roschke et al. |
| 7,517,864 B2 | 4/2009 | Vargeese et al. |
| 7,691,839 B2 | 4/2010 | Glidden |
| 7,695,716 B2 | 4/2010 | Drachman et al. |
| 7,771,719 B1 | 8/2010 | Filvaroff et al. |
| 7,772,433 B2 | 8/2010 | Dalton et al. |
| 7,879,328 B2 | 2/2011 | Ruben et al. |
| 7,888,466 B2 | 2/2011 | Li |
| 8,003,689 B2 | 8/2011 | Veverka |
| 8,080,682 B2 | 12/2011 | Dalton et al. |
| 8,110,562 B2 | 2/2012 | Dalton et al. |
| 8,129,504 B2 | 3/2012 | Prior et al. |
| 8,147,837 B2 | 4/2012 | Bercovier et al. |
| 8,158,828 B2 | 4/2012 | Dalton et al. |
| 8,168,783 B2 | 5/2012 | Kokubo et al. |
| 8,188,034 B2 | 5/2012 | Glidden |
| 2002/0090673 A1 | 7/2002 | Rosen et al. |
| 2003/0068627 A1 | 4/2003 | Rosen et al. |
| 2003/0224426 A1 | 12/2003 | Li |
| 2004/0023334 A1 | 2/2004 | Prior |
| 2005/0053938 A1 | 3/2005 | Kohler |
| 2005/0255532 A1 | 11/2005 | Ruben et al. |
| 2006/0094056 A1 | 5/2006 | Chappell et al. |
| 2006/0121562 A1 | 6/2006 | Liou |
| 2006/0130158 A1 | 6/2006 | Turner et al. |
| 2007/0037164 A1 | 2/2007 | Stanton |
| 2007/0099819 A1 | 5/2007 | Glidden |
| 2007/0111203 A1 | 5/2007 | Cao et al. |
| 2007/0265296 A1 | 11/2007 | Dalton et al. |
| 2007/0281906 A1 | 12/2007 | Dalton et al. |
| 2008/0003230 A1 | 1/2008 | Adair |
| 2008/0057068 A1 | 3/2008 | Dalton et al. |
| 2008/0076828 A1 | 3/2008 | Dalton et al. |
| 2008/0076829 A1 | 3/2008 | Dalton et al. |
| 2008/0267960 A1 | 10/2008 | Drachman et al. |
| 2008/0318868 A1 | 12/2008 | Bercovier et al. |
| 2009/0030036 A1 | 1/2009 | Dalton et al. |
| 2009/0118503 A1 | 5/2009 | Sprott et al. |
| 2009/0156614 A1 | 6/2009 | Dalton et al. |
| 2009/0233275 A1 | 9/2009 | Rothenberg |
| 2009/0304693 A1 | 12/2009 | Ghayur et al. |
| 2009/0311253 A1 | 12/2009 | Ghayur et al. |
| 2009/0325167 A1 | 12/2009 | Chappell et al. |
| 2010/0004326 A1 | 1/2010 | Veverka |
| 2010/0040537 A1 | 2/2010 | Gu et al. |
| 2010/0074886 A1 | 3/2010 | Das et al. |
| 2010/0074900 A1 | 3/2010 | Ghayur et al. |
| 2010/0076178 A1 | 3/2010 | Ghayur et al. |
| 2010/0111953 A1 | 5/2010 | Ruben et al. |
| 2010/0129419 A1 | 5/2010 | Glidden |
| 2010/0197708 A1 | 8/2010 | Talley et al. |
| 2010/0215653 A1 | 8/2010 | Drachman et al. |
| 2010/0233079 A1 | 9/2010 | Jakob et al. |
| 2010/0260668 A1 | 10/2010 | Ghayur et al. |
| 2010/0267767 A1 | 10/2010 | Narayanan et al. |
| 2011/0008766 A1 | 1/2011 | Ghayur et al. |
| 2011/0034396 A1 | 2/2011 | Glidden |
| 2011/0038856 A1 | 2/2011 | Drachman et al. |
| 2011/0044980 A1 | 2/2011 | Ghayur et al. |
| 2011/0077221 A1 | 3/2011 | Dalton et al. |
| 2011/0091372 A1 | 4/2011 | Ghayur et al. |
| 2011/0091463 A1 | 4/2011 | Ghayur et al. |
| 2011/0091543 A1 | 4/2011 | Prior et al. |
| 2011/0117093 A1 | 5/2011 | Ruben et al. |
| 2011/0212094 A1 | 9/2011 | Ghayur et al. |
| 2011/0237664 A1 | 9/2011 | Dalton et al. |
| 2011/0263827 A1 | 10/2011 | Ghayur et al. |
| 2011/0287009 A1 | 11/2011 | Scheer et al. |
| 2011/0293610 A1 | 12/2011 | Ruben et al. |
| 2012/0009196 A1 | 1/2012 | Muerhoff et al. |
| 2012/0014957 A1 | 1/2012 | Ghayur et al. |
| 2012/0034160 A1 | 2/2012 | Ghayur et al. |
| 2012/0087858 A1 | 4/2012 | Ghayur et al. |
| 2012/0136052 A1 | 5/2012 | Dalton et al. |

OTHER PUBLICATIONS

Angulo et al. (1999) "Primary Sclerosing Cholangitis," *Hepatology*; 30(1):325-332.

Bartels et al. (1996) "Human dermal fibroblasts express eotaxin: molecular cloning, mRNA expression, and identification of eotaxin sequence variants," *Biochemical and biophysical research communications*, 225(3):1045-1051.

Bhattacharya, et al. (2007) "Increased expression of eotaxin-3 distinguishes between eosinophilic esophagitis and gastroesophageal reflux disease," *Human Pathology*; 38(12):1744-1753.

Blanchard et al. (2005) "Eotaxin-3/CCL26 gene expression in intestinal epithelial cells is up-regulated by interleukin-4 and interleukin-13 via the signal transducer and activator of transcription," *The International Journal of Biochemistry & Cell Biology*; 37(12):2559-2573.

Burak et al. (2003) "Is there a role for liver biopsy in primary sclerosing cholangitis?" *The American Journal of Gastroenterology*, 98(5):1155-1158.

Czaja et al. (2010) "Adances in the Diagnosis, Pathogenesis, and Management of Autoimmune Hepatitis," *Gastroenterology*; 139(1):58-72

Daugherty et al. (1996) "Cloning, expression, and characterization of the human eosinophil eotaxin receptor," The Journal Of Experimental Medicine; 183(5):2349-2354.

Donnan et al. (2009) "Development of a decision support tool for primary care management of patients with abnormal liver function tests without clinically apparent liver disease: a record-linkage population cohort study and decision analysis (ALFIE)," *Health Technology Assessment*, 13(25):iii-iv, ix-xi, 1-134.

Dulkys et al. (2001) "Detection of mRNA for eotaxin-2 and eotaxin-3 in human dermal fibroblasts and their distinct activation profile on human eosinophils," *The Journal of Investigative Dermatology*; 116(4):498-505.

(56) References Cited

OTHER PUBLICATIONS

Elsner and Kapp (2001) "The chemokine network in eosinophil activation," *Allergy and Asthma Proceedings : The Official Journal of Regional and State Allergy Societies*; 22(3):139-148.

Elsner, Escher, and Forssmann (2004) "Chemokine receptor antagonists: a novel therapeutic approach in allergic diseases," *Allergy*, 59(12):1243-1258.

Elsner, et al. (1998) "Eotaxin-2 activates chemotaxis-related events and release of reactive oxygen species via pertussis toxin-sensitive G protein in human eosinophils," *European journal of immunology*28(7):2152-2158.

Elsner, et al. (2000) "Differential activation of CC chemokine receptors by AOP-RANTES," *The Journal of Biological Chemistry*; 275(11):7787-7794.

Fichorova, et al. (2008) "Biological and technical variables affecting immunoassay recovery of cytokines from human serum and simulated vaginal fluid: a multicenter study," *Analytical chemistry*: 80(12):4741-4751.

Gerber, et al. (1997) "Funtional expression of the eotaxin receptor CCR in T lymphocytes co-localizing with eosinophils," *Current biology*; 7(11):836-843.

Halford et al. (1969) "A substrate-induced conformation change in the reaction of alkaline phosphatase from *Escherichia coli*," *J. Biol. Chem.*; 114(243):3552-3559.

Hanley and McNeil (1982) "The Meaning and Use of the Area under a Receiver Operating Characteristic (ROC) Curve," *Radiology*143:29-36.

Hegde, Nagarkatti, and Nagarkatti (2011) "Role of myeloid-derived suppressor cells in amelioration of experimental autoimmune hepatitis following activation of TRPV1 receptors by cannabidiol," *PLoS One*6(4):e18281.

Jaruga et al. (2003) "Crucial role of IL-4/STAT6 in T cell-mediated hepatitis Up- regulating eotaxins and IL-5 and recruiting leukocytes," *Journal of Immunology*; 171:3233-3244.

Kagami et al. (2012) "High Levels of CCL26 in Blister Fluid and Sera of Patients with Bullous Pemphigoid," *Journal of Investigative Dermatology*; 132(1):249-251.

Kagami, et al. (2003) "Significant elevation of serum levels of eotaxin-3/CCL26, but not of eotaxin-2/CCL24, in patients with atopic dermatitis: serum eotaxin-3/CCL26 levels reflect the disease activity of atopic dermatits," *Clinical and experimental immunology*; 134(2):309-313.

Kaplan et al. (2005) "Primary Biliary Cirrhosis," *New Engl. J. Med.*; 353(12):1261-1273.

Kitaura, et al. (1996) "Molecular cloning of human eotaxin, an eosinophil-selective CC chemokine, and identification of a specific eosinophil eotaxin receptor, CC chemokine receptor 3," *The Journal of biological chemistry*; 271(13):7725-7730.

Kitaura, et al. (1999) "Molecular cloning of a novel human CC chemokine (Eotaxin-3) that is a functional ligand of CC chemokine receptor 3," *The Journal of biological chemistry*; 274(39):27975-27980.

Kohan, et al. (2010) "Eotaxin-2/CCL24 and eotaxin-3CCL26 exert differential profibrogenic effects on human lung fibroblasts," *Annals of allergy, asthma & immunology : official publication of the American College of Allergy, Asthma, & Immunology*; 104(1):66-72.

Komiya, et al. (2003) "Concerted expression of eotaxin-1, eotaxin-2, eotaxin-3, in human bronchial epithelial cells," *Cellular immunology*; 225(2):91-100.

Li, et al. (1997) "Eotaxin protein and gene expression in guinea-pig lungs: constitutive expression and upregulation after allergen challenge," *The European respiratory journal : official journal of the European Society for Clinical Respiratory Physiology*: 10(9):1946-1954.

Lilly, et al. (2001) "Eotaxin expression after segmental allergen challenge in subjects with atopic asthma," *American journal of respiratory and critical care medicine*; 163(7):1669-75.

Lohse, et al. (2011) "Autoimmune Hepatitis," *Journal of Hepatology*; 55(1):171-182.

Manns et al. (2010) "Diagnosis and management of autoimmune hepatitis," *Hepatology*: 51(6):2193-2213.

Manousou, et al. (2010) "Increase expression of chemokine receptor CCR3 and its ligands in ulcerative colitis: the role of colonic epithelial cells in in vitro studies," *Clinical and experimental immunology*; 162(2):337-347.

Matsukura, et al. (2001) "Interleukin-13 upregulates eotaxin expression in airway epithelial cells by a STAT6-dependent mechanism," *American journal of respiratory cell and molecular biology*24(6):755-761.

Menzies-Gow, et al. (2002) "Eotaxin (CCL11) and eotaxin-2 (CCL24) induce recruitment of eosinophils, basophils, neutrophils, and macrophages as well as features of early- and late-phase allergic reactions following cutaneous injection in human atopic and nonatopic volunteers," *Journal of immunology*; 169(5):2712-2718.

Nakayama, et al. (2010) "Eotaxin-3/CC chemokine ligand 26 is a functional ligand for CX3CR1," *Journal of immunology*; 185(11):6472-6479.

Ochi, et al. (1999) "T helper cell type 2 cytokine-mediated comitogenic responses and CCR3 expression during differentiation of human mast cells in vitro," *The Journal of experimental medicine*; 190(2):267-280.

Ogilive, et al. (2003) "Eotaxin-3 is a natural antagonist for CCR2 and exerts a repulsive effect of human monocytes," *Blood*; 102(3):789-794.

Petkovic, et al. (2004) "Eotaxin-3/CCL26 is a natural antagonist for CC chemokine receptors 1 and 5. A human chemokine with a regulatory role," *The Journal of biological chemistry*; 279(22):23357-23363.

Pham et al. (2001) "Eotaxin expression and eosinophil infiltrate in the liver of patients with drug-induced liver disease," *Journal of Hepatology*; 34:537-547.

Polzer et al. (2008) "Eotaxin-3 is involved in Churg-Strauss syndrome—a serum marker closely correlating with disease activity," *Rheumatology*; 47(6):804-808.

Ponath, et al. (1996) "Cloning of the human eosinophil chemoattractant, eotaxin. Expression, receptor binding, and functional properties suggest a mechanism for the selective recruitment of eosinophils," *The Journal of clinical investigation*; 97(3):604-612.

Ponsioen et al. (2002) "Natural history of primary sclerosing cholangitis and prognostic value of cholangiography in a Dutch population," *Gut*, 51(4)562-566.

Pope, et al. (2001) "IL-13 induces eosinophil recruitment into the lung by an IL-5- and eotaxin-dependent mechanism," *The Journal of allergy and clinical immunology*; 108(4):594-601.

Rubbert, et al. (1998) "Dendritic cells express multiple chemokine receptors used as coreceptors for HIV entry," *Journal of immunology*; 160(8):3933-3941.

Sallusto, et al. (1999) "Distinct patterns and kinetics of chemokine production regulate dendritic cell function," *Eur J Immunol*; 29(5):1617-1625.

Schrumpf, et al. (1982) "Sclerosing cholangitis in ulcerative colitis. A follow-up study." *Scan. J. Gastroenterol.*; 17(1)33-39.

Shinkai, et al. (1999) "A novel human CC chemokine, eotaxin-3, which is expressed in IL-4-stimulated vascular endothelial cells, exhibits potent activity toward eosinophils," *Journal of immunology*; 163(3):1602-1610.

Tacke et al. (2007) "Up-regulated eotaxin plasma levels in chronic liver disease patients indicate hepatic inflammation advanced fibrosis and adverse clinical course," *Hepatology*; 22:1256-1264.

Terada, et al. (2001) "The kinetics of allergen-induced eotaxin level in nasal lavage fluid: its key role in eosinophil recruitment in nasal mucosa," *American journal of respiratory and critical care medicine*, 164(4):575-579.

Tischendorf et al. (2007) "Characterization, Outcome, and Prognosis in 273 Patients with Primary Sclerosing Cholangitis: A Single Center Study," *Am J. Gastroenterol.*; 102(1)107-114.

Tsuneyama, et al. (2001) "Monocyte chemotactic protein-1, -2, and -3 are distinctively expressed in portal tracts and granulomata in primary biliary cirrhosis: implications for pathogenesis," *The Journal of pathology*; 193(1):102-109.

(56) References Cited

OTHER PUBLICATIONS

Tsuneyama, et al. (2001) "Scavenger cells with gram-positive bacterial lipoteichic acid infiltrate around the damaged interlobular bile ducts of primary biliary cirrhosis," *Journal of hepatology*; 35(2):156-163.

Uguccioni, et al. (1997) "High expression of the chemokine receptor CCR3 in human blood basophils. Role in activation by eotaxin, MCP-4, and other chemokines," *The Journal of clinical investigation*; 100(5):1137-1143.

Vasudevan, et al. (2006) "Eotaxin and obesity," *The Journal of clinical endocrinology and metabolism*; 91(1):256-261.

Weng, et al. (1998) "Binding and functional properties of recombinant and endogenous CXCR3 chemokine receptors," *The Journal of biological chemistry* 273(29):18288-18291.

Whitehead et al. (1999) "A prospective study of the causes of notably raised aspartate aminotransferase of liver origin," *Gut*, 45(1):129-133.

Ying, et al. (1999) "C—C chemokines in allergen-induced late-phase cutaneous responses in atopic subjects: association of eotaxin with early 6-hour eosinophils, and eotaxin-2 and monocyte chemoattractant protein-4 with the later 24-hour tissue eosinophilia, and relationship to basophils and other C—C chemokines (monocyte chemoattractant protein-3 and RANTES)," *Journal of immunology*, 163(7):3976-3984.

Ying, et al. (1999) "Eosinophil chemotactic (eotaxin, eotaxin-2, RANTES, monocyte chemoattractant protein-3 (MCP-3), and MCP-4), and C—C chemokine receptor 3 expression in biopsies from atopic and nonatopic (Intrinsic) asthmatics," *Journal of immunology*; 163(11):6321-6329.

Zwerina, et al. (2011) "Eotaxin-3 in Churg-Strauss syndrome: a clinical and immunogenetic study," *Rheumatology (Oxford)*; 50(10):1823-1827.

"CCL11 polyclonal antibody", Aug. 5, 2011, URL: http://www.abnova.com/products/products_detail.asp?catalog_id=PAB11429.

"eotaxin-3 Antibody (N-10): sc-21620", Sep. 26, 2008, URL: http://datasheets.scbt.com/sc-21620.pdf.

"eotaxin-3 (4i22): sc-71055", Oct. 3, 2008, URL:http://datasheets.scbt.com/sc-71055.pdf.

"MDC (C-18): sc-12285", Jul. 26, 2012, URL: http://datasheets.scbt.com/sc-12285.pdf.

"MDC (R-19): sc-74223", May 24, 2012, URL: http://datasheets.scbt.com/sc-74223.pdf.

Genbank: BAA36704.1, eotaxin-3 [*Homo sapiens*], accession AB016542.1, 1999.

GenBank: CAG33702.1 CCL11 [*Homo sapiens*], accession CR457421.1, 2008.

GenBank: EAW82918.1, chemokine (C—C motif) ligand 22 [*Homo sapiens*], accession CH471092.1, 2006.

NCBI Reference Sequence: NP_000576.1, interleukin-15 isoform 1 preprotein [*Homo sapiens*], accession NM_000585.4, 2012.

NCBI Reference Sequence: NP_002977.1, eotaxin precursor [*Homo sapiens*], accession NM_002986.2, 2012.

NCBI Reference Sequence: NP_002981.2, C—C motif chemokine 22 precursoe [*Homo sapiens*], accession NM002990.4, 2012.

NCBI Reference Sequence: NP_751915.1, interleukin-15 isoform 2 preproprotein [*Homo sapiens*], accession NM_172175.2, 2012.

OMIM Entry—600554, Interleukin 15; IL15, downloaded from http://omin.org/entry/600554?search=il-15&highlight=il15il on Jun. 5, 2012.

OMIM Entry—601156, Chemokine, CC MOTIF, LIGAND 11; CCL11, downladed from http://omim.org/entry/601156?search=eotaxin-1&highlight=eotaxin1 on Jun. 5, 2012.

OMIM Entry—602957, Chemokine, CC MOTIF, LIGAND 22; CCL22, downloaded from http://omim.org/entry/602957 on Jun. 5, 2012.

OMIM Entry—604697, Chemokine, CC MOTIF, LIGAND 26; CCL26, downloaded from http://omim.org/entry/604697 on Jun. 5, 2012.

UniProtKB/Swiss-Prot: O00626.2, RecName: Full=C—C motif chemokine 22; AltName: Full=CC chemokine STCP-1; AltName:Full=MDC(1-69); AltName: Full=Macrophage-derived chemokine; AltName: Full=Smallinducible cytokine A22; AltName: Full=Stimulated T-cell chemotactic protein 1; Contains: RecName: . . . , ACCESSION O00626, 2012.

UniProtKB/Swiss-Prot: P40933.1, RecName: Full=Interleukin-15; Short=IL-15; Flags: Precursor, ACCESSION P40933, 2012.

Landi, Abdolamir, et al., (2014) "Differential Serum Levels of Eosinophilic Eotaxins in Primary Sclerosing Cholangitis, Primary Biliary Cirrhosis, and Autoimmune Hepatitis", Journal of Interferon and Cytokine Research., 34(3):204-214.

Landi, Abdolamir, et al., (2012) "Novel serological 1-16 biomarkers to aid diagnosis of primary sclerosing cholangitis, primary biliary cirrhosis and autoimmune hepatitis", Hepatology, John Wiley & Sons, Inc, USA, 56 (6):1529.

Zu-Yau Lin et al, (2012) "Cancer-associated fibroblasts up-regulate CCL2, CCL26, IL6 and LOXL2 genes related to promotion of cancer progression in hepatocellular carcinoma cells", Biomedicine & Pharmacotherapy, 66 (7):525-529.

J. Zwerina et al, (2011) "Eotaxin-3 in Churg-Strauss syndrome: a clinical and immunogenetic study" , Rheumatology, 50(10):1823-1827.

Dimitrios-P Bogdanos (2008) "Autoimmune liver serology: Current diagnostic and clinical challenges", World Journal of Gastroenterology, 14(21):3374-3387.

Feng, Zhihua, et al., (2004) "Chemokines and Chronic Hepatitis C", World Chin J Digestol, 12(11):2664-2667.

FIG. 3

| | | E3>28 | | E3>25 | | PSC Group | Condition | Eotaxin-3 > 28 | | E3 > 28 + E1/E3>15 + MDC >2800 | | Eotaxin-3 > 25 | | E3 > 25 + E1/E3>15 + MDC >2800 | | E3 > 25 + E1/E3<15 + MDC >1870+ IL-15>2.4 | |
|---|---|---|---|---|---|---|---|---|---|---|---|---|---|---|---|---|---|
| PSC, PBC, or AIH | Ctrl/HCV | 5 / 104 | 5% | 7 / 104 | 7% | | Control | 1/50 | 2% | 1/50 | 2% | 2/50 | 4% | 2/50 | 4% | 0/50 | 0% |
| | | | | | | | HCV | 4/54 | 7% | 1/54 | 2% | 5/54 | 9% | 3/54 | 6% | 0/54 | 0% |
| | PSC | 145 | 85% | 152 | 89% | PSC +/- IBD +/- AIH | 63/80 | 79% | 48/80 | 60% | 69/80 | 86% | 52/80 | 65% | 1/80 | 1% |
| | | | | | | | PSC alone | 16/20 | 80% | 13/20 | 65% | 18/20 | 90% | 15/20 | 75% | 0/20 | 0% |
| | | | | | | | PSC +/- IBD (no AIH) | 46/58 | 79% | 39/58 | 67% | 49/58 | 84% | 42/58 | 72% | 0/58 | 0% |
| | | | | | | | PSC+AIH +/- IBD | 17/22 | 77% | 9/22 | 41% | 20/22 | 91% | 10/22 | 45% | 1/22 | 5% |
| | | | | | | | PSC+AIH (no IBD) | 10/13 | 77% | 5/13 | 38% | 12/13 | 92% | 5/13 | 38% | 0/13 | 0% |
| | PBC | 170 | | 170 | | PBC | PBC | 42/50 | 84% | 3/50 | 6% | 43/50 | 86% | 3/50 | 6% | 5/50 | 10% |
| | AIH | | | | | AIH | AIH | 40/40 | 100% | 3/40 | 8% | 40/40 | 100% | 3/40 | 8% | 24/40 | 60% |

FIG. 4

| | Condition | E3 > 23 + E1/E3>10 + MDC > 2800 | | E3 > 23 + E1/E3>15 + MDC > 2800 | | E3 > 23 + E1/E3>20 + MDC > 2800 | | E3 > 25 + E1/E3>10 + MDC > 2800 | |
|---|---|---|---|---|---|---|---|---|---|
| Ctrl / HCV | Control | 3 | 6% | 3 | 6% | 3 | 6% | 2 | 4% |
| | | 50 | | 50 | | 50 | | 50 | |
| | HCV | 3 | 6% | 3 | 6% | 2 | 4% | 3 | 6% |
| | | 54 | | 54 | | 54 | | 54 | |
| PSC Group | PSC +/- IBD +/- AIH | 56 | 70% | 55 | 69% | 46 | 58% | 53 | 66% |
| | | 80 | | 80 | | 80 | | 80 | |
| | PSC alone | 16 | 80% | 16 | 80% | 13 | 65% | 15 | 75% |
| | | 20 | | 20 | | 20 | | 20 | |
| | PSC +/- IBD (no AIH) | 45 | 78% | 44 | 76% | 37 | 64% | 43 | 74% |
| | | 58 | | 58 | | 58 | | 58 | |
| | PSC+AIH +/- IBD | 11 | 50% | 11 | 50% | 9 | 41% | 10 | 45% |
| | | 22 | | 22 | | 22 | | 22 | |
| | PSC+AIH (no IBD) | 3 | 23% | 3 | 23% | 4 | 31% | 5 | 38% |
| | | 13 | | 13 | | 13 | | 13 | |
| PBC | PBC | 5 | 10% | 5 | 10% | 4 | 8% | 3 | 6% |
| | | 50 | | 50 | | 50 | | 50 | |
| AIH | AIH | 7 | 18% | 3 | 8% | 0 | 0% | 7 | 18% |
| | | 40 | | 40 | | 40 | | 40 | |

FIG. 5

| | Condition | E3 > 25 + E1/E3>15 + MDC >2800 | | | E3 > 25 + E1/E3>20 + MDC >2800 | | | E3 > 28 + E1/E3>10 + MDC >2800 | | | E3 > 28 + E1/E3>15 + MDC >2800 | | | E3 > 28 + E1/E3>20 + MDC >2800 | | |
|---|---|---|---|---|---|---|---|---|---|---|---|---|---|---|---|---|
| Ctrl./HCV | Control | 2 | 50 | 4% | 2 | 50 | 4% | 1 | 50 | 2% | 1 | 50 | 2% | 1 | 50 | 2% |
| | HCV | 3 | 54 | 6% | 2 | 54 | 4% | 2 | 54 | 4% | 2 | 54 | 4% | 1 | 54 | 2% |
| PSC Group | PSC +/- IBD +/- AIH | 52 | 80 | 65% | 44 | 80 | 55% | 49 | 80 | 61% | 48 | 80 | 60% | 39 | 80 | 49% |
| | PSC alone | 15 | 20 | 75% | 12 | 20 | 60% | 13 | 20 | 65% | 13 | 20 | 65% | 10 | 20 | 50% |
| | PSC +/- IBD (no AIH) | 42 | 58 | 72% | 35 | 58 | 60% | 40 | 58 | 69% | 39 | 58 | 67% | 32 | 58 | 55% |
| | PSC+AIH +/- IBD | 10 | 22 | 45% | 8 | 22 | 36% | 8 | 22 | 36% | 8 | 22 | 36% | 7 | 22 | 32% |
| | PSC+AIH (no IBD) | 5 | 13 | 38% | 4 | 13 | 31% | 5 | 13 | 38% | 5 | 13 | 38% | 4 | 13 | 31% |
| PBC | PBC | 3 | 50 | 6% | 2 | 50 | 4% | 3 | 50 | 6% | 3 | 50 | 6% | 2 | 50 | 4% |
| AIH | AIH | 3 | 40 | 8% | 0 | 40 | 0% | 7 | 40 | 18% | 3 | 40 | 8% | 0 | 40 | 0% |

FIG. 5 (Cont.)

| | Condition | E3 > 23 + E1/E3>10 + MDC >2800 | | | E3 > 23 + E1/E3>10 + MDC >3000 | | | E3 > 23 + E1/E3>15 + MDC >2800 | | | E3 > 23 + E1/E3>15 + MDC >3000 | | | E3 > 25 + E1/E3>10 + MDC >2800 | | |
|---|---|---|---|---|---|---|---|---|---|---|---|---|---|---|---|---|
| Ctrl / HCV | Control | 3 | 50 | 6% | 3 | 50 | 6% | 3 | 50 | 6% | 3 | 50 | 6% | 2 | 50 | 4% |
| | HCV | 3 | 54 | 6% | 3 | 54 | 6% | 3 | 54 | 6% | 3 | 54 | 6% | 3 | 54 | 6% |
| PSC Group | PSC +/- IBD +/- AIH | 56 | 80 | 70% | 51 | 80 | 64% | 55 | 80 | 69% | 50 | 80 | 63% | 53 | 80 | 66% |
| | PSC alone | 16 | 20 | 80% | 15 | 20 | 75% | 16 | 20 | 80% | 15 | 20 | 75% | 15 | 20 | 75% |
| | PSC +/- IBD (no AIH) | 45 | 58 | 78% | 40 | 58 | 69% | 44 | 58 | 76% | 39 | 58 | 67% | 43 | 58 | 74% |
| | PSC+AIH +/- IBD | 11 | 22 | 50% | 11 | 22 | 50% | 11 | 22 | 50% | 11 | 22 | 50% | 10 | 22 | 45% |
| | PSC+AIH (no IBD) | 3 | 13 | 23% | 3 | 13 | 23% | 3 | 13 | 23% | 5 | 13 | 38% | 5 | 13 | 38% |
| PBC | PBC | 5 | 50 | 10% | 5 | 50 | 10% | 5 | 50 | 10% | 5 | 50 | 10% | 3 | 50 | 6% |
| AIH | AIH | 7 | 40 | 18% | 7 | 40 | 18% | 3 | 40 | 8% | 3 | 40 | 8% | 7 | 40 | 18% |

FIG. 6

| | Condition | E3 > 25 + E1/E3 >10 + MDC >3000 | | E3 > 25 + E1/E3 >15 + MDC >2800 | | E3 > 25 + E1/E3 >15 + MDC >3000 | | E3 > 28 + E1/E3 >15 + MDC >2800 | | E3 > 28 + E1/E3 >15 + MDC >3000 | |
|---|---|---|---|---|---|---|---|---|---|---|---|
| Ctrl / HCV | Control | 2/50 | 4% | 2/50 | 4% | 2/50 | 4% | 2/50 | 4% | 1/50 | 2% |
| | HCV | 3/54 | 6% | 3/54 | 6% | 3/54 | 6% | 2/54 | 4% | 2/54 | 4% |
| PSC Group | PSC +/- IBD +/- AIH | 0/80 | 0% | 52/80 | 65% | 48/80 | 60% | 48/80 | 60% | 44/80 | 55% |
| | PSC alone | 15/20 | 75% | 15/20 | 75% | 15/20 | 75% | 13/20 | 65% | 13/20 | 65% |
| | PSC +/- IBD (no AIH) | 39/58 | 67% | 42/58 | 72% | 38/58 | 66% | 39/58 | 67% | 35/58 | 60% |
| | PSC+AIH +/- IBD | 10/22 | 45% | 10/22 | 45% | 10/22 | 45% | 9/22 | 41% | 9/22 | 41% |
| | PSC+AIH (no IBD) | 5/13 | 38% | 5/13 | 38% | 5/13 | 38% | 5/13 | 38% | 3/13 | 23% |
| PBC | PBC | 3/50 | 6% | 3/50 | 6% | 3/50 | 6% | 3/50 | 6% | 3/50 | 6% |
| AIH | AIH | 7/40 | 18% | 3/40 | 8% | 3/40 | 8% | 3/40 | 8% | 3/40 | 8% |

FIG. 6 (Cont.)

| Condition | | E3 > 25 + (E3/E1)*100<7 + MDC >2800 | | E3 > 25 + (E3/E1)*100<6 + MDC >2800 | |
|---|---|---|---|---|---|
| Ctrl./HCV | Control | 2/50 | 4% | 2/50 | 4% |
| | HCV | 3/54 | 6% | 2/54 | 4% |
| PSC Group | PSC +/- IBD +/- AIH | 52/80 | 65% | 50/80 | 63% |
| | PSC alone | 15/20 | 75% | 14/20 | 70% |
| | PSC +/- IBD (no AIH) | 42/58 | 72% | 41/58 | 71% |
| | PSC+AIH +/- IBD | 10/22 | 45% | 9/22 | 41% |
| | PSC+AIH (no IBD) | 5/13 | 38% | 4/13 | 31% |
| PBC | PBC | 3/50 | 6% | 3/50 | 6% |
| AIH | AIH | 3/40 | 8% | 3/40 | 8% |

FIG. 7

| Condition | | E3 > 25 + E1/E3<15 + MDC >1870+IL-15>2.4 | | E3 > 28 + E1/E3<20 + MDC >1870+IL-15>2.4 | | E3 > 28 + E1/E3<20 + MDC >1870+IL-15>2.5 | |
|---|---|---|---|---|---|---|---|
| Ctrl./HCV | Control | 0 / 50 | 0% | 0 / 50 | 0% | 0 / 50 | 0% |
| | HCV | 0 / 54 | 0% | 1 / 54 | 2% | 1 / 54 | 2% |
| PSC Group | PSC +/- IBD +/- AIH | 1 / 80 | 1% | 6 / 80 | 8% | 6 / 80 | 8% |
| | PSC alone | 0 / 20 | 0% | 2 / 20 | 10% | 2 / 20 | 10% |
| | PSC +/- IBD (no AIH) | 0 / 58 | 0% | 3 / 58 | 5% | 3 / 58 | 5% |
| | PSC+AIH +/- IBD | 1 / 22 | 5% | 3 / 22 | 14% | 3 / 22 | 14% |
| | PSC+AIH (no IBD) | 0 / 13 | 0% | 2 / 13 | 15% | 2 / 13 | 15% |
| PBC | PBC | 5 / 50 | 10% | 5 / 50 | 10% | 5 / 50 | 10% |
| AIH | AIH | 24 / 40 | 60% | 26 / 40 | 65% | 25 / 40 | 63% |

FIG. 8

| # | 1 | 2 | 3 | 4 | 5 | 6 | 7 | 8 | 9 |
|---|---|---|---|---|---|---|---|---|---|
| Row # | Diagnosis | Biomarker/s | Sensitivity (%) | Specificity (%) | PPV (%) | NPV (%) | PLR (1-∞) | Probability (%) | NLR (0-1) | Probability (%) |
| 1 | PSC | E3>28 | 79 | 98 | 98 | 80 | 40 | 98 | 0.21 | 17 |
| 2 | PBC | E3>28 | 84 | 98 | 98 | 86 | 42 | 98 | 0.16 | 14 |
| 3 | AIH | E3>28 | 100 | 98 | 98 | 100 | 50 | 98 | 0 | 0 |
| 4 | PSC-1 | E3>28 + E1/E3>15 + MDC>2800 | 67 | 98 | 98 | 72 | 34 | 97 | 0.33 | 25 |
| 5 | PSC-2 | E3>25 + E1/E3>15 + MDC>2800 | 72 | 96 | 95 | 75 | 18 | 95 | 0.29 | 22 |
| 6 | AIH | E3>25 + E1/E3<15 + MDC>1870 + IL-15>2.4 | 60 | 100 | 100 | 76 | ∞ | 100 | 0.4 | 29 |

FIG. 14

PSC Diagnostic Flow Chart

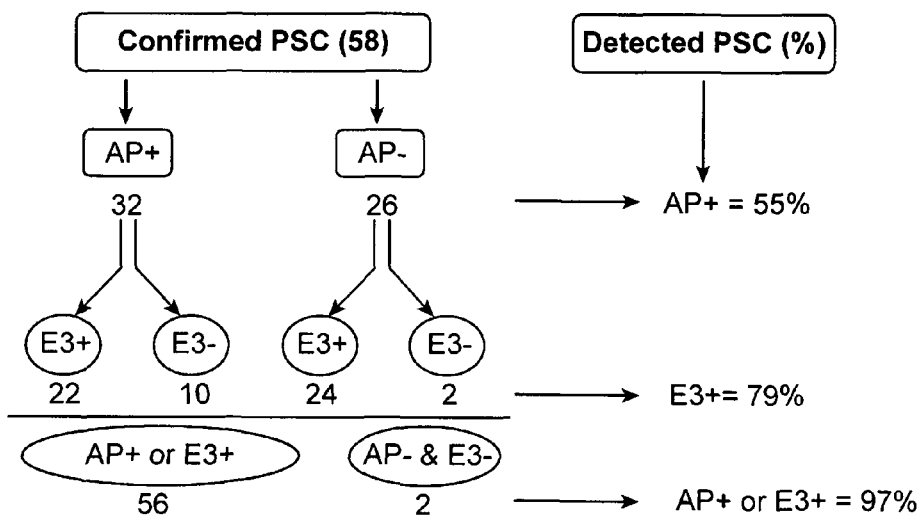

| | E3 = Eotaxin-3 | AP = Alkaline Phosphatase | | | |
|---|---|---|---|---|---|
| | E3+ = E3>28 pg/ml | AP+ = AP>129(M) & AP>104(W) U/l | | | |
| | | | | | |
| | Eotaxin-3 | AP-1 | AP-2 | AP-3 | AP-4 |
| # of individuals tested positive | 46 | 45 | 30 | 23 | 26 |
| Total | 58 | 58 | 42 | 38 | 37 |
| % Positivity | 79% | 78% | 71% | 61% | 70% |
| | | | | | |
| % Positivity (average of 4 time-points) | | 70% | | | |
| % Positivity (at least once) | | 88% | | | |
| % Positivity (at all time-points) | | 55% | | | |
| | | | | | |
| | | AP+ or E3+ to Diagnose PSC | | | |
| | | Detection rate if: AP+ or E+ | | | |
| % Positivity if AP+ (average of 4 time-points) or E3+ | | 97-98% | | | |
| % Positivity if AP+ (at least once) or E3+ | | 98% | | | |
| % Positivity if AP+ (at all 4 time-points) or E3+ | | 97% | | | |

FIG. 15

METHODS AND COMPOSITIONS FOR DIAGNOSIS OF INFLAMMATORY LIVER DISEASE

CROSS-REFERENCE

This application claims the benefit of U.S. Provisional Patent Application No. 61/698,412, filed Sep. 7, 2012, and U.S. Provisional Patent Application No. 61/718,134, filed Oct. 24, 2012, which applications are incorporated herein by reference in their entireties.

INTRODUCTION

Autoimmune hepatitis (AIH), primary biliary cirrhosis (PBC), and primary sclerosing cholangitis (PSC) are distinct chronic inflammatory liver diseases. The causes of these diseases are unknown. They are generally seen as autoimmune phenomena although an infectious etiology is possible for at least some of them. The onset of all three diseases is presented with non-specific symptoms for liver diseases such as fatigue, abdominal pain, nausea, and/or pruritus along with fluctuating levels of liver enzymes that may confirm the presence of a liver disorder only at later stages of the disease with fibrosis and cirrhosis. At this stage, symptoms and signs that are associated with portal hypertension consequences would also be reported.

The pathology of AIH starts with damage to hepatocytes resulting in interface hepatitis and piecemeal necrosis along with infiltration of leukocytes eventually followed by fibrosis and cirrhosis. In PBC and PSC, the inflammation usually starts around or close to the biliary system resulting in cholestatic disease leading to fibrosis and cirrhosis.

With respect to the diagnosis, various autoantibodies are considered as biomarkers for AIH. This mainly includes anti-nuclear antibodies (ANA), anti-smooth muscle antibodies (SMA), and antibodies to liver/kidney microsome type 1 (anti-LKM1), although other antibodies such as antibodies to soluble liver/pancreas antigen (anti-SLA/LP), perinuclear anti-neutrophil cytoplasmic antibodies (pANCA), antibodies to liver-specific cytosol antigen type 1 (anti-LC1), and anti-actin may be detected as well (Manns et al., Hepatology, 2010. 51(6): p. 2193-213; Czaja et al. Gastroenterology, 2010. 139(1): p. 58-72 e4). Since these autoantibodies are not specific for AIH and may be detected in patients with PBC, PSC, viral hepatitis, drug-induced hepatitis, and alcoholic hepatitis, the International Autoimmune Hepatitis Group has suggested a diagnostic algorithm for diagnosis of AIH. A simplified report of this algorithm (Lohse et al. Journal of Hepatology, 2011. 55(1): p. 171-82) indicates definite, probable, or lack of AIH, based on four parameters including the levels of different autoantibodies, the level of IgG, liver histology, and absence of a known viral infection.

In PBC, which is described as a chronic non-suppurative destructive granulomatous cholangitis with unknown etiology, the pathology is more related to the medium-sized intrahepatic bile ducts (<100 μm) rather than hepatocytes, resulting in cholestatic features of the disease with a high level of alkaline phosphatase (ALP) in serum (Kaplan et al. New Engl. J. Med., 2005. 353(12): p. 1261-73). Although ANA may also be detected in PBC, there is a diagnostic autoantibody for PBC that has high sensitivity and specificity (Kaplan et al., supra). This anti-mitochondrial antibody (AMA) is mainly targeted to the E2 subunit of pyruvate dehydrogenase, which is primarily expressed on the cell surface of biliary epithelial cells through translocation from the inner membrane of mitochondria to the cell surface (anti-PDC-E2) and is reported in 95% of PBC cases with a specificity of 100%. In addition, elevated immunoglobulins, especially IgM as well as specific histologic features such as bile duct damage, ductopenia, and granulomatous portal inflammation may help with diagnosis. Similar to AIH, PBC is more common in women and is currently considered as a liver-specific autoimmune disease occurring in genetically predisposed individuals with association to other autoimmune conditions such as Sjogren syndrome and thyroid disease; however, unlike other autoimmune diseases, PBC has not been reported in children.

Similar to PBC, PSC is also a chronic cholestatic condition; however, it affects all size of bile ducts that ultimately results in cirrhosis (Angulo, et al. Clinics in Liver Disease, 1999. 3(3): p. 529-70; Angulo, et al. Primary Sclerosing Cholangitis. Hepatology, 1999. 30(1): p. 325-32). In contrast to PBC, there is no specific autoantibody, immunologic, biochemical or serological diagnostic marker for PSC (Boyer T., M. M., Sanyal A., Zakim and Boyer's Hepatology. Sixth ed. 2011, p. 1408). The diagnosis is based on the endoscopic retrograde cholangiography (ERC) and magnetic resonance cholangiography (MRC), which are showing the typical strictures and dilations in intra- and extrahepatic bile ducts along with the exclusion of other causes of the typical multifocal biliary strictures and intervening dilatations. This feature is due to periductular fibrosis with concentric layers of fibrous tissue called onion skin fibrosis, which is seen only in 14% of PSC patients in liver biopsy as another typical hallmark for PSC; however, it is not specific and can be described in other liver diseases such as ischemic cholangitis (Burak, K. W., P. Angulo, and K. D. Lindor, Is there a role for liver biopsy in primary sclerosing cholangitis? The American journal of gastroenterology, 2003. 98(5): p. 1155-8). Patients with PSC could also have AIH or IgG4-associated sclerosing cholangitis, which will further complicate the diagnosis of PSC. Unlike PBC, PSC is highly associated with inflammatory bowel diseases (IBD), especially ulcerative colitis (UC), which is reported in more than 80% of PSC cases with or without AIH (Ponsioen, et al., Gut, 2002. 51(4): p. 562-6; Tischendorf, et al., Am J. Gastroenterol. 2007. 102(1): p. 107-14). The diagnosis of PSC usually is made in pre-existing IBD patients or even in an IBD patient after colectomy, but in some cases, it may precede the IBD onset by many years (Schrumpf, et al. Scan. J. Gastroenterol. 1982. 17(1): p. 33-9). In Crohn's disease (another IBD), which is more confined to the small intestines, PSC usually develops when the disease is extensive and severe with involvement of colon, which indicates that colitis in IBDs is a prerequisite for comorbidity of PSC with IBD.

The measurement of the level of alkaline phosphatase (AP) in the serum is often included in routine medical screening or in the initial work-up panel for patients presenting with symptoms of liver diseases. The elevated levels of AP (AP+) are usually indicative of a cholestatic type of liver disease such as PSC. However, although serum alkaline phosphatase (AP) is elevated in both PSC and PBC, the level of AP may not consistently stay elevated in a large proportion of the patients during the course of disease, and could even be detected at normal levels. In addition, the increased levels of AP have also been reported in up to 20% of the general population. Thus, although a lower or higher ratio of ALP to alanine aminotransaminase (ALT)/aspartate aminotransferase (AST) could be used in favor of a diagnosis of infectious hepatitis/AIH or PBC/PSC, respectively, this ratios or individual values of each biomarker are not able to distinguish infectious hepatitis from AIH or PBC from PSC.

Bilirubin levels are not a sufficient diagnostic marker either, as it is elevated in only 15-40% of the PSC cases, is also present in other liver diseases, and usually is associated with progressed liver damage. ALT and AST levels, which are mainly indicators of hepatocyte damage are often moderately elevated in PBC and PSC or may even be detected at normal levels. Since there is usually a delay of several years between the onset of PSC and the appearance of the diagnostic feature in cholangiography, it would be highly valuable if the disease could be diagnosed at early stages, when the liver damage is still reversible. In addition, imaging is expensive and not good for screening (ERC and MRC), suboptimal (MRC), and invasive with potential complications such as pancreatitis, bacterial cholangitis, perforation and bleeding.

Liver function tests (LFTs) are the most common way for detecting a liver disease; however, they are indicative of a general liver disorder rather than a specific diagnosis and at least one of the LFTs is elevated in more than 20% of a general population (Donnan, et al. Health Technology Assessment, 2009. 13(25): p. iii-iv, ix-xi, 1-134). In addition, there is a chance of 30% for ALP to be elevated in a non-hepatic disease. The level of γ-glutamyl transferase (GGT) correlates to ALP with higher sensitivity but less specificity as it is elevated in most acute and chronic liver diseases. It may also been released from other organs and is changing by age and sex; however, its elevated levels is more correlated with intra-hepatic biliary disorder such as PBC (Donnan et al., supra; Whitehead, et al., Gut, 1999. 45(1): p. 129-33).

Thus, diagnosis of AIH, PBC and PSC is complex, especially when there is an overlap syndrome, in which the patient presents with clinical symptoms of more than one of these diseases. Such overlap syndromes could be as common as 30% between AIH, PSC, and PBC. Although AMA levels can facilitate a differential diagnosis of PBC from AIH and PSC, better tools for differentiating between AIH and PSC are needed. Diagnostic tools such ERC and liver biopsy histopathology are expensive and invasive (with concomitant risk of complications) and/or are able to diagnose the disease only at late stages with extensive scarring and strictures. Thus, there is a need for diagnostic tools to facilitate differential diagnosis of theses chronic clinical manifestations. Discovery of new parameters to facilitate more efficient, earlier, and differential diagnosis of the AIH, PBC, and PSC would provide advancement in the field.

SUMMARY

The present disclosure provides methods and compositions that find use in facilitating a diagnosis of inflammatory liver disease in a subject. The methods and compositions generally involve detection of eotaxin-3 (E3) levels, either alone or with levels of eotaxin-1 (E1), and optionally, with levels of Macrophage-Derived Chemokine (MDC) and, further optionally, with levels of IL-15. These levels can be used to facilitate a diagnosis of a liver disease of at least one of autoimmune hepatitis (AIH), primary biliary cirrhosis (PBC), and primary sclerosing cholangitis (PSC), and/or to facilitate a differential diagnosis between AIH, PBC, and PSC. For example, as demonstrated herein, E3 levels are highly elevated in PSC, PBC and AIH patients as compared to subjects not having PSC, PBC or AIH. Accordingly, E3 alone has diagnostic utility for each of these liver diseases. Moreover, as demonstrated herein, E1 levels are elevated in PSC but lower in PBC and AIH, such that the E1/E3 ratio may be used to discriminate these three diseases. Also demonstrated herein is that MDC levels are lower in PSC, PBC and AIH in comparison to healthy controls and higher in PSC and AIH in comparison to PBC, enabling discrimination of PSC and AIH from PBC based on MDC levels. The present disclosure further demonstrates that IL-15 levels are higher in AIH, such that the levels of all four cytokines may be used to aid in differential diagnosis of PSC, PBC and AIH. The methods and compositions of the present disclosure also find use in facilitating treatment decisions for a subject.

The present disclosure provides methods for facilitating a diagnosis of a liver disease in a subject, the method comprising detecting a level of eotaxin-3 (E3) in a biological sample from a subject (e.g., a subject suspected of having liver disease, an apparently healthy subject undergoing routine medical screening, a subject with an unspecified morbidity under investigation, or other subject of interest) of at least one of autoimmune hepatitis (AIH), primary sclerosing cholangitis (PSC), and primary biliary cirrhosis (PBC). The level of E3 detected, compared to a control E3 level, can be used to facilitate a diagnosis of liver disease in the subject. In related methods, the method is used to facilitate a diagnosis of a liver disease of at least one of AIH, PBC, and PSC in the subject.

The present disclosure provides methods for facilitating diagnosis of a liver disease in a subject, the method comprising detecting a level of E3 and a level of eotaxin-1 (E1) and a level of macrophage-derived chemokine (MDC) in a biological sample of a subject (e.g., a subject suspected of having liver disease, an apparently healthy subject undergoing routine medical screening, a subject with an unspecified morbidity under investigation, or other subject of interest) of at least one of AIH, PBC and PSC. The E3, E1, and MDC levels can be used to facilitate a differential diagnosis of PSC from among AIH, PBC, and PSC. The method can optionally include detecting a level of alkaline phosphatase (AP) in a biological sample of the subject, e.g., where the subject is suspected of having PSC.

The present disclosure provides methods for facilitating diagnosis of a liver disease in a subject, the method comprising detecting a level of E3 and a level of eotaxin-1 (E1), a level of macrophage-derived chemokine (MDC), and interleukin-15 (Il-15) in a biological sample of a subject (e.g., a subject suspected of having liver disease, an apparently healthy subject undergoing routine medical screening, a subject with an unspecified morbidity under investigation, or other subject of interest) of at least one of AIH, PBC and PSC. The E3, E1, MDC, and IL-15 levels can be used to facilitate a differential diagnosis of AIH from among AIH, PBC, and PSC.

The present disclosure provides methods of facilitating a diagnosis of a liver disease in a subject, the method comprising assaying a level of eotaxin-3 (E3) in a biological sample from a subject (e.g., a subject suspected of having liver disease, an apparently healthy subject undergoing routine medical screening, a subject with an unspecified morbidity under investigation, or other subject of interest); comparing the level of E3 to a control E3 level; wherein an E3 level that is greater than the control E3 level indicates an increased likelihood of a liver disease in the subject. In related methods, the method is used to facilitate a diagnosis of a liver disease of at least one of AIH, PBC, and PSC in the subject. The method can optionally include generating a report indicating a likelihood of a liver disease (e.g., a liver disease of at least one of AIH, PSC, and PBC) in the subject, based on results of comparing of the level of E3 to the control E3 level. The report can optionally include guidance to a clinician as to a treatment recommendation for the subject based on the likelihood of the liver disease.

The present disclosure provides methods of facilitating a diagnosis of a liver disease in a subject, the method comprising assaying a level of E3 in a biological sample from a subject (e.g., a subject suspected of having liver disease, an apparently healthy subject undergoing routine medical screening, a subject with an unspecified morbidity under investigation, or other subject of interest); comparing the level of E3 to a control E3 level; assaying a level of eotaxin-1 (E1) in a biological sample from the subject; calculating a ratio of E1 and E3 levels using the level of E1 and the level of E3; comparing the ratio of E1 and E3 levels a control ratio of E1 and E3 levels; and assaying a level of macrophage-derived chemokine (MDC) in a biological sample from the subject; comparing the MDC level to a control MDC level; wherein an E3 level, a ratio of E1 and E3, and a level of MDC greater than their respective control levels indicates an increased likelihood of PSC in the subject. The method can optionally include generating a report indicating a likelihood of PSC in the subject, based on results of comparing of the level of E3 to the control E3 level, comparing the ratio of E1 and E3 to a control ratio and comparing the MDC level to a control MDC level. The report can further optionally include an indication of the likelihood of at least one of AIH, PBC, and PSC in the subject based on the E3 level. The report(s) can optionally include guidance to a clinician as to a treatment recommendation for the subject based on the likelihood of the liver disease.

The present disclosure provides methods of facilitating a diagnosis of a liver disease in a subject, the method comprising assaying a level of E3 in a biological sample from a subject (e.g., a subject suspected of having liver disease, an apparently healthy subject undergoing routine medical screening, a subject with an unspecified morbidity under investigation, or other subject of interest); comparing the level of E3 to a control E3 level; assaying a level of eotaxin-1 (E1) in a biological sample from the subject; comparing the E1 level to a control E1 level; calculating a ratio of E1 and E3 levels using the level of E1 and the level of E3; comparing the ratio of E1 and E3 levels a control ratio of E1 and E3 levels; assaying a level of MDC in a biological sample from the subject; comparing the MDC level to a control MDC level; assaying a level of interleukin-15 (IL-15) in a biological sample of the subject; comparing the level of IL-15 to a control IL-15 level; wherein an E3 level, a ratio of E1 and E3, a level of MDC, and a level of IL-15 greater than their respective control levels indicates an increased likelihood of AIH in the subject. The method can optionally include generating a report indicating a likelihood of AIH in the subject, based on results of comparing of the level of E3 to the control E3 level, comparing the ratio of E1 and E3 to a control ratio, comparing the MDC level to a control MDC level, and comparing the IL-15 level to a control IL-15 level. The method can optionally include generating a report indicating a likelihood of PSC in the subject, based on results of comparing of the level of E3 to the control E3 level, comparing the ratio of E1 and E3 to a control ratio and comparing the MDC level to a control MDC level. The report can further optionally include an indication of the likelihood of at least one of AIH, PBC, and PSC in the subject based on the E3 level. The report(s) can optionally include guidance to a clinician as to a treatment recommendation for the subject based on the likelihood of the liver disease.

The present disclosure provides methods of facilitating a diagnosis of PSC in a subject suspected of having PSC, the method comprising assaying a level of E3 in a biological sample from a subject suspected of having liver disease; comparing the level of E3 to a control E3 level; assaying a level of alkaline phosphatase (AP) in a biological sample of the subject; comparing the AP level to a control AP level; wherein an E3 level or an AP level greater than their respective control levels in a subject suspected of having PSC (e.g., is AIH negative, is PBC negative or both) indicates an increased likelihood of PSC in the subject. The method can optionally include generating a report indicating a likelihood of PSC in the subject, based on results of comparing of the level of E3 to the control E3 level and comparing the AP level to the control AP level. The report(s) can optionally include guidance to a clinician as to a treatment recommendation for the subject based on the likelihood of the liver disease.

The present disclosure provides methods of facilitating a diagnosis of a liver disease in a subject, the method comprising assaying a level of E3 in a biological sample from a subject (e.g., a subject suspected of having liver disease, an apparently healthy subject undergoing routine medical screening, a subject with an unspecified morbidity under investigation, or other subject of interest); comparing the level of E3 to a control E3 level; assaying a level of eotaxin-1 (E1) in a biological sample from the subject; comparing the E1 level to a control E1 level; calculating a ratio of E1 and E3 levels using the level of E1 and the level of E3; comparing the ratio of E1 and E3 levels a control ratio of E1 and E3 levels; assaying a level of MDC in a biological sample from the subject; comparing the MDC level to a control MDC level; assaying a level of interleukin-15 (IL-15) in a biological sample of the subject; comparing the level of IL-15 to a control IL-15 level; assaying a level of alkaline phosphatase (AP) in a biological sample of the subject; and comparing the AP level to a control AP level; wherein an E3 level, a ratio of E1 and E3, a level of MDC, and a level of IL-15 greater than their respective control levels indicates an increased likelihood of AIH in the subject. The method can optionally include generating a report indicating a likelihood of AIH in the subject, based on results of comparing of the level of E3 to the control E3 level, comparing the ratio of E1 and E3 to a control ratio, comparing the MDC level to a control MDC level, and comparing the IL-15 level to a control IL-15 level. The method can optionally include generating a report indicating a likelihood of a liver disease in a subject based on the results of the assayed biomarkers. The method can optionally include generating a report indicating a likelihood of PSC in the subject, based on results of comparing of the level of E3 to the control E3 level, comparing the ratio of E1 and E3 to a control ratio and comparing the MDC level to a control MDC level. The report can optionally include an indication of the likelihood of at least one of AIH, PBC, and PSC in the subject based on the E3 level. The report can optionally include an indication of whether a subject is suspected of having PSC (e.g., is AIH negative and/or PBC negative), and an indication of the likelihood of PSC in the subject based on the E3 level or AP level in the subject. The report(s) can optionally include guidance to a clinician as to a treatment recommendation for the subject based on the likelihood of the liver disease.

The biological sample used in the methods of the present disclosure can be blood or blood product, e.g., serum or plasma.

The methods of the present disclosure can include selecting a therapy for the subject based on the likelihood of the liver disease. The methods of the present disclosure can include administering a therapy for the subject based on the likelihood of the liver disease. Where the subject is undergoing therapy, the methods of the present disclosure can include modifying therapy for the subject based on the results of the assay(s).

The methods of the present disclosure can involve inputting the E3 level, the E1 level, the MDC level, and/or IL-15 level into a computer programmed to execute an algorithm to perform the comparing and calculating step(s), wherein said inputting generates a result for a report. The report can be displayed to an output device, e.g., at a location remote to the computer.

The present disclosure provides kits comprising a binding reagent for eoxtain-3 (E3); a binding reagent for eoxtain-1 (E1); a binding reagent for macrophage-derived chemokine (MDC); and a binding reagent for IL-15 (IL-15), and, optionally, one or more reagents for detecting alkaline phosphatase. In some embodiments, the kit includes a binding reagent for E3 and a reagent to detect alkaline phosphatase (AP). In some embodiments, the reagent to detect AP can provide for detection of enzymatic activity of AP. The binding reagent for E3, the binding reagent for E1, the binding reagent for MDC and the binding reagent for IL-15 can be an antibody or a at least a ligand-binding portion of a receptor. The kit can include a binding reagent for a control analyte.

The present disclosure provides methods of treating a subject having a liver disease of at least one of autoimmune hepatitis (AIH), primary sclerosing cholangitis (PSC), and primary biliary cirrhosis (PBC), the method comprising administering to the subject an effective amount of an antagonist of eotaxin-3 (E3).

The present disclosure provides methods of treating a subject having primary sclerosing cholangitis (PSC), the method comprising administering to the subject an effective amount of an antagonist of eotaxin-1 (E1).

The present disclosure provides methods of facilitating a diagnosis of a liver disease in a patient (e.g., a patient suspected of having liver disease, an apparently healthy patient undergoing routine medical screening, a patient with an unspecified morbidity under investigation, or other patient of interest), the method comprising receiving, with a processor, assay data including a level of eotaxin-3 (E3) in a biological sample of a subject; comparing, with the processor, the level of E3 to a control E3 level; and generating, with the processor, a report including the E3 level and indicating a likelihood of a liver disease in the subject; wherein an E3 level that is greater than the control E3 level indicates an increased likelihood of a liver disease in the patient. In related methods, the method is used to facilitate a diagnosis of a liver disease of at least one of AIH, PBC, and PSC in the patient.

The method can further include receiving, with a processor, assay data including a level of eotaxin-1 (E1) and a level of macrophage-derived chemokine (MDC) in a biological sample of the subject; calculating a ratio of E1 and E3 levels using the level of E1 and the level of E3; and comparing the ratio of E1 and E3 levels a control ratio of E1 and E3 levels; and comparing the MDC level to a control MDC level; wherein an E3 level greater than the control E3 level, a ratio of E1 and E3 levels greater than a control ratio, and an MDC level greater than the control MDC level, indicates an increased likelihood of PSC in the subject. The method can still further include receiving, with a processor, assay data including a level of interleukin-15 (IL-15) in a biological sample from the subject; comparing the IL-15 level to a control IL-15 level; wherein an IL-15 level greater than the control IL-15 level, an MDC level greater than the control MDC level, an E3 level greater than the control E3 level, and an ratio of E1 and E3 levels greater than a control ratio indicates an increased likelihood of AIH in the subject. The method can include receiving, with a processor, assay data including a level of E3 in a biological sample of a subject; comparing, with the processor, the level of E3 to a control E3 level; assay data including a level of alkaline phosphatase (AP) in a biological sample of a subject; comparing, with the processor, the level of AP to a control AP level; wherein in a subject that is suspected of having PSC (e.g., is AIH negative and/or PBC negative), an E3 level that is greater than the control E3 level and/or an AP level that is greater than a control AP level indicates an increased likelihood of PSC in the patient. In related embodiments, the method(s) can include communicating the report with a communication module operably coupled to the processor.

The present disclosure provides computer systems, comprising a processor; and memory operably coupled to the processor, wherein the memory includes instructions stored therein for diagnosing a liver disease in a patient (e.g., a patient suspected of having liver disease, an apparently healthy patient undergoing routine medical screening, a patient with an unspecified morbidity under investigation, or other patient of interest), wherein the instructions, when executed by the processor, cause the processor to: receive assay data including a level of eotaxin-3 (E3) in a biological sample of a patient; compare the level of E3 to a control E3 level; and generate a report including the E3 level and indicating a likelihood of a liver disease in the patient; wherein an E3 level that is greater than the control E3 level indicates an increased likelihood of a liver disease in the patient. In related computer systems, the liver disease is at least one of AIH, PSC and PBC. The instructions of the computer system can further cause the processor to: receive assay data including a level of eotaxin-1 (E1) and a level of macrophage-derived chemokine (MDC) in a biological sample of a patient; calculate a ratio of E1 and E3 levels using the level of E1 and the level of E3; and compare the ratio of E1 and E3 levels a control ratio of E1 and E3 levels; compare the MDC level to a control MDC level; and wherein an E3 level greater than the control E3 level, a ratio of E1 and E3 levels greater than a control ratio, and an MDC level greater than the control MDC level, indicates an increased likelihood of PSC in the subject. The instructions of the computer system can still further cause the processor to: receive assay data including a level of interleukin-15 (IL-15) in a biological sample from the subject; compare the IL-15 level to a control IL-15 level; and wherein an IL-15 level greater than the control IL-15 level, an MDC level greater than the control MDC level, an E3 level greater than the control E3 level, and an ratio of E1 and E3 levels greater than a control ratio indicates an increased likelihood of AIH in the subject. The computer system can receive assay data including a level of E3 in a biological sample of a patient; compare the E3 level to a control E3 level; receive assay data including a level of alkaline phosphatase (AP) in a biological sample of a patient; compare the AP level to a control AP level; wherein in a subject that is suspected of having PSC (e.g., is AIH negative, is PBC negative, or both), an E3 level greater than the control E3 level and/or an AP level greater than the control AP level indicates an increased likelihood of PSC in the subject.

The computer systems of the present disclosure can include a communication module for communicating the report over a network, the communication module operably coupled to the processor; wherein the memory includes instructions, that when executed by the processor, cause the processor to communicate the report via the communication module.

The present disclosure provides computer-implemented methods of facilitating a diagnosis of a liver disease in a patient (e.g., a patient suspected of having liver disease, an apparently healthy patient undergoing routine medical screening, a patient with an unspecified morbidity under investigation, or other patient of interest), comprising: receiving assay data including a level of eotaxin-3 (E3) in a biological sample of a patient; comparing the level of E3 to a control E3 level; and generating a report including the E3 level and indicating a likelihood of a liver disease in the patient; wherein an E3 level that is greater than the control E3 level indicates an increased likelihood of a liver disease in the patient. In related methods, the liver disease is at least one of AIH, PSC, and PBC. The computer-implemented methods can include receiving assay data including a level of eotaxin-1 (E1) and a level of macrophage-derived chemokine (MDC) in a biological sample of a patient; calculating a ratio of E1 and E3 levels using the level of E1 and the level of E3; and comparing the ratio of E1 and E3 levels a control ratio of E1 and E3 levels; comparing the MDC level to a control MDC level; and wherein an E3 level greater than the control E3 level, a ratio of E1 and E3 levels greater than a control ratio, and an MDC level greater than the control MDC level, indicates an increased likelihood of PSC in the subject. The computer-implemented methods can still further include receiving assay data including a level of interleukin-15 (IL-15) in a biological sample from the subject; comparing the IL-15 level to a control IL-15 level; and wherein an IL-15 level greater than the control IL-15 level, an MDC level greater than the control MDC level, an E3 level greater than the control E3 level, and an ratio of E1 and E3 levels greater than a control ratio indicates an increased likelihood of AIH in the subject. The computer-implemented method can include receiving assay data including a level of E3 in a biological sample of a patient; comparing the E3 level to a control E3 level; receiving assay data including a level of alkaline phosphatase (AP) in a biological sample of a patient; comparing the AP level to a control AP level; wherein in a subject that is suspected of having PSC (e.g., is AIH negative, is PBC negative, or both), an E3 level greater than the control E3 level and/or an AP level greater than the control AP level indicates an increased likelihood of PSC in the subject.

These and other features will be apparent to the ordinarily skilled artisan upon reviewing the present specification.

BRIEF DESCRIPTION OF THE DRAWINGS

FIGS. 3-8 provide tables showing algorithms based on eotaxin-1 (E1), eotaxin-3 (E3), CCL22 (MDC), and IL-15 levels and results when used to detect AIH, PBC, and/or PSC and to provide a differential diagnosis from healthy and HCV-infected control individuals, as well as a differential diagnosis between AIH, PBC, and PSC.

FIG. 9); eotaxin-1 (Eotaxin (also referred to as "E1"); FIG. 10), macrophage-derived chemokine (MDC, FIG. 11), interleukin-15 (IL-15; FIG. 12), and the ratio of E1/E3 (FIG. 13).

FIG. 14 provides a table showing the results of evaluation of accuracy of diagnostic algorithms of the present disclosure.

FIG. 15 provides a) a schematic and b) table illustrating detection of patients with confirmed PSC by detection of elevated serum levels of eotaxin-3 (E3) or alkaline phosphatase (AP).

DETAILED DESCRIPTION OF EMBODIMENTS

Figure 1:
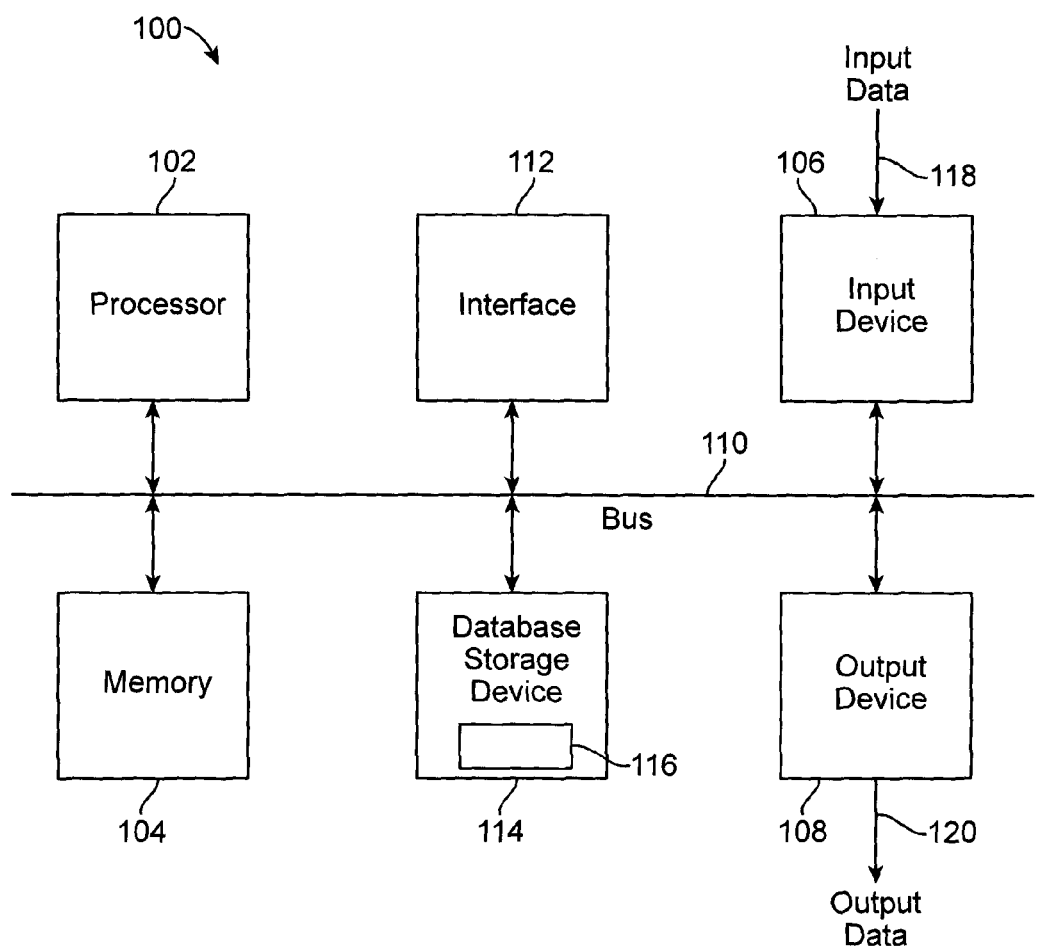
FIG. 1 provides a general schematic of a computerized system for use in the methods of the present disclosure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to "the polypeptide" includes reference to one or more polypeptides and equivalents thereof known to those skilled in the art, and so forth.

The publications discussed herein are provided solely for their disclosure prior to the priority date of the present application. Nothing herein is to be construed as an admission that the present invention is not entitled to antedate such publication by virtue of prior invention. Further, the dates of publication provided may be different from the actual publication dates which may need to be independently confirmed.

Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Definitions

"Autoimmune hepatitis" or "AIH" refers to a chronic inflammatory liver disease in which loss of tolerance of hepatic tissue is presumed and the body's immune system attacks cells of the liver. This abnormal immune response results in inflammation of the liver, which can lead to further complications such as cirrhosis. The pathology of AIH, which is more common in women than men, begins with damage to hepatocytes resulting in interface hepatitis and piecemeal necrosis accompanied by leukocyte infiltration eventually followed by fibrosis and cirrhosis. AIH can be associated with anti-nuclear antibodies (ANA), anti-smooth muscle antibodies (SMA), antibodies to liver/kidney microsome type 1 (anti-LKM1) antibodies to soluble liver/pancreas antigen (anti-SLA/LP), perinuclear anti-neutrophil cytoplasmic antibodies (pANCA), antibodies to liver-specific cytosol antigen type 1 (anti-LC1), and anti-actin antibodies (Manns, et al. Hepatology, 2010. 51(6): p. 2193-213; Czaja, et al. Gastroenterology, 2010. 139(1): p. 58-72 e4). Since these autoantibodies are not specific for AIH and may be detected in patients with PBC, PSC, viral hepatitis, drug-induced hepatitis, and alcoholic hepatitis, the International Autoimmune Hepatitis Group has suggested a diagnostic algorithm, which is provided below as a coded panel, for diagnosis of AIH. An algorithm to facilitate a diagnosis definite, probable, or lack of AIH, based on four parameters including the levels of different autoantibodies, the level of IgG, liver histology, and absence of a known viral infection has been described (see, Lohse, et al. J. Hepatol. 2011. 55(1): p. 171-82) is summarized below:

| | | Points |
|---|---|---|
| Autoantibodies | ANA or SMA or LKM >1:40 | 1 |
| | ANA or SMA or LKM >1:80 | 2 |
| | SLA/LP Positive (>20 units) | |
| IgG (or gamma-globuius) | Upper normal limit >1.10 | 1 |
| | times normal limit | 2 |
| Liver histology* | Compatible with AIH | 1 |
| | Typical for AIH | 2 |
| Absence of viral hepatitis | Yes | 2 |
| | No | 0 |

Definite autoimmune hepatitis (AIH): ≥7; probable AIH: ≥6.
ANA, antinuclear

"Primary biliary cirrhosis" or "PBC" (which is also known as also called chronic nonsuppurative destructive cholangitis) refers to a chronic non-suppurative destructive granulomatous cholangitis with unknown etiology in which the pathology is more related to the medium-sized intrahepatic bile ducts rather than hepatocytes, resulting in cholestatic features of the disease with a high level of alkaline phosphatase (ALP) in serum (Kaplan et al. The New England Journal of Medicine, 2005. 353(12): p. 1261-73). Inflammation usually starts adjacent the biliary system, resulting in cholestatic disease leading to fibrosis. Although other autoantibodies (e.g., ANA) may be detected in PBC, the anti-mitochondrial antibody (AMA) against acyltransferases of the inner mitochondrial membrane has high sensitivity and specificity for PBC (Kaplan et al. supra) and is reported in 95% of PBC cases. In addition, elevated immunoglobulins, especially IgM, as well as specific histologic features such as bile duct damage, ductopenia, and granulomatous portal inflammation are indicative of a PBC diagnosis. As with AIH, PBC is more common in women and is currently considered as a liver-specific autoimmune disease occurring in genetically predisposed individuals with association to other autoimmune conditions such as Sjogren syndrome and thyroid disease. PBC is generally not reported in children. "Children" as used herein refers to individuals under 12 years old.

"Primary sclerosing cholangitis" or "PSC" refers to a chronic cholestatic condition that affects all sizes of bile ducts (Angulo, et al. Clinics in Liver Disease, 1999. 3(3): p. 529-70; Angulo, et al. Hepatology, 1999. 30(1): p. 325-32). As in PBC, the inflammation in PSC usually starts adjacent the biliary system resulting in cholestatic disease leading to fibrosis and cirrhosis. Up to about 80% of PSC cases are associated with inflammatory bowel disease, in particular ulcerative colitis. The disease can be complicated by the development of bile duct cancer in up to 15%. In addition, the incidence of pancreatic cancer and colonic cancer is increased relative to unaffected individuals. Because no specific autoantibody, immunologic, biochemical or serological diagnostic marker for PSC has been available prior to the present disclosure, diagnosis is usually based on the endoscopic retrograde cholangiography (ERC) and/or magnetic resonance cholangiography (MRC), which are showing the typical strictures and dilations in intra- and extrahepatic bile ducts, along with the exclusion of other causes of the typical multifocal biliary strictures and intervening dilatations. On liver biopsy, periductular fibrosis with concentric layers of fibrous tissue called onion skin fibrosis can be observed. PSC is more common in men than women.

The terms "individual," "subject," and "patient," used interchangeably herein, refer to a human.

The term "healthy individual" in the context of the diagnostic methods of the present disclosure refers to an individual who is unaffected by a detectable illness, particularly a liver disease, particularly an individual who is unaffected by hepatitis (e.g., viral or autoimmune hepatitis), more particularly an individual who is unaffected by a liver disease of one or more of AIH, PBC and PSC. Healthy individuals include those who have not reported any complaint, symptom or sign of any diseases at the time of visit and, optionally, for the last month; have not had any history of liver disease; are not undergoing therapy for a disease, particularly for a liver disease; have normal complete blood count (CBC) differential test, as well as normal level of serum ALT (alanine aminotransaminase) and serum GGT (γ-glutamyl transferase); are negative for biliary disease; test negative for viral hepatitis (e.g., HCV infection, HBV infection); test negative for HIV infection; and are negative for nonalcoholic steatohepatitis (NASH), alcohol-induced hepatitis, and drug-induced hepatitis.

The terms "polypeptide," "peptide" and "protein", used interchangeably herein, refer to a polymeric form of amino acids of any length, which can include biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. "NH$_2$" refers to the free amino group present at the amino terminus of a polypeptide and "COOH" refers to the free carboxyl group present at the carboxyl terminus of a polypeptide in keeping with standard polypeptide nomenclature, *J. Biol. Chem.*, 243 (1969), 3552-59 is used.

In the context of a polypeptide present in a biological sample, "polypeptide" refers to a naturally-occurring polypeptide present in an individual from whom the sample is obtained.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Guidance for such substitutions can be drawn from alignments of amino acid sequences of polypeptides.

A "biomarker" or "marker" as used herein generally refers to an organic biomolecule (e.g., a polypeptide) which is differentially present in a sample taken from a subject of one phenotypic status (e.g., having a disease) as compared with another phenotypic status (e.g., not having the disease or having a different disease). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. As such, biomarkers can find use as markers for, for example, disease (diagnostics), therapeutic effectiveness of a drug (theranostics), and the like. Biomarkers are thus analytes in assays that facilitate diagnosis, theranostics, and the like.

A "biological sample" encompasses a variety of sample types obtained from an individual. The definition encompasses biological fluids (e.g., blood (including blood fractions (e.g., serum, plasma)); and other liquid samples of biological origin (e.g., saliva, urine, bile fluid), as well as solid tissue samples in the form of a liver biopsy specimen. "Blood sample" refers to a biological sample, which is obtained from blood of a subject, and includes whole blood and blood fractions (e.g., plasma or serum) suitable for analysis in the present methods. In general, separation of cellular components and non-cellular components in a blood sample (e.g., by centrifugation) without coagulation provides a blood plasma sample, while such separation of coagulated (clotted) blood provides a blood serum sample. Examples of biological samples of blood include peripheral blood or samples derived from peripheral blood. The definition also includes samples that have been manipulated after their procurement, such as by treatment with reagents, solubilization, or enrichment for certain components, such as one or more polypeptides to be assayed. For example, a biological sample (e.g., blood) can be enriched for a fraction containing an analyte(s) of interest.

"Isolated" refers to an entity of interest that is in an environment different from that in which the compound may naturally occur. "Isolated" is meant to include compounds that are within samples that are substantially enriched for the compound of interest and/or in which the compound of interest is partially or substantially purified.

By "purified" is meant a compound of interest (e.g., a polypeptide) has been separated from components that accompany it in nature. "Purified" can also be used to refer to a compound of interest separated from components that can accompany it during manufacture (e.g., in chemical synthesis). In some embodiments, a compound is substantially pure when it is at least 50% to 60%, by weight, free from organic molecules with which it is naturally associated or with which it is associated during manufacture. In some embodiments, the preparation is at least 75%, at least 90%, at least 95%, or at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample that contains the compound. A substantially pure compound can also be obtained by recombinant or chemical synthetic production. Purity can be measured by any appropriate method, e.g., chromatography, mass spectroscopy, high performance liquid chromatography analysis, etc.

As used herein, the terms "determining", "assessing", "assaying", "measuring" and "detecting" refer to both quantitative and semi-quantitative determinations and as such, the term "determining" is used interchangeably herein with "assaying," "measuring," and the like. Where a quantitative determination is intended, the phrase "determining an amount" of an analyte and the like is used. Where either a quantitative and semi-quantitative determination is intended, the phrase "determining a level" of an analyte or "detecting" an analyte is used.

"Quantitative" assays in general provide information on the amount of an analyte in a sample relative to a reference (control), and are usually reported numerically, where a "zero" value can be assigned where the analyte is below the limit of detection. "Semi-quantitative" assays involve presentation of a numeric representation of the amount of the analyte in the specimen that is relative to a reference (e.g., a threshold, e.g., normal threshold or an abnormal threshold), where a "zero" value can be assigned where the analyte is below the limit of detection. In general, semi-quantitative results are compared against an accompanying reference interval to provide a qualitative interpretation of the result.

"Sensitivity" refers to the fraction of people with the disease that a test correctly identifies as positive. "Specificity" refers to the fraction of people without the disease that the test correctly identifies as negative. The fractions with respect to sensitivity and/or specificity may be presented as a percentage. Where expressed as percentages, specificity can be calculated as by subtracting the sensitivity value for incorrect diagnosis from 100. For example, if a test used an algorithm for diagnosis of PSC also incorrectly identified PSC in 8% of AIH cases, the specificity for PSC against AIH would be 92%.

"Antibody" as used herein refers to an antigen-binding protein having one or more polypeptides that can be genetically encodable by immunoglobulin genes, or fragments of immunoglobulin genes, and which bind an antigen of interest. "Antibody" as used herein encompasses whole antibodies as well antigen-binding fragments of whole antibodies. Antigen-binding antibody fragments include, for example, Fab', (Fab')2, and the like. "Fab" as used herein refers to a minimal antigen-binding portion of an antibody that lacks an Fc portion (e.g., a heterodimer of a VH/VL pair of a tetrameric antibody). "(Fab')2" refers to Fab molecules that are covalently linked, usually covalently linked as found in nature, which lack an Fc portion. It should be noted that while various antibody fragments may be defined in terms of the digestion of an intact antibody, one of skill will appreciate that such fragments may be synthesized de novo either chemically or by utilizing recombinant DNA methodology.

Whole antibodies refers to antibodies composed of two pairs of polypeptides, where each pair includes one "light" chain polypeptide and one "heavy" chain polypeptide. The terms variable light chain (VL) and variable heavy chain (VH) refer to the portions of the light and heavy chains that contain the CDRs, respectively. Light chains can be classified according to their constant regions, which can be kappa or lambda. Heavy chains can be classified according to their constant regions, which can be gamma, mu, alpha, delta, or epsilon, which in turn define the immunoglobulin classes, IgG, IgM, IgA, IgD and IgE, respectively.

The term "antibody" encompasses polyclonal and monoclonal antibodies, and further encompasses antibodies of any class (e.g., IgM, IgG, and subclasses thereof). "Antibody" also encompasses hybrid antibodies, bispecific antibodies, heteroantibodies, chimeric antibodies, humanized antibodies, and functional fragments thereof which retain antigen binding. "Bispecific antibodies" may resemble single antibodies (or antibody fragments) but have two different antigen binding sites (variable regions). Heteroantibodies refers to two or more antibodies, or antibody binding fragments (e.g., Fab) linked together, each antibody or fragment having a different specificity. The antibodies may be conjugated to other moieties, and/or may be bound to a support (e.g., a solid support), such as a polystyrene plate or bead, test strip, and the like.

The phrase "specifically binds", when referring to a protein or a binding partner that binds a protein (e.g., an antibody that binds an antigen (e.g., analyte)), refers to a binding reaction between a protein and a binding partner (e.g., antibody and analyte) which is determinative of the presence of the protein in the presence of a heterogeneous population of proteins and other biologics. Thus, under designated conditions, a specified binding partner (e.g., antibody) binds preferentially to a particular protein and does not bind in a significant amount to other proteins present in the sample.

The terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

Methods of Facilitating a Diagnosis of Inflammatory Liver Disease

The present disclosure provides methods for facilitating a diagnosis of a liver disease of one or more of autoimmune hepatitis (AIH), primary biliary cirrhosis (PBC), and primary sclerosing cholangitis (PSC). Diagnosis can involve assessing whether the subject has a liver disease of one or more of AIH, PBC and PSC so as to differentiate the subject from a healthy individual. Diagnosis can involve assessing whether the subject has a liver disease of one or more of AIH, PBC and PSC so as to differentiate the subject from an individual infected with HCV. Diagnosis can involve assessing whether the individual has PSC as opposed to a being a non-PSC affected individual and/or as opposed to having one or both of AIH or PBC. Diagnosis can involve assessing whether the individual has AIH as opposed to being a non-AIH affected individual and/or as opposed to one or both of PBC or PSC.

In general, the methods involve detecting a level of eotaxin-3 (E3) in a biological sample of a subject, particularly a subject suspected of having a liver disease, e.g., a liver disease of at least one of AIH, PBC, or PSC. In addition to detecting a level of E3, the methods optionally include detecting a level of eotaxin-1 (E1) and a level of Macrophage-Derived Chemokine (MDC) in a biological sample from the subject. In addition to detecting a level of E1, E3 and MDC, the methods further optionally include detecting a level of interleukin-15 (IL15). These levels can be used to facilitate a diagnosis of a liver disease of at least one of autoimmune hepatitis (AIH), primary biliary cirrhosis (PBC), and primary sclerosing cholangitis (PSC), and/or to facilitate a differential diagnosis between AIH, PBC, and PSC. The methods and compositions of the present disclosure also find use in facilitating treatment decisions for a subject.

Aspects of the present disclosure include methods of diagnosing a subject for a disease other than a liver disease. In certain aspects, the methods include detecting a level of E3 in a biological sample from a subject (e.g., a subject suspected of having liver disease, an apparently healthy subject undergoing routine medical screening, a subject with an unspecified morbidity under investigation, or other subject of interest). The methods further include diagnosing the individual with an E3-associated disease, such as bullous pemphigoid (Kagami et al., *J Invest Dermatol*. (2012) 132 (1):249-51), granulomatous vasculitis organ damage in Churg-Strauss syndrome (Polzer et al. *Rheumatology* 2008 47(6):804-8), and eosinophilic esophagitis, where it has been suggested as a diagnostic biomarker to differentiate the disease from gastro-esophageal reflux (Bhattacharya et al. *Hum Pathol*. 2007 38(12):1744-53). The multi-functionality of E3 via different receptors including CCR1, CCR2, CCR5, and CX3CR1, may explain the correlation of elevated levels of E3 with different diseases from allergic type diseases (Th2) to autoimmune-like liver diseases (Th1), with diverse infiltration of immune cells. This makes the measurement of E3 levels in serum, etc. a valuable addition to the initial laboratory requisition panel for individuals that are suspected of liver diseases, individuals with unspecified morbidity seeking medical attention, and even healthy individuals undergoing routine medical screening. This would reduce the number of missed undiagnosed cases of autoimmune-like liver diseases (PSC, PBC, and AIH), allergic diseases, bullous pemphigoid, Churg-Strauss syndrome, and eosinophilic esophagitis.

The biomarkers (analytes) used in the methods of the present disclosure, as well as the methods of detection and analysis are described in more detail below.

Biomarkers for Detection

The present methods involve detection of a biomarker (also referred to as an analyte) in a biological sample of a patient. The present methods involve detection of eotaxin-3 (E3; also known as CCL26) in a biological sample. The present methods optionally include, in addition to detection of E3, detection of eotaxin-1 (E1; also known as CCL11) in a biological sample. The present methods further optionally involve detection of E3, E1 and one or both of Macrophage-Derived Chemokine (MDC; also known as CCL22) and interleukin-15 (IL-15). The present methods can further involve detection of other biomarkers Eotaxins E3 and E1

E3

"Eotaxin-3" or "E3" refers to a polypeptide also known as "Chemokine, CC Motif, Ligand 26" (CCL26); and Small Inducible Cytokine Subfamily A, member 26 (SCYA26). E3 is produced as prepolypeptide comprising a signal peptide that is cleaved to generate a mature polypeptide. Examples of human E3 include those comprising an acid sequence of Accession No. AB016542.1; NP_006063; Q9Y258; and BAA84579; and naturally-occurring variants thereof. For example, the amino acid sequence of AB016542.1 is as follows (with the signal peptide at residues 1-23): MMGLSLASAV LLASLLSLHL GTATRGSDIS KTCCFQYSHK PLPWTWVRSY EFTSNSCSQRAVIFTTKRGK KVCTHPRKKW VQKYISLLKT PKQL (SEQ ID NO:1).

For example, the amino acid sequence of NP_006063 is as follows (with the signal peptide at residues 1-23): MMGLSLASAV LLASLLSLHL GTATRGSDIS KTCCFQYSHK PLPWTWVRSY EFTSNSCSQR AVIFTTKRGK KVCTHPRKKW VQKYISLLKT PKQL (SEQ ID NO:2).

For example, the amino acid sequence of Q9Y258 is as follows (with the signal peptide at residues 1-23): MMGLSLASAV LLASLLSLHL GTATRGSDIS KTCCFQYSHK PLPWTWVRSY EFTSNSCSQR AVIFTTKRGK KVCTHPRKKW VQKYISLLKT PKQL (SEQ ID NO:3).

For example, the amino acid sequence of BAA84579 is as follows (with the signal peptide at residues 1-23): MMGLSLASAV LLASLLSLHL GTATRGSDIS KTCCFQYSHK PLPWTWVRSY EFTSNSCSQR AVIFTTKRGK KVCTHPRKKW VQKYISLLKT PKQL (SEQ ID NO:4).

E3 detection encompasses detection of full-length E3, as well as detection of naturally-occurring fragments or other metabolites of E3 found in a biological sample, and detection of fragments or other derivatives generated by manipulation of a biological sample, with the proviso that detection of such fragments, metabolites, or derivatives is specific for detection of E3. E3 fragments are usually at least 10, 15, 20, 25, 30, 35, 40, 45, 50, 55, or 60 amino acids or more in length. E3 detection can also be accomplished by detecting nucleic acid encoding E3 (e.g., RNA encoding E3 or DNA generated from such E3-encoding RNA, e.g., using reverse transcriptase-PCR (RT-PCR)). E3 detection can involve direct detection of E3 or a fragment thereof found in a biological sample, or indirect detection (e.g., by detecting binding of an anti-E3 binding partner, e.g., an anti-E3 antibody).

According to certain embodiments, E3 detection (e.g., serum E3 detection) involves binding of an anti-E3 antibody to E3. Aspects of these embodiments may include binding a detectably-labeled anti-E3 antibody to E3, such that detecting E3 involves detecting the detectable label of the anti-E3 antibody bound to E3. Other aspects of these embodiments may include binding an anti-E3 antibody to E3, followed by binding a detectably-labeled secondary antibody to the anti-E3 antibody, such that detecting E3 involves detecting the detectable label of the secondary antibody. The anti-E3 antibody may be any antibody that specifically binds to E3. According to certain aspects, the anti-E3 antibody is a commercially available anti-E3 antibody, such as a monoclonal or polyclonal anti-E3 antibody available from Abcam®, Abnova, Abgent, Santa Cruz Biotechnology®, United States Biological, ProSci, R&D Systems®, Fitzgerald, Meso Scale Discovery®, or any other commercially available antibody. In certain aspects, the anti-E3 antibody is commercially available as part of a kit, such as a kit for solid phase (e.g., ELISA) based detection of E3 alone, or in combination with any other biomarkers of interest, e.g., eotaxin-1 (E1), Macrophage-Derived Chemokine (MDC), Interleukin-15 (IL-15), alkaline phosphatase (AP), or any combination thereof.

In certain aspects, the E3 present in a sample of interest is directly or indirectly immobilized to a surface, followed by binding of E3 with a detectably-labeled primary anti-E3 antibody, or binding of E3 by an unlabeled primary antibody, which is in turn bound by a detectably-labeled secondary antibody. Any suitable strategy for immobilizing E3 to a surface may be employed. In certain aspects, an anti-E3 "capture" antibody attached to a surface binds the E3 present in the sample of interest, thereby indirectly immobilizing E3 to the surface. In other aspects, a receptor specific for E3 attached to a surface binds the E3 present in the sample of interest, thereby indirectly immobilizing E3 to the surface. Once immobilized, the E3 may be subsequently detected using any convenient approach, such as solid-phase antibody-based detection, e.g., using a detectably-labeled anti-E3 primary antibody, or an unlabeled anti-E3 primary antibody and a detectably-labeled secondary antibody that binds the primary antibody.

E1

"Eotaxin-1" or "E1" refers to a polypeptide also known as Chemokine, CC Motif, Ligand 11 (CCL11); Small Inducible Cytokine Subfamily A, Member 11 (SCYA11); and Small Inducible Cytokine A11. E1 is produced as prepolypeptide comprising a signal peptide that is cleaved to generate a mature polypeptide. Examples of human E1 include those comprising an acid sequence of Accession No. P51671; CAG33702.1; NP_002977; and naturally-occurring variants thereof.

For example, the amino acid sequence of P51671 is as follows (with the signal peptide at residues 1-23): MKVSAALLWL LLIAAAFSPQ GLAGPASVPT TCCFNLANRK IPLQRLESYR RITSGKCPQK AVIFKTKLAK DICADPKKKW VQDSMKYLDQ KSPTPKP (SEQ ID NO:5).

For example, the amino acid sequence of CAG33702.1 is as follows (with the signal peptide at residues 1-23): MKVSAALLWL LLIAAAFSPQ GLAGPASVPT TCCFN- LANRK IPLQRLESYR RITSGKCPQK AVIFKTKLAK DICADPKKKW VQDSMKYLDQ KSPTPKP (SEQ ID NO: 6).

For example, the amino acid sequence of NP_002977 is as follows (with the signal peptide at residues 1-23): MKVSAALLWL LLIAAAFSPQ GLAGPASVPT TCCFNLANRK IPLQRLESYR RITSGKCPQK AVIFKTKLAK DICADPKKKW VQDSMKYLDQ KSPTPKP (SEQ ID NO:7).

E1 detection encompasses detection of full-length E1, as well as detection of naturally-occurring fragments or other metabolites of E1 found in a biological sample, and detection of fragments or other derivatives generated by manipulation of a biological sample, with the proviso that detection of such fragments, metabolites, or derivatives is specific for detection of E1. E1 fragments are usually at least 10, 15, 20, 25, 30, 35, 40, 45, 50, 55, or 60 amino acids or more in length. E1 detection can also be accomplished by detecting nucleic acid encoding E1 (e.g., RNA encoding E3 or DNA generated from such E1-encoding RNA, e.g., using RT-PCR). E1 detection can involve direct detection of E1 or a fragment thereof found in a biological sample, or indirect detection (e.g., by detecting binding of an anti-E1 binding partner, e.g., an anti-E1 antibody).

According to certain embodiments, E1 detection (e.g., serum E1 detection) involves binding of an anti-E1 antibody to E1. Aspects of these embodiments may include binding a detectably-labeled anti-E1 antibody to E1, such that detecting E1 involves detecting the detectable label of the anti-E1 antibody bound to E1. Other aspects of these embodiments may include binding an anti-E1 antibody to E1, followed by binding a detectably-labeled secondary antibody to the anti-E1 antibody, such that detecting E1 involves detecting the detectable label of the secondary antibody. The anti-E1 antibody may be any antibody that specifically binds to E1. According to certain aspects, the anti-E1 antibody is a commercially available anti-E1 antibody, such as a monoclonal or polyclonal anti-E1 antibody available from Abcam®, Abnova, Abgent, Santa Cruz Biotechnology®, United States Biological, ProSci, R&D Systems®, Fitzgerald, Meso Scale Discovery®, or any other commercially available antibody. In certain aspects, the anti-E1 antibody is commercially available as part of a kit, such as a kit for solution phase- or solid phase- (e.g., ELISA-) based detection of E1 alone, or in combination with any other biomarkers of interest, e.g., eotaxin-3 (E3), Macrophage-Derived Chemokine (MDC), Interleukin-15 (IL-15), alkaline phosphatase (AP), or any combination thereof.

In certain aspects, the E1 present in a sample of interest is directly or indirectly immobilized to a surface, followed by binding of E1 with a detectably-labeled primary anti-E1 antibody, or binding of E1 by an unlabeled primary antibody, which is in turn bound by a detectably-labeled secondary antibody. Any suitable strategy for immobilizing E1 to a surface may be employed. In certain aspects, an anti-E1 "capture" antibody attached to a surface binds the E1 present in the sample of interest, thereby indirectly immobilizing E1 to the surface. In other aspects, a receptor specific for E1 attached to a surface binds the E1 present in the sample of interest, thereby indirectly immobilizing E1 to the surface. Once immobilized, the E1 may be subsequently detected using any convenient approach, such as solid-phase antibody-based detection, e.g., using a detectably-labeled anti-E1 primary antibody, or an unlabeled anti-E1 primary antibody and a detectably-labeled secondary antibody that binds the primary antibody.

MDC (CCL22)

"Macrophage-Derived Chemokine" or "MDC" refers to a polypeptide also known as Chemokine, CC Motif, Ligand 22 ("CCL22") and Small Inducible Cytokine Subfamily A, Member 22 (SCYA22). MDC is produced as prepolypeptide comprising a signal peptide that is cleaved to generate a mature polypeptide. Examples of human MDC include those comprising an acid sequence of Accession No. NP_002981; 000626; EAW82918; and naturally-occurring variants thereof.

For example, the amino acid sequence of NP_002981 is as follows (with the signal peptide at residues 1-24): MDRLQTALLV VLVLLAVALQ ATEAGPYGAN MEDSVCCRDY VRYRLPLRVV KHFYWTSDSC PRPGVVLLTF RDKEICADPR VPWVKMILNK LSQ (SEQ ID NO:8).

For example, the amino acid sequence of EAW82918 is as follows (with the signal peptide at residues 1-24): MARLQTALLV VLVLLAVALQ ATEAGPYGAN MEDSVCCRDY VRYRLPLRVV KHFYWTSDSC PRPGVVLLTF RDKEICADPR VPWVKMILNK LSQ (SEQ ID NO:9).

For example, the amino acid sequence of O00626 is as follows (with the signal peptide at residues 1-24): MDRLQTALLV VLVLLAVALQ ATEAGPYGAN MEDSVCCRDY VRYRLPLRVV KHFYWTSDSC PRPGVVLLTF RDKEICADPR VPWVKMILNK LSQ (SEQ ID NO:10).

MDC detection encompasses detection of full-length MDC, as well as detection of naturally-occurring fragments or other metabolites of MDC found in a biological sample and detection of fragments or other derivatives generated by manipulation of a biological sample, with the proviso that detection of such fragments, metabolites, or derivatives is specific for detection of MDC. MDC fragments are usually at least 10, 15, 20, 25, 30, 35, 40, 45, 50, 55, or 60 amino acids or more in length. MDC detection can also be accomplished by detecting nucleic acid encoding MDC (e.g., RNA encoding MDC or DNA generated from such MDC-encoding RNA, e.g., using RT-PCR). MDC detection can involve direct detection of MDC or a fragment thereof found in a biological sample, or indirect detection (e.g., by detecting binding of an anti-MDC binding partner, e.g., an anti-MDC antibody).

According to certain embodiments, MDC detection (e.g., serum MDC detection) involves binding of an anti-MCD antibody to MDC. Aspects of these embodiments may include binding a detectably-labeled anti-MDC antibody to MDC, such that detecting MDC involves detecting the detectable label of the anti-MDC antibody bound to MDC. Other aspects of these embodiments may include binding an anti-MDC antibody to MDC, followed by binding a detectably-labeled secondary antibody to the anti-MDC antibody, such that detecting MDC involves detecting the detectable label of the secondary antibody. The anti-MDC antibody may be any antibody that specifically binds to MDC. According to certain aspects, the anti-MDC antibody is a commercially available anti-MDC antibody, such as a monoclonal or polyclonal anti-MDC antibody available from Abcam®, Santa Cruz Biotechnology®, United States Biological, R&D Systems®, Lifespan Biosciences, Meso Scale Discovery®, or any other commercially available antibody. In certain aspects, the anti-MDC antibody is commercially available as part of a kit, such as a kit for solution phase- or solid phase- (e.g., ELISA-) based detection of MDC alone, or in combination with any other biomarkers of interest, e.g., eotaxin-1 (E1), eotaxin-3 (E3), Interleukin-15 (IL-15), alkaline phosphatase (AP), or any combination thereof.

In certain aspects, the MDC present in a sample of interest is directly or indirectly immobilized to a surface, followed by binding of MDC with a detectably-labeled primary anti-MDC antibody, or binding of MDC by an unlabeled primary antibody, which is in turn bound by a detectably-labeled secondary antibody. Any suitable strategy for immobilizing MDC to a surface may be employed. In certain aspects, an anti-MDC "capture" antibody attached to a surface binds the MDC present in the sample of interest, thereby indirectly immobilizing MDC to the surface. In other aspects, a receptor specific for MDC attached to a surface binds the MDC present in the sample of interest, thereby indirectly immobilizing MDC to the surface. Once immobilized, the MDC may be subsequently detected using any convenient approach, such as solid-phase antibody-based detection, e.g., using a detectably-labeled anti-MDC primary antibody, or an unlabeled anti-MDC primary antibody and a detectably-labeled secondary antibody that binds the primary antibody.

IL-15

"Interleukin-15" or "IL-15" refers to a polypeptide of the interleukin family. IL-15 is produced as prepolypeptide comprising a signal peptide that is cleaved to generate a mature polypeptide. Examples of human IL-15 include those comprising an acid sequence of Accession No. P40933; NP_000576; NP_751915; and naturally-occurring variants thereof.

For example, the amino acid sequence of P40933 is as follows (with the signal peptide at residues 1-23): MRISKPHLRS ISIQCYLCLL LNSHFLTEAG IHVFILGCFS AGLPKTEANW VNVISDLKKI EDLIQSMHID ATLYTESDVH PSCKVTAMKC FLLELQVISL ESGDASIHDT VENLIILANN SLSSNGNVTE SGCKECEELE EKNIKEFLQS FVHIVQMFIN TS (SEQ ID NO: 11).

For example, the amino acid sequence of NP_000576 is as follows (with the signal peptide at residues 1-29): MRISKPHLRS ISIQCYLCLL LNSHFLTEAG IHVFILGCFS AGLPKTEANW VNVISDLKKI EDLIQSMHID ATLYTESDVH PSCKVTAMKC FLLELQVISL ESGDASIHDT VENLIILANN SLSSNGNVTE SGCKECEELE EKNIKEFLQS FVHIVQMFIN TS (SEQ ID NO:12).

For example, the amino acid sequence of NP_751915 is as follows (with the signal peptide at residues 1-23): MVLGTIDLCS CFSAGLPKTE ANWVNVISDL KKIEDLIQSM HIDATLYTES DVHPSCKVTA MKCFLLELQV ISLESGDASI HDTVENLIIL ANNSLSSNGN VTESGCKECE ELEEKNIKEF LQSFVHIVQM FINTS (SEQ ID NO: 13).

IL-15 detection encompasses detection of full-length IL-15, as well as detection of naturally-occurring fragments or other metabolites of IL-15 found in a biological sample, and detection of fragments or other derivatives generated by manipulation of a biological sample, with the proviso that detection of such fragments, metabolites, or derivatives is specific for detection of IL-15. IL-15 fragments are usually at least 10, 15, 20, 25, 30, 35, 40, 45, 50, 55, 60, 65, or 70 amino acids or more in length. IL-15 detection can also be accomplished by detecting nucleic acid encoding IL-15 (e.g., RNA encoding E3 or DNA generated from such IL-15-encoding RNA, e.g., using RT-PCR). IL-15 detection can involve direct detection of IL-15 or a fragment thereof found in a biological sample, or indirect detection (e.g., by detecting binding of an anti-IL-15 binding partner, e.g., an anti-IL-15 antibody).

According to certain embodiments, IL-15 detection (e.g., serum IL-15 detection) involves binding of an anti-IL-15 antibody to IL-15. Aspects of these embodiments may include binding a detectably-labeled anti-IL-15 antibody to IL-15, such that detecting IL-15 involves detecting the detectable label of the anti-IL-15 antibody bound to IL-15. Other aspects of these embodiments may include binding an anti-IL-15 antibody to IL-15, followed by binding a detectably-labeled secondary antibody to the anti-IL-15 antibody, such that detecting IL-15 involves detecting the detectable label of the secondary antibody. The anti-IL-15 antibody may be any antibody that specifically binds to IL-15. According to certain aspects, the anti-IL-15 antibody is a commercially available anti-IL-15 antibody, such as a monoclonal or polyclonal anti-IL-15 antibody available from Abcam®, Abnova, Abgent, Santa Cruz Biotechnology®, United States Biological, ProSci, R&D Systems®, Fitzgerald, Lifespan Biosciences, Meso Scale Discovery®, or any other commercially available antibody. In certain aspects, the anti-IL-15 antibody is commercially available as part of a kit, such as a kit for solution phase- or solid phase- (e.g., ELISA-) based detection of IL-15 alone, or in combination with any other biomarkers of interest, e.g., eotaxin-1 (E1), eotaxin-3 (E3), Macrophage-Derived Chemokine (MDC), alkaline phosphatase (AP), or any combination thereof.

In certain aspects, the IL-15 present in a sample of interest is directly or indirectly immobilized to a surface, followed by binding of IL-15 with a detectably-labeled primary anti-IL-15 antibody, or binding of IL-15 by an unlabeled primary antibody, which is in turn bound by a detectably-labeled secondary antibody. Any suitable strategy for immobilizing IL-15 to a surface may be employed. In certain aspects, an anti-IL-15 "capture" antibody attached to a surface binds the IL-15 present in the sample of interest, thereby indirectly immobilizing IL-15 to the surface. In other aspects, a receptor specific for IL-15 attached to a surface binds the IL-15 present in the sample of interest, thereby indirectly immobilizing IL-15 to the surface. Once immobilized, the IL-15 may be subsequently detected using any convenient approach, such as solid-phase antibody-based detection, e.g., using a detectably-labeled anti-IL-15 primary antibody, or an unlabeled anti-IL-15 primary antibody and a detectably-labeled secondary antibody that binds the primary antibody.

Alkaline Phosphatase (AP)

"Alkaline phosphatase" (or "AP" or "ALP") refers to an enzyme present in all tissues throughout the entire human body, but is particularly concentrated in liver, bile duct, kidney, bone, and the placenta. Humans contain the following alkaline phosphatase isozymes: ALPI (an isozyme found in the intestine); ALPL (a tissue non-specific isozyme found primarily in liver, bone, and kidney); and ALPP (an isozyme found primarily in the placenta).

AP detection can involve direct detection of AP or a fragment thereof found in a biological sample, or indirect detection (e.g., by detecting AP enzymatic activity in a sample, or by binding of an anti-AP binding partner, e.g., an anti-AP antibody). Where the biological sample is a blood sample (e.g., whole blood, blood fraction (e.g., serum, plasma)), detection of AP levels by assaying for enzymatic activity of AP is of particular interest, e.g., using commercially available assay methods and reagents.

Direct detection of AP can encompass detection of full-length AP, as well as detection of naturally-occurring fragments or other metabolites of AP found in a biological sample, and detection of fragments or other derivatives generated by manipulation of a biological sample, with the proviso that detection of such fragments, metabolites, or derivatives is specific for detection of AP. AP fragments are usually at least 10, 15, 20, 25, 30, 35, 40, 45, 50, 55, or 60 amino acids or more in length. AP detection can also be accomplished by detecting nucleic acid encoding AP (e.g., RNA encoding AP or DNA generated from such AP-encoding RNA, e.g., using reverse transcriptase-PCR (RT-PCR)).

According to certain embodiments, AP detection (e.g., serum AP detection) involves binding of an anti-AP antibody to AP. Aspects of these embodiments may include binding a detectably-labeled anti-AP antibody to AP, such that detecting AP involves detecting the detectable label of the anti-AP antibody bound to AP. Other aspects of these embodiments may include binding an anti-AP antibody to AP, followed by binding a detectably-labeled secondary antibody to the anti-AP antibody, such that detecting AP involves detecting the detectable label of the secondary antibody. The anti-AP antibody may be any antibody that specifically binds to AP. According to certain aspects, the anti-AP antibody is a commercially available anti-AP antibody, such as a monoclonal or polyclonal anti-AP antibody available from Abcam®, Abgent, Santa Cruz Biotechnology®, ProSci, Fitzgerald, Lifespan Biosciences, Meso Scale Discovery®, or any other commercially available antibody. In certain aspects, the anti-AP antibody is commercially available as part of a kit, such as a kit for solution phase- or solid phase- (e.g., ELISA-) based detection of AP alone, or in combination with any other biomarkers of interest, e.g., eotaxin-1 (E1), eotaxin-3 (E3), Macrophage-Derived Chemokine (MDC), interleukin-15 (IL-15), or any combination thereof.

In certain aspects, detection of AP involves immobilizing AP to a surface, followed by binding of AP with a detectably-labeled primary anti-AP antibody, or binding of AP by an unlabeled primary antibody, which is in turn bound by a detectably-labeled secondary antibody. Any suitable strategy for directly or indirectly immobilizing AP to a surface may be employed. In certain aspects, an AP "capture" antibody attached to a surface binds the AP present in the sample of interest, thereby indirectly immobilizing AP to the surface. In other aspects, a receptor specific for AP attached to a surface binds the AP present in the sample of interest, thereby indirectly immobilizing AP to the surface. Once immobilized, the AP may be subsequently detected using any convenient approach, such as solid-phase antibody-based detection, e.g., using a detectably-labeled anti-AP primary antibody, or an unlabeled anti-AP primary antibody and a detectably-labeled secondary antibody that binds the primary antibody.

According to certain embodiments, detection of AP is based on detecting the enzymatic activity of AP. For example, the phosphatase activity of AP present in a biological fluid or tissue of interest may be assayed by contacting the AP with a suitable AP substrate (e.g., p-nitrophenyl phosphate or other suitable substrate), followed by detection/quantitation of a detectable change resulting from AP-mediated dephosphorylation of the substrate (e.g., a color change when the assay employed is a colorimetric assay).

Subjects

The methods of the present disclosure can be used to facilitate a diagnosis of a liver disease, e.g., an inflammatory liver disease, e.g., one or more of AIH, PBC, and PSC, in any suitable subject. In certain aspects, the subject has, is suspected of having, or at risk of having, an inflammatory liver disease, and includes subjects having, suspected of having, or at risk of having a liver disease of one or more of AIH, PBC, and PSC. Such subjects include patients undergoing therapy, e.g., undergoing therapy to treat a suspected or diagnosed inflammatory liver disease or undergoing therapy which places the subject at risk of an inflammatory liver disease, e.g., a liver disease of one or more of AIH, PBC and PSC.

According to certain embodiments, subjects to be tested using a method of the present disclosure include individuals who present with or have presented with one or more symptoms of a liver disease, e.g., an inflammatory liver disease, and includes individuals who present with or have presented with symptoms associated with one or more of AIH, PBC, and PSC, including symptoms of a overlap syndrome of one or more of AIH, PBC, and PSC. Examples of such symptoms include any symptoms indicative of a liver disease such as fatigue, right upper quadrant (RUQ) abdominal pain, nausea, pruritus, jaundice, and/or any abnormal levels of liver enzymes.

Subjects at risk of a liver disease of one or more of AIH, PBC and PSC include those with IBD or a family history of IBD, an autoimmune disease, AIH, PBC, and/or PSC.

A subject can be male or female, and may or may not have any prior history of liver disease. In some instances, the subject does may or may not have viral hepatitis (e.g., HCV), or may be suspected of having a viral hepatitis (e.g., HCV). In some instances, the subject is one which has a negative diagnosis for pathogen-induced hepatitis (e.g., a negative diagnosis for viral hepatitis (e.g., hepatitis caused by infection by hepatitis A, B, C, D, or E; Epstein-Barr virus (EBV), cytomegalovirus (CMV)), a negative diagnosis for alcohol-induced liver disease, and/or a negative diagnosis for a drug-induced liver disease.

In certain aspects, the methods of the present disclosure are used to diagnosis a liver disease (e.g., an inflammatory liver disease, such as one or more of AIH, PBC and PSC) in subjects that are not suspected of having a liver disease. For example, the methods of the present disclosure may be used to diagnose a liver disease in a subject who exhibits no apparent clinical symptoms of liver disease (e.g., an apparently healthy subject). Such subjects may exhibit no morbidity at all (e.g., a subject undergoing a routine medical screening (or "check-up")). As such, in certain aspects, the methods find use in diagnosing a subject with liver disease prior to the subject exhibiting any outward manifestations of liver disease. In other aspects, the methods of the present disclosure are used to diagnosis a liver disease in a subject who presents with an unspecified morbidity, e.g., a morbidity that may be attributable to a number of etiologies, where liver disease is only one of such etiologies.

Biological Samples

Suitable biological samples useful in the methods of the present disclosure include biological fluids (e.g., a blood sample, e.g., whole blood, blood fraction (e.g., serum, plasma)), and other liquid samples of biological origin, as well as solid tissue samples such as a liver biopsy specimen. Where the biological sample is a blood sample, the blood sample can be obtained from fresh blood or stored blood (e.g. in a blood bank). The biological sample can be a blood sample expressly obtained for an assay of the present disclosure or a blood sample obtained for another purpose which can be subsampled for an assay of the present disclosure.

In certain aspects, the biological sample is a tissue section (e.g., a liver biopsy section or other section of interest), where one or more of E3, E1, MDC, IL-15 and AP are detected in the section by immunohistochemical (e.g., immunofluorescence) staining, or based on in situ enzymatic activity of the biomarker (e.g., phosphatase activity of AP). In other aspects, the biological sample is a tissue homogenate in which the biomarker(s) of interest is detected.

Samples can be manipulated after procurement, such as by treatment with reagents, solubilization, and/or enrichment for certain components for an analyte (s) to be assayed. Samples can be pretreated as necessary by dilution in an appropriate buffer solution, concentrated if desired, or fractionated by any number of methods including but not limited to ultracentrifugation, fractionation by fast performance liquid chromatography (FPLC), or precipitation. Any of a number of standard aqueous buffer solutions, employing one of a variety of buffers, such as phosphate, Tris, or the like, at physiological pH can be used. In general, after isolation, samples (such as blood samples) are stored at −80° C. until assaying.

Assay Formats and Detection Methods

Biomarkers for analysis in connection with the methods of the present disclosure (e.g., E3, E1, MDC, IL-15, and/or AP) can be detected using a variety of methods, with methods suitable for quantitative and semi-quantitative assays being of particular interest. Assays can be selected according to the form of the biomarker to be tested (e.g., polypeptide versus nucleic acid). Examples of detection methods include, but are not limited to, methods for detection of a biomarker polypeptide by binding to a specific binding partner (e.g., antibody) (e.g., ELISA (e.g., non-multiplex, multiplex (e.g., LUMINEX®, MESO DISCOVERY®), flow cytometry and the like), mass spectrometric methods, mass spectrophotometry, HPLC, gas chromatography, cytokine/chemokine arrays (e.g., using nucleic acid or cytokine/chemokine binding partners), NMR, TMA assay, and various assays involving reverse transcription of RNA and nucleic acid amplification (e.g., PCR, quantitative real time PCR, nucleic acid microarrays, and the like).

The following are examples of materials and assay formats for use in the methods of the present disclosure.

Methods for Detection of Polypeptides Using Biomarker Binding Reagents

The methods of the present disclosure can be conducted using binding reagents that bind a biomarker polypeptide, e.g., an anti-biomarker antibody; a binding reagent comprising a ligand-binding portion of a receptor for the biomarker polypeptide, and the like. Where antibodies are used, such methods may be generally referred to as immunoassays, which, can be conducted in a variety of different formats, some of which are provided below as examples.

The ordinarily skilled artisan will appreciate that any suitable binding reagent can be used in the biomarker polypeptide detection methods of the present disclosure. For example, a binding reagent that comprises a receptor, or at least a ligand-binding portion of a receptor, for a biomarker polypeptide can be used in lieu of an antibody in immunoassays. Receptors and ligand-binding portions of receptors for biomarkers are available and known in the art. For example, receptors that bind E1 include CCR1, CCR2, CCR3, and CCR5; receptors that bind E3 include CCR1, CCR2, CCR5, and CX3CR1; MDC binds the CCR4 receptor; and IL-15 binds the IL-15 receptor (e.g., IL-15Rα). It should be understood that the biomarker polypeptide detection methods may be described herein with reference to antibodies and "immunoassays", but such references are solely for purposes of brevity and clarity, and is not meant to be limiting.

It will be appreciated that any suitable binding partner can be used in lieu of an antibody in immunological methods available in the art, with the proviso that the assay design is such that the desired specificity of detection of the biomarker is adequately preserved. For example, a binding partner in the form of a receptor or ligand-binding portion thereof can be used as a capture reagent. In such an embodiment, binding of the biomarker to the binding partner can be detected using, for example, an antibody specific for the biomarker to detecting binding partner-biomarker complexes. In another example, a binding partner in the form of a receptor or ligand-binding portion thereof can be used as a detection reagent to detect, for example, biomarker in a complex with a specific anti-biomarker antibody/biomarker complex.

Assays involving use of a biomarker polypeptide and a binding reagent generally involve the detection of binding between a binding reagent (e.g., an anti-biomarker antibody (e.g., an anti-E3, anti-E1, anti-MDC, anti-IL-15, and/or AP antibody that specifically binds its respective target antigen)) and its target biomarker polypeptide (e.g., E3, E1, MDC, IL-15, and AP respectively) in a biological sample obtained from a patient.

Antibodies suitable for use in the methods of the present disclosure in accordance with the methods of the present disclosure include those that bind any suitable region of a biomarker. Antibodies useful in biomarker detection methods can be polyclonal or monoclonal antibodies. For example, assays can use polyclonal antibodies as a capture reagent and monoclonal antibodies as a detection reagent, or vice versa. Antibodies may be of any origin, e.g., mammalian (mouse, goat, rat, and the like), non-mammalian (e.g., avian, e.g., chicken), and may have been produced by any method or combination of methods (e.g., immunization of a host (e.g., a non-human animal), isolation as polyclonal sera, hybridoma-expressing monoclonal antibody, recombination production, and the like).

Assays can be conducted in any of a variety of formats, and may be performed quantitatively or semi-quantitatively. In general, the assay will measure specific binding between a biomarker binding reagent (e.g., an anti-biomarker antibody) and a patient sample by detection of the presence or absence of complex (e.g., an immunocomplex) of the anti-biomarker binding reagent (e.g., antibody) and the biomarker. Examples of immunological methods include, e.g., enzyme-linked immunosorbant assay (ELISA), radioimmunoassay (RIA), and the like. Such immunological methods can be readily adapted for use with a polypeptide comprising at least a ligand binding portion of a biomarker receptor.

Assays can be performed by first immobilizing either proteins from a test sample, or anti-biomarker binding reagents (e.g., anti-biomarker antibodies), on a surface of an insoluble support. Suitable supports are well known in the art and include, for example, immunoaffinity column materials, polystyrene beads, latex beads, magnetic beads, colloid metal particles, glass and/or silicon chips and surfaces, nitrocellulose strips, nylon membranes, wells of assay plate (e.g., multi-well plates), test strips, plastic tubes, etc. An insoluble support can comprise any of a variety of substances, including, e.g., glass, polystyrene, polyvinyl chloride, polypropylene, polyethylene, polycarbonate, dextran, nylon, amylose, natural and modified celluloses, polyacrylamides, and agaroses.

Binding to the support may be accomplished by any suitable means, depending upon the nature of the surface, either directly or indirectly, and may be either covalently or non-covalently bound, e.g., binding by ionic, hydrophobic, and/or covalent interactions. The particular manner of binding is not crucial so long as it is compatible with the reagents and overall detection methods. Where the anti-biomarker binding reagents (e.g., antibodies) are bound to the support and the assay is to detect more than one biomarker in the sample in a single reaction mixture, it may be desirable to bind the binding reagents (e.g., anti-biomarker antibodies) for the different biomarkers to be detected to discrete and separate locations on the support so that the presence of absence of biomarker-binding reagent (e.g., antigen-antibody) complexes at the different locations can be correlated with the presence or absence of the corresponding biomarker in the sample. Assays in which more than one biomarker is detected from the same sample in a single reaction mixture are often referred to as "multiplex assays.

The insoluble supports can be of any suitable material which is readily separated from soluble material, and which is otherwise compatible with the overall method of detecting a biomarker in a sample. The surface of such supports may be solid or porous and of any convenient shape. Examples of suitable insoluble supports to which the receptor is bound include beads, e.g. magnetic beads, latex particles, membranes and microtiter well surfaces.

Before contacting samples or fractions thereof to the assay support, it may be desirable to block non-specific binding sites on the insoluble support so as to reduce non-specific binding of sample or other reaction mixture components to sites on the support not occupied by polypeptide or antibody. Examples of blocking agents include non-interfering proteins such as bovine serum albumin, casein (or other milk proteins), gelatin, and the like. Alternatively, several detergents at non-interfering concentrations, such as Tween, NP40, TX100, and the like may be used.

Samples, fractions or aliquots thereof can be added to separate supports or to a single support with discrete, separately assayable locations to which anti-biomarker antibodies or are bound (e.g., as in an array). The assay can include a series of suitable standards, e.g., a reagent for detection of a biomarker that serves as an internal control (which internal control may be present in the biological sample as obtained from the subject or spiked to include a known amount of the control), a separately assayed sample containing a known concentration of one or more biomarkers, and the like. Controls can be positive controls or negative controls. Where desired, multiple samples and standards can be assayed so that mean values can be obtained for each.

The support having bound test sample (or bound anti-biomarker binding reagents) is incubated with the anti-biomarker binding reagent (or with test sample, where the support has bound anti-biomarker binding reagents) for a time sufficient for formation of specific biomarker-binding reagent complexes (e.g., antigen-antibody complexes). After incubation, the insoluble support can be washed of non-bound components. For example, the support can be washed with a dilute non-ionic detergent medium at an appropriate pH, generally 7-8. Washing can be repeated as desired so as to provide for removal of non-specifically bound proteins to an acceptable level.

After washing, the presence or absence of specific biomarker-binding reagent (e.g., antigen-antibody complexes (also referred to as "specific immunocomplexes" or "specific immune complexes")) is detected. Where the test sample is bound to the support, the presence or absence of specific complexes can be detected directly, e.g., by detection of a detectable label on the anti-biomarker binding reagent. Where the binding reagent is not detectably labeled and the assay involves immobilized test sample, specific complexes can be detected by contacting the sample with a solution containing a detection reagent, e.g., an antibody-specific detection reagent to detect antibody bound to immobilized test protein (e.g., a secondary antibody (i.e., an anti-antibody)). The detection reagent may be any compound that binds a binding reagent (e.g., antibody) with sufficient specificity such that the bound binding reagent is distinguished from other components present. For example, detection reagents can be antibodies specific for the anti-biomarker binding reagent (e.g., biomarker receptor, antibody). Where the detection reagent is an antibody, the antibody may be a monoclonal antibody or polyclonal sera, e.g. goat anti-mouse antibody, rabbit anti-mouse antibody, etc.

The detection reagent can be labeled to facilitate direct, or indirect detection of binding. Suitable detectable labels include any composition detectable by spectroscopic, photochemical, biochemical, immunochemical, electrical, optical or chemical means. Examples include, but are not limited to, magnetic beads, fluorescent dyes (e.g., fluorescein isothiocyanate, texas red, rhodamine, a green fluorescent protein, a red fluorescent protein, a yellow fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. multistyrene, multipropylene, latex, etc.) beads. Examples of labels which permit indirect measurement of binding include enzymes where the substrate may provide for a colored or fluorescent product. For example, the detection reagent can be an antibody labeled with a covalently bound enzyme capable of providing a detectable product signal after addition of suitable substrate. Examples of suitable enzymes for use in conjugates include horseradish peroxidase, alkaline phosphatase, maleate dehydrogenase and the like. Where not commercially available, such antibody-enzyme conjugates are readily produced by techniques known to those skilled in the art.

Alternatively, the detection reagent may be unlabeled. In this case, a labeled second detection reagent specific for the first detection reagent is used, where the second detection reagent can be labeled in any of the above manners. Such compounds can be selected such that multiple compounds bind each molecule of bound second receptor. Examples of second detection reagent/first detection reagent-specific pairs include antibody/anti-antibody and avidin (or streptavidin)/biotin. Since the resultant signal is thus amplified, this technique may find particular use where only a small amount of biomarker may be present, or where the background measurement (e.g., non-specific binding) is unacceptably high. An example is the use of a labeled antibody specific to the first detection reagent.

Where the anti-biomarker binding reagent (e.g., antibody) is bound to the support, formation of specific complexes can be accomplished using an antibody to detect the presence or absence of specific biomarker-binding reagent complexes. The detection antibody can be the same or different from the bound antibody, with the proviso that the epitopes to which the detection antibody binds are available for detection antibody binding when the biomarker is in the complex with the bound anti-biomarker binding reagent. As described above, the detection antibody can be labeled or unlabeled, and the formation of specific complexes of bound anti-biomarker binding reagent-biomarker-detection antibody detected directly (e.g., by virtue of the detectable label on the detection antibody) or indirectly (e.g., by use of a third reagent that detects the detection antibody in the complex).

After incubation with the reagents for a time sufficient to allow binding of specific complexes, the insoluble support can again be washed to reduce non-specifically bound detection reagent(s). After washing, the signal produced by the bound conjugate is detected by any suitable means compatible with the assay format. For example, where an enzyme conjugate is used, an appropriate enzyme substrate is provided so a detectable product is formed. For example, where the detection involves peroxidase in an enzyme conjugate, the substrate is usually a combination of hydrogen peroxide and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art.

The presence or absence binding of anti-biomarker binding reagent (e.g., antibody) binding may be determined by various methods that are compatible with the detectable label used, e.g., microscopy, radiography, scintillation counting, etc. Generally a level of specific binding reagent-biomarker complexes is compared to a level of one or more control samples, and the results evaluated to facilitate a diagnosis. Control samples can be run in parallel to provide comparison levels, or the levels of specific complexes in a control level provided as standard values for purposes of comparison.

The assays described here can take a variety of forms. Exemplary formats include, but are not limited to, competitive binding assays, in which formation of complexes is performed in the presence of different amounts of a competitor protein which competes for binding to the anti-biomarker binding reagent (e.g., antibody). The competitor molecule can be labeled and detected as previously described, where a decrease in competitor binding will be proportional to the level of biomarker present in the sample.

The detection assays can be carried out in solution. For example, the anti-biomarker antibody(ies) can be combined with the test sample (e.g., serum or any other test sample of interest), and immune complexes of anti-biomarker antibody (ies) and biomarker(s) are detected.

Mass Spectrometric Methods

The methods of the present disclosure can be accomplished by other detection techniques. For example, mass spectrometric assays can be adapted for detection of biomarker(s) in a biological sample. Mass spectrometry-based methods exploit the differences in mass of biomarkers to facilitate detection. Mass spectrometry can be combined with immunoassays, e.g., by first forming specific biomarker-antibody immunocomplexes, and detecting the presence or absence of the specific immunocomplexes by mass spectroscopy. For example, an anti-biomarker antibody can be used to capture the biomarker of interest (e.g., E3, E1, MDC, and/or IL-15). The anti-biomarker antibody can be bound to a support, such as a bead, a plate, a membrane or a chip. After unbound materials are washed away, the captured biomarkers can be detected by mass spectrometry. Examples of mass spectrometers are time-of-flight, magnetic sector, quadmpole filter, ion trap, ion cyclotron resonance, electrostatic sector analyzer and hybrids of these.

Analysis of mass spectrometry data can be accomplished by available methods. For example, assaying of analytes by time-of-flight mass spectrometry generates a time-of-flight ("TOF") spectrum. The TOF spectrum ultimately analyzed typically generally does not represent the signal from a single pulse of ionizing energy against a sample, but rather the sum of signals from a number of pulses. This reduces noise and increases dynamic range. This TOF data can then be subjected to data processing. For example, in Ciphergen's PROTEINCHIP® software, data processing typically includes TOF-to-M/Z transformation to generate a mass spectrum, baseline subtraction to eliminate instrument offsets and high frequency noise filtering to reduce high frequency noise.

Data generated by mass spectrometry methods can be analyzed with the use of a programmable computer. The computer program executes a program to analyze the data to indicate the number of biomarkers detected, and the strength of the signal (indicative of the amount of the biomarker), and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's PROTEINCHIP® software package, that can automate the detection of peaks. In general, this software functions by identifying signals having a signal-to-noise ratio above a selected threshold and labeling the mass of the peak at the centroid of the peak signal. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

Detection of Biomarker-Encoding Nucleic Acid

Biomarker detection can also be accomplished by detecting biomarker-encoding nucleic acid so as to assess biomarker expression levels. Methods for detection of expression levels of a target sequence of interest are known in the art, and can be readily adapted to the methods of the present disclosure to detection expression levels of E1, E3, MDC, IL-15 and/or AP.

For example, isolated mRNA from a biological sample can be used in hybridization or amplification assays that include, but are not limited to, Southern or Northern analyses, polymerase chain reaction (PCR) analyses and probe arrays. One method for the detection of mRNA levels involves contacting the isolated mRNA with a nucleic acid molecule (probe) that can hybridize to biomarker-encoding nucleic acid (e.g., mRNA or DNA produced by PCR amplification of such mRNA). The nucleic acid probe can be for example, a full-length cDNA, or a portion thereof, such as an oligonucleotide of at least 7, 15, 30, 50, 100, 250 or 500 nucleotides in length and sufficient to specifically hybridize under stringent conditions to biomarker-encoding nucleic acid.

In one embodiment, the mRNA from a biological sample is immobilized on a solid surface and contacted with a probe. In an alternative embodiment, the probe(s) are immobilized on a solid surface and the mRNA isolated from the biological sample is contacted with the probe(s), e.g., as in an array format.

Methods of detecting levels of biomarker expression in a sample can involve any suitable method of nucleic acid amplification, e.g., by RT-PCR, ligase chain reaction, or any other nucleic acid amplification method, followed by the detection of the amplified molecules using techniques well known to those of skill in the art. In one example, biomarker expression is assessed by quantitative fluorogenic RT-PCR (e.g., such as using TaqMan™). Such methods typically utilize pairs of oligonucleotide primers that are specific for a biomarker-encoding nucleic acid. Methods for designing oligonucleotide primers specific for a known sequence are well known in the art.

Microarrays can be used to detect biomarker expression. In such embodiments, microarrays having immobilized capture probes are provided on an array surface at addressable locations. RNA (or DNA produced by amplification of RNA) from a biological sample is hybridized to complementary probes on the array, and hybridized complexes detected. Hybridization intensities for each probe on the array are determined and can be converted to a value representing a relative gene expression level.

Compositions

The present disclosure provides compositions that find use, e.g., in practicing the methods of the present disclosure. In certain aspects, the compositions include an agent for detecting a biomarker of interest (e.g., an E3, E1, MDC, IL-15 or AP detection agent). With respect to E3, for example, the detection agent may be any agent useful for detecting E3 in a sample of interest (e.g., a serum sample of a subject suspected of having liver disease), including but not limited to, an anti-E3 antibody, a primer pair for amplifying an E3-encoding nucleic acid (e.g., in a quantitative PCR assay), a detectable agent that hybridizes to E3 (e.g., a probe), or the like. In certain aspects, the composition includes a nucleic acid extract from a biological sample of interest, such as a nucleic acid extract from a liver biopsy sample, peripheral blood mononuclear cells (PBMCs), peripheral blood lymphocytes (PBLs), a whole blood sample, serum, or plasma. Such compositions find use, e.g., in nucleic acid amplification assays, e.g., a PCR assay (e.g., a qPCR assay), a transcription-mediated amplification (TMA) assay, or other convenient nucleic acid amplification-based biomarker detection assay, as well as solution or solid-phase nucleic acid hybridization assays (e.g., using a nucleic acid array). In addition to an E3 detection agent, compositions of the present disclosure may include one or more detection agents useful for detecting one or more additional biomarkers of interest. Such additional detection agents may include, but are not limited to, one or more agents (e.g., an antibody or primer pair) for detecting eotaxin-1 (E1), macrophage-derived chemokine (MDC), interleukin-15 (IL-15), alkaline phosphatase (AP), or any combination thereof. For example, the compositions may include an E3 detection agent and an E1 detection agent; or an E3 detection agent, an E1 detection agent, and an MDC detection agent; or an E3 detection agent, an E1 detection agent, an MDC detection agent, and an IL-15 detection agent; or an E3 detection agent, an E1 detection agent, an MDC detection agent, an IL-15 detection agent, and an AP detection agent.

According to certain embodiments, the composition does not include any detection agents other than, optionally, a detection agent for detecting a control (e.g., "housekeeping") protein or nucleic acid to facilitate and control for quantitation of biomarker signals in addition to: an E3 detection agent; or an E3 detection agent and an E1 detection agent; or an E3 detection agent, an E1 detection agent, and an MDC detection agent; or an E3 detection agent, an E1 detection agent, an MDC detection agent, and an IL-15 detection agent; or an E3 detection agent, an E1 detection agent, an MDC detection agent, an IL-15 detection agent, and an AP detection agent.

The compositions of the present disclosure may include a biological sample from a subject (e.g., a subject suspected of having liver disease, an apparently healthy subject undergoing routine medical screening, a subject with an unspecified morbidity under investigation, a control subject, or other subject) or a control sample (e.g., serum, buffer, or the like in which one or more biomarkers of interest are present (e.g., added) for purposes of providing a control (e.g., a benchmark control that includes serum from a healthy individual spiked with each of the biomarkers to be detected in the assay) for the assay). For example, in certain aspects, the compositions include an E3 detection reagent (e.g., an anti-E3 antibody) and a serum sample, a plasma sample, or a whole blood sample from a subject suspected of having liver disease, e.g., a disease such as autoimmune hepatitis (AIH), primary sclerosing cholangitis (PSC), primary biliary cirrhosis (PBC), or any combination thereof. As described above, the compositions may further include one or more agents for detecting additional biomarkers of interest, such as detection agents useful for detecting E1, MDC, IL-15, AP, or any combination thereof.

In certain aspects, the compositions of the present disclosure are present in a container, such as a storage container and/or assay container. The container may be any convenient container convenient, e.g., for storing an E3 detection agent (e.g., in combination with one or more detection agents for detecting E1, MDC, IL-15, AP, or any combination thereof), or for carrying out a detection assay (e.g., a solution- or solid phase-based assay) for detecting E3 and any additional biomarker(s) of interest, such as E1, MDC, IL-15, AP, or any combination thereof. Containers of interest include a tube, e.g., a tube of any convenient size (e.g., ranging from 0.2 ml to 15 ml, such as 0.2 ml, 0.5 ml, 1.0 ml, 1.5 ml, 2.0 ml, 5 ml, 10 ml, 15 ml or the like) and material (e.g., polypropylene, or any other material suitable for storing or using the composition). In certain aspects, the composition is present in a container that is a series of tubes, such as a one- or two-dimensional array of tubes (e.g., a strip of tubes, or tubes in a "plate" format, such as a 24-well, 48-well, 96-well, 384-well, or other convenient plate format).

According to certain embodiments, the composition is disposed on a planar substrate (e.g., the bottom of a well, array, chip (e.g., microfluidic chip), and/or the like). When the composition is disposed on a substrate, any detection agents present in the composition (e.g., an E3 detection agent, optionally in combination with any one or more of an E1, MDC, IL-15, and/or AP detection agent) may be present in a solution or suspension disposed on the substrate, or alternatively, may be attached to the substrate, e.g., directly attached to the surface of the substrate, or attached via a linker moiety (e.g., an antibody (such as an anti-species antibody) or other suitable linker moiety). Such compositions find use, for example, in performing solid phase assays (e.g., ELISA-based or non-enzyme-based solid phase protein detection assays, solid-phase nucleic acid amplification, or the like) for detecting one or more biomarkers of interest.

Methods of Diagnosis of Inflammatory Liver Disease

The present disclosure provides methods for facilitating a diagnosis of a liver disease of one or more of autoimmune hepatitis (AIH), primary biliary cirrhosis (PBC), and primary sclerosing cholangitis (PSC). As described in more detail below, diagnosis can encompass one or more of 1) assessing whether the subject has a liver disease of one or more of AIH, PBC and PSC and differentiate the subject from a healthy or an HCV-infected individual; 2) assessing whether the individual has PSC (e.g., as opposed to one or both of AIH or PBC); and/or 3) assessing whether the individual has AIH (e.g., as opposed to one or both of PBC or PSC). These methods are described in more detail below.

In general, the methods comprise assaying a level of a biomarker (e.g., E3, E1, MDC and/or IL-15 and, optionally, AP) in a biological sample from the patient and comparing the test biomarker level to a control biomarker level. "Control biomarker level", which may also be referred to herein as a "cutoff value" or "biomarker threshold value", refers to a biomarker level that can be used to distinguish between a first condition and a second (e.g., between individuals who do not have a liver disease of at least one of AIH, PBC, and PSC and individuals who have such a liver disease) such that a biomarker level in a sample that is above a control level indicates an increased likelihood of the second condition in the individual. Thus, a "control biomarker level" or "biomarker threshold value" refers to an assay value (e.g., amount of a biomarker, ratio of biomarker amounts (e.g., as in E1/E3 ratio)), which is an approximate value that distinguishes the likelihood that a disease is present in the individual tested from the likelihood that a disease is not present in the individual tested, with a pre-selected specificity and/or sensitivity.

As illustrated in the Examples below, because HCV infection did not necessarily or significantly compromise the sensitivity and/or specification of the assays of the present disclosure, individuals used to define a control biomarker levels can be healthy individuals, HCV-infected individuals, or a combination of both.

For example, the control biomarker level can be a level of the biomarker in a healthy individual or, where the assay is to facilitate a diagnosis between AIH, PBC, and PSC, the control biomarker level can be a biomarker level associated with a liver disease (e.g. a level of E3 associated with AIH, PBC and/or PSC; a level of AP associated with liver disease (e.g., with PSC); a level of MDC associated with PBC to facilitate a differential diagnosis between PSC and AIH or PBC; or a level of IL-15 associated with PSC to facilitate a differential diagnosis between AIH and PBC or PSC).

For example, a biomarker threshold value can represent an approximate level of a biomarker that detects affected subjects at a desired sensitivity (e.g., at least 55%, at least about 60%, at least 70%, or at least 80% or more). Thus, for example, an individual having a biomarker level that is greater than a threshold value has at least about 60% or greater likelihood of having a positive diagnosis for that disease.

It will be appreciated that the precise number value for control or threshold values can vary with the type of assay and reagents used to detect the biomarkers. For example, the assay values upon which the control values for E3, E1 and E3 ratio, MDC, IL-15, and AP described herein are based on assay values obtained using serum samples and a multiplex ELISA kit from Meso Scale Discovery Company. However, regardless of the assay and reagents used, the correlations between a threshold or control value of a biomarker and likelihood of a disease state (e.g., one or more of AIH, PBC, and PSC; differential diagnosis of PSC against AIH and PBC; differential diagnosis of AIH against PSC and PBC) will be present regardless of the assays and reagents used. Thus, so long as the test samples are assayed for the biomarker (e.g., E1, E3, MDC, IL-15, AP) using an assay platform and reagents of the same general type (e.g., polypeptide assay, nucleic acid assay) and, generally preferably, same sensitivity as the assay platform and reagents used to determine the control/threshold values of the biomarker (E1, E3, MDC, IL-15, and AP, respectively), the findings upon which the methods of the present disclosure are based will be preserved.

Diagnosis of a Liver Disease of One or More of AIH, PBC and PSC

The present disclosure provides methods of assessing whether the subject has a liver disease of one or more of AIH, PBC and PSC. In general, this method comprises detecting a level of E3 in a biological sample from the patient.

The level of E3 can then be used to facilitate a diagnosis of one or more of AIH, PBC, and PSC by comparing the E3 level to a control E3 level. An E3 level in the sample that is greater than the control E3 level indicates an increased likelihood of a liver disease of at least one of AIH, PBC, and PSC in the patient. Methods involving assaying an E3 level can be used to facilitate a diagnosis in a subject who, for example, may present with one or more symptoms of a possible liver condition.

The control E3 level, which may also be referred to as an E3 threshold value or E3 cutoff value, can be determined as described herein, e.g., by assaying E3 levels in control populations and, through application of statistical analysis, identifying an E3 level that is present in at least 55%, at least about 60%, at least 70%, at least 80%, or at least 90% or more of patients having a liver disease of at least one of AIH, PBC, and/or PSC.

Values for control E3 levels can be readily determined using reagents and methods known in the art, and may vary with the assay used and the biological sample used. For example, where the assay is an immunoassay and the biological sample is serum, the control E3 level can be about 18-45 pg/ml serum, about 18-40 pg/ml serum, about 18-35 pg/ml serum, about 18-28 pg/ml serum, about 20-45 pg/ml serum, about 20-40 pg/ml serum, about 20-35 pg/ml serum, about 20-28 pg/ml serum, about 23-45 pg/ml serum, about 23-40 pg/ml serum, about 23-35 pg/ml serum, about 23-28 pg/ml serum, about 25-45 pg/ml serum, about 25-40 pg/ml serum, about 25-35 pg/ml serum, about 25-28 pg/ml serum, about 18 pg/ml serum, about 20 pg/ml serum, about 23 pg/ml serum, about 25 pg/ml serum, about 28 pg/ml serum, about 30 pg/ml serum, about 35 pg/ml serum, about 40 pg/ml serum, or about 45 pg/ml serum, such that a test E3 level that is greater than a control E3 level indicates a diagnosis of a liver disease of at least one of AIH, PSC, or PBC.

Assays and algorithms using E3 levels according to the present disclosure to facilitate a diagnosis of a liver disease of at least one of AIH, PSC or PBC with a desired sensitivity (e.g., at least 50%, at least 55%, at least 70%, at least 75%, at least 80%, at least 90%, at least 95% or greater), and with a desired specificity (e.g., at least 80%, at least 85%, at least 90%, at least 95% or greater).

Diagnosis of PSC

The methods of the present disclosure provide for assessing whether a subject (e.g., a subject suspected of having liver disease, an apparently healthy subject undergoing routine medical screening, a subject with an unspecified morbidity under investigation, or other subject of interest) has PSC, e.g., as a differential diagnosis against AIH and PBC, by assessing levels of E3, E1, MDC and IL-15 in a biological sample from the subject. The methods of the present disclosure also provide for facilitating a diagnosis of PSC in a subject suspected of having PSC (e.g., where a diagnosis of AIH and a diagnosis PBC have been excluded) by assessing a level of E3 and alkaline phosphatase (AP) in a biological sample from the subject. These methods are described in more detail below.

Methods of Diagnosing PSC

The methods of the present disclosure provide for assessing whether a subject (e.g., a subject suspected of having liver disease, an apparently healthy subject undergoing routine medical screening, a subject with an unspecified morbidity under investigation, or other subject of interest) has PSC, e.g., as a differential diagnosis against AIH and PBC, by assessing levels of E3, E1 and MDC in a biological sample from the subject. In such methods, a diagnosis of PSC in a subject suspected of having a liver disease is facilitated by detecting a level of E3, a level of E1, and a level of MDC in a biological sample from the subject. The E1 and E3 levels can be used to calculate a ratio of E1 and E3 levels. The ratio of E1 and E3 levels used in the algorithm can calculated as an E1/E3 ratio or as (E3/E1×100). Using the E3 level, the ratio of E1 and E3 levels (E1/E3 ratio or (E3/E1×100)), and the level of MDC, the method facilitates a diagnosis of PSC. This methods finds particular use in facilitating a differential diagnosis of PSC against both AIH and PBC as well as from healthy control and HCV-infected individuals. Where the E3 level that is greater than a control E3 level and the E1/E3 ratio that is greater than a control ratio of E1 and E3 (control E1/E3 ratio or control (E3/E1×100) value), and MDC level is greater than a control MDC level, an increased likelihood that the liver disease is PSC (and not PBC, AIH, HCV-infected or healthy individuals) is indicated. It should be understood that where the test E1 and E3 values as used to calculate the a ratio E1 and E3 levels as E3/E1, then the control value used is a control E3/E1 value, and where the test E1 and E3 values as used to calculate the a ratio E1 and E3 levels as (E1/E3×100), then the control value used is a control (E1/E3×100) value. For ease of reference, it should be understood that reference to a E3/E1 ratio or a control E3/E1 ratio is not meant to be limiting, but rather also contemplates the alternative use of a (E1/E3×100) or control (E1/E3×100) value, respectively. Thus, for example, reference throughout the specification to E3/E1 ratio also contemplates the alternate use of a (E1/E3×100) value.

The control E3 levels used to facilitate a diagnosis of PSC can be a control E3 level as described above in the context of an assay to facilitate a diagnosis of a liver disease of at least one of AIH, PBC, and PSC.

Control Ratios of E1 and E3 Levels

Values for control ratios of E1 and E3 levels, which may also be referred to as an E3/E1 ratio threshold value ((E1/E3×100) threshold value) or E3/E1 cutoff value ((E1/E3×100) cutoff value), can be determined as described herein, e.g., by assaying E3 levels and E1 levels in patient populations and, through application of statistical analysis, identifying a ratio of E1 and E3 levels that, when applied in an algorithm with a control E1 level and an control MDC level, identifies at least 55%, at least about 60%, at least 70%, or at least 80% or more of PSC patients in the population.

Values for control ratios of E1 and E3 can be readily determined using reagents and methods known in the art, and may vary with the assay used and the biological sample used. For example, where the assay is an immunoassay and the biological sample is serum, the control E1/E3 ratio can be about 10-25, about 10-20, about 15-20, about 15-25, about 10, about 15, about 20 or about 25. For example, where the assay is an immunoassay and the biological sample is serum, the control ((E1/E3×100) value can be about 5-8, about 5-7, or about 5, 6, or 7.

Control MDC Levels

The control MDC level can be an MDC threshold value. MDC threshold values can be determined as described herein, e.g., by assaying MDC levels in patient populations and, through application of statistical analysis, identifying an MDC level that is present in at least 60%, at least 70%, at least 80%, or at least 90% or more of patients having PSC as opposed to AIH or PBC. For example, where the assay is an immunoassay and the biological sample is serum, the MDC threshold value can be about 2,500 to 3,000 pg/ml serum, or about 2,800 pg/ml serum.

Values for control MDC levels, can be determined as described herein, e.g., by assaying MDC levels in patient populations and, through application of statistical analysis, identifying an MDC level that, when applied in an algorithm with a control E1 level, and control E1 and E3 levels ratio, identifies PSC patients in the population at a desired sensitivity (e.g., at least 55%, at least about 60%, at least 70%, or at least 80% or more).

Values for control MDC levels can be readily determined using reagents and methods known in the art, and may vary with the assay used and the biological sample used. For example, where the assay is an immunoassay and the biological sample is serum, the control MDC level can be about 2000 pg/ml-3000 pg/ml serum, about 2500 pg/ml-3000 pg/ml, about about 2800 pg/ml, or about 3000 pg/ml.

Assays and algorithms using E3 level, E1 and E3 levels ratio, and MDC level and according to the present disclosure can facilitate a diagnosis of PSC with a desired sensitivity (e.g., at least 50%, at least 55%, at least 70%, at least 75%, or at least 80% or greater, and with a specificity of at least 75%, at least 80%, at least 85%, at least 90%, at least 95% or greater) as compared to HCV-infected control, healthy controls, AIH affected and PBC affected subjects. Assays for using E3 level, E1 and E3 levels ratio, and MDC level and analysis according to the present disclosure can facilitate a differential diagnosis of PSC against AIH with a desired specificity (e.g., at least 75%, at least 80%, at least 85%, at least 90%, at least 95% or greater). Assays for using E3 level, E1 and E3 levels ratio, and MDC level and analysis according to the present disclosure can facilitate a differential diagnosis of PSC against PBC with a desired specificity (e.g., least 75%, at least 80%, at least 85%, at least 90%, or greater).

Algorithms for Detection of PSC Using E3, E1, and MDC Levels in a Subject Suspected of Having a Liver Disease of One or More of PSC, PBC and AIH The algorithm for analysis of test values of E3, E1 and MDC can use any of the control values discussed above, and may be generally described as follows:

$$(E3>X)+(E1/E3>Y)+(MDC>Z) \quad \text{(Algorithm I)}$$

Or $$(E3>X)+((E3/E1)\times 100)<Y')+(MDC>Z) \quad \text{(Algorithm I')}$$

wherein
X is an E3 control value;
Y is a control E1/E3 ratio value;
Y' is a control ((E3/E1)×100) value; and
Z is a control MDC value,
such that when test values of E3, E1 and MDC satisfy all elements of Algorithm I or of Algorithm I', there is an increased likelihood of PSC in the subject, and further an increased likelihood the subject has PSC as opposed to a AIH or PBC.

In one embodiment, the algorithm for analysis of test serum values of E3, E1 and MDC may be generally described as follows:

$$(E3>18\text{-}45 \text{ pg/ml})+(E1/E3>10\text{-}20)+(MDC>2000\text{-}3000 \text{ pg/ml}) \quad \text{(Algorithm Ia)}$$

Or $$(E3>18\text{-}45 \text{ pg/ml})+((E3/E1)\times 100)<6\text{-}7)+(MDC>2000\text{-}3000 \text{ pg/ml}) \quad \text{(Algorithm Ia')}$$

such that when test values of E3, E1 and MDC satisfy all elements of Algorithm I or of Algorithm I', there is an increased likelihood of PSC in the subject, and further an increased likelihood the subject has PSC as opposed to a AIH or PBC.

In one embodiment, method involves applying the E3 level, E1/E3 ratio and MDC level to an algorithm such that when:

$$(E3>28)+(E1/E3>15)+(MDC>2800) \quad \text{(Algorithm Ib)}$$

there is an increased likelihood of PSC in the subject, and further an increased likelihood the subject, and further an increased likelihood the subject has PSC as opposed to a AIH or PBC (values are calculated as pg/ml serum). As described below, using E3, E1 and MDC assay values in Algorithm Ib discriminated PSC from controls (which included HCV and healthy controls), PBC and AIH with a sensitivity of 65% to 67%, and a specificity of 92-98%.

In one embodiment, method involves applying the E3 level, E1/E3 ratio and MDC level to the following algorithm (values are calculated as pg/ml serum):

$$(E3>25)+(E1/E3>15)+(MDC>2800) \quad \text{(Algorithm Ic)}$$

there is an increased likelihood of PSC in the subject (as opposed to AIH or PBC) (values are calculated as pg/ml serum). As described below, using E3, E1 and MDC assay values in Algorithm Ic discriminated PSC from control (HCV and healthy controls), PBC, and AIH with a sensitivity of 72% to 75%, and a specificity of 92-96%.

Methods of Diagnosis of PSC in a Subject Suspected of Having PSC

The present disclosure provides methods for facilitating a diagnosis of PSC in a subject suspected of having PSC. Such subjects are those in which a diagnosis of viral hepatitis, a diagnosis of AIH, and a diagnosis of PBC have been excluded. Such diagnostic methods involve assessing a level of E3 and alkaline phosphatase (AP) in a biological sample from the subject. In general, where a subject has an E3 level above a control E3 level or an AP level above a control AP level, there is an increased likelihood the liver disease is PSC.

Subjects suitable for assessment using this method involving E3 levels and AP levels are those subjects in which PSC is suspected. Such subjects include those who, for example, for whom AIH has been excluded as the likely liver disease affecting the subject ("AIH negative"), and/or for whom PBC has been excluded as the likely liver disease affecting the subject ("PBC negative"). A subject can be diagnosed as AIH negative where the subject, for example, is negative for an AIH marker such as a marker selected from an anti-nuclear antibody (ANA), an antibody to liver/kidney microsome type 1 (anti-LKM1), and an antibody to soluble liver/pancreas antigen (anti-SLA/LP); and/or by determining the subject does not have an increased likelihood of having AIH (as opposed to PSC or PBC) according to the methods described below. A subject can be diagnosed as PBC negative where the subject is negative for anti-mitochondrial antibody (AMA).

The control E3 levels used to facilitate a diagnosis of PSC in a subject suspected of having PSC can be a control E3 level as described above in the context of an assay to facilitate a diagnosis of a liver disease of at least one of AIH, PBC, and PSC.

Control AP Levels

AP levels for use in the methods of the present disclosure can be assayed using commercially available kits, and can involve assaying for AP levels indirectly by assaying a level of AP enzymatic activity or directly by detection of AP protein. For example, where the AP level is determined by detection of enzymatic activity of AP in serum, the control AP level (i.e., normal AP level) is about 30 to 130 IU/liter serum, where AP levels in the range of about 40-129 IU/liter are considered normal for men and AP levels in the range of about 35-104 IU/liter are considered normal for women. Thus, for example, an AP enzymatic activity level that is greater than about 129 IU/liter serum.

Algorithms for Facilitating a Diagnosis of Suspected PSC Using E3 and AP Levels

The algorithm for analysis of test values of E3, E1 and MDC can use any of the control values discussed above, and may be generally described as follows:

$$(E3>X) \text{ or } (AP>K) \quad \text{(Algorithm IV)}$$

wherein
X is an E3 control value;
K is a control AP value,
such that when test values of E3 or AP satisfy Algorithm IV, there is an increased likelihood of PSC in the subject. Where the sample is serum, the E3 control value X can be, for example, 28 pg/ml, 25 pg/ml, or 23 pg/ml. Where the sample is serum and the AP assay is an assay for enzymatic activity, K can be a value of from about 30 to 130 IU/liter serum. Where the subject is male, K can be about 40-129 IU/liter; where the subject is female, K can be about 35-104 IU/liter.

Diagnosis of AIH

The methods of the present disclosure include methods for assessing whether a subject has AIH. Such methods generally involve detecting a level of E3, detecting a level of E1, detecting a level of MDC, and detecting a level of IL-15 in a biological sample from the subject. The E3 level, the E1/E3 ratio (or control (E3/E1×100) value), the MDC level and the IL-15 level can then be used to facilitate a differential diagnosis of AIH against PSC, PBC, as well as against HCV-infected and healthy individuals. Such methods are described in more detail below.

The control E3 levels, control E1/E3 ratio (or control (E3/E1×100) value), and control MDC level can be those as described above in the context of an assay to facilitate a diagnosis of AIH.

The control IL-15 level, which may also be referred to as an IL-15 threshold value or IL-15 cutoff value, can be determined as described herein, e.g., by assaying IL-15 levels in patient populations and, e.g., by assaying IL-15 levels in patient populations and, through application of statistical analysis, identifying an IL-15 level that, when applied in an algorithm with a control E1 level, and control E1 and E3 levels ratio, and MDC level, can provide for a desired sensitivity (e.g., at least 50%, at least 55%, at least 65% or greater), and with a desired specificity.

Values for control IL-15 levels can be readily determined using reagents and methods known in the art, and may vary with the assay used and the biological sample used. For example, where the assay is an immunoassay and the biological sample is serum, the control IL-15 levels can be about 2-3 pg/ml serum, about 2.2-2.8 pg/ml serum, or about 2.4-2.5 pg/ml serum, about 2.4 pg/ml serum, or about 2.5 pg/ml serum, The algorithm for analysis of test values of E3, E1 and MDC can use any of the control values discussed above, and may be generally described as follows:

$$(E3>X)+(E1/E3>Y)+(MDC>Z)+(IL-15>B) \quad \text{(Algorithm II)}$$

Or $$(E3>X)+((E3/E1)\times100)<Y')+(MDC>Z)+(IL-15>B) \quad \text{(Algorithm II')}$$

wherein
X is an E3 control value;
Y is a control E1/E3 ratio value;
Y' is a control ((E3/E1)×100) value;
Z is a control MDC value, and
B is a control IL-15 value such that when test values of E3, E1, MDC and IL-15 satisfy all elements of Algorithm II or of Algorithm II', there is an increased likelihood of AIH in the subject, and further an increased likelihood the subject has AIH as opposed to a PSC or PBC.

In one embodiment, the algorithm for analysis of test serum values of E3, E1 and MDC may be generally described as follows:

$$(E3>18\text{-}45 \text{ pg/ml})+(E1/E3>10\text{-}20)+(MDC>1870\text{-}3000 \text{ pg/ml})+(IL\text{-}15>2\text{-}3) \quad \text{(Algorithm IIa)}$$

Or $$(E3>18\text{-}45 \text{ pg/ml})+((E3/E1)\times100)<6\text{-}7)+(MDC>1870\text{-}3000 \text{ pg/ml})+(IL15>2\text{-}3) \quad \text{(Algorithm IIa')}$$

such that when test values of E3, E1, MDC and IL-15 satisfy all elements of Algorithm IIa or of Algorithm IIa', there is an increased likelihood of AIH in the subject, and further an increased likelihood the subject has AIH as opposed to a PSC or PBC.

In one embodiment, method involves applying the E3 level, E1/E3 ratio, MDC level and IL-15 level to the following algorithm (values are calculated as pg/ml serum):

$$(E3>25)+(E1/E3<15)+(MDC>1870)+(IL\text{-}15>2.4) \quad \text{(Algorithm IIa)}$$

or $$(E3>25)+(E1/E3<15)+(MDC>1870)+(IL\text{-}15>2.5) \quad \text{(Algorithm IIIb)}$$

there is an increased likelihood of AIH in the subject (as opposed to PSC or PBC) (values are calculated as pg/ml serum).

Methods and Panels of Markers

In general, the methods of the present disclosure involve detecting 1, 2, 3, 4 or more of E3, E1, MDC, IL-15 and AP in a biological sample of a subject. Generally, the methods involve detecting E3 and at least 1, 2, 3, or more of E1, MDC, and AP. Accordingly, the present disclosure contemplates methods using a panel of biomarkers for detection of E3 and at least 1, 2, 3, or more of E1, MDC, and AP, as well as compositions useful in detection of such markers, e.g., arrays for detection of marker polypeptide; kits with reagents for detection of marker polypeptides, and the like.

The table below provides an example of how a biomarker panel with E3 and E1, MDC, IL-15 and/or AP can be used to facilitate a diagnosis of a liver disease. A "+" indicates the condition in that column is satisfied. Control levels of biomarkers refer to controls levels as described herein. "NN" indicates assessing the marker is not necessary to facilitate the diagnosis indicated in the far left column.

| Diagnosis Facilitated | E3 level > control E3 level | E1/E3 ratio > or < control E1/E3 ratio | MDC level > control MDC level* | IL-15 level > control IL-15 level | AP level > control AP level |
|---|---|---|---|---|---|
| PSC, PBC, or AIH likely present if . . . | + | NN | NN | NN | NN |
| PSC likely present if . . . | + | + (>) | + | NN | NN |
| AIH likely present if . . . | + | + (<) | + | + | NN |
| PSC likely present if . . . | + (or AP+) | NN | NN | NN | + (or E3+) |

*MDC control level here refers to the cutoff levels described elsewhere herein (e.g., FIGS. 5-8, and 14), rather than level of MDC in healthy individuals, and differs for assessment of likelihood of PSC and assessment of likelihood of AIH as described herein.

Reports

The methods of the present disclosure can include generating a report indicating the results of the method and providing guidance as to how the results might be applied to the care of the subject. A "report," as described herein, refers generally to an electronic document or file (e.g., pdf file, monitor display), as well as a tangible document (e.g., paper report). A subject report can be completely or partially electronically generated, e.g., presented on an electronic display (e.g., computer monitor).

The method results in the report can include, for example, one or more of the level of the biomarker(s) assayed (e.g., an E3 level, an E1 level, a MDC level and/or a an IL-15 level). The level can be reported as a quantitative score (e.g., a concentration, e.g., pg/ml serum) and/or a semi-quantitative score (e.g., a score reflecting an amount of a biomarker relative to a control level or a selected threshold level). The method results can optionally include assay results for a control biomarker.

Reports can include information such as a predicted risk that the patient has or will develop a liver disease of AIH, PBC, and/or PSC; has or will develop AIH; has or will develop PBC; and/or has or will develop PSC.

Reports can include guidance to a clinician as to a treatment recommendation for the subject based on the likelihood of the presence or absence of a liver disease of at least one of AIH, PBC, and PSC; and the type of liver disease (e.g., AIH, PBC, and/or PSC). For example, reports can include a recommendation regarding further evaluation and/or avoiding expensive and invasive evaluations and/or a recommendations regarding therapeutic intervention (e.g., administering a drug, recommending surgical intervention, etc.), modifying a treatment regimen (e.g., adjusting a drug dose (e.g., increasing or decreasing a dose), adjusting a dosage regimen (e.g., increasing or decreasing dose frequency and/or amount), and the like.

A report can further include one or more of: 1) patient information (e.g., name, medical information (e.g., age, gender, symptoms (e.g., symptoms that may be relevant to diagnosis of an inflammatory liver disease), viral infection status (e.g., presence/absence of viral hepatitis), etc.), 2) information about the biological sample (e.g., type, when obtained); 3) information regarding where and how the assay was performed (e.g., testing facility, assay format); 4) service provider information; and/or 5) an interpretive report, which can provide a narrative providing an at least partial interpretation of the results so as to facilitate a diagnosis by a clinician.

Accordingly, the methods disclosed herein can further include a step of generating or outputting a report providing the method results and, optionally, other information such as treatment guidance as described herein. The report can be provided in the form of an electronic medium (e.g., an electronic display on a computer monitor), or in the form of a tangible medium (e.g., a report printed on paper or other tangible medium). An assessment as to the likelihood can be referred to as "risk report" or, simply, a "diagnostic result". The person or entity that prepares a report ("report generator") may also perform steps such as sample gathering, sample processing, and the like. Alternatively, an entity other than the report generator can perform steps such as sample gathering, sample processing, and the like. A report can be provided to a user. A "user" can be, for example, a health professional (e.g., a clinician, a laboratory technician, a physician, etc.).

Computer-Implemented Methods, Systems and Devices

The methods of the present disclosure can be computer-implemented, such that method steps (e.g., assaying, comparing, calculating, and/or the like) are automated in whole or in part. Accordingly, the present disclosure provides methods, computer systems, devices and the like in connection with computer-implemented methods of facilitating a diagnosis of a liver disease of at least one of AIH, PBC, and PSC.

For example, the method steps, including obtaining values for biomarker levels, comparing biomarker levels to a control level, calculating a E1/E3 ratio, generating a report, and the like, can be completely or partially performed by a computer program product. Values obtained can be stored electronically, e.g., in a database, and can be subjected to an algorithm executed by a programmed computer.

For example, the methods of the present disclosure can involve inputting a biomarker level (e.g., an E3 level, an E1 level, a MDC level, and/or an IL-15 level) into a computer programmed to execute an algorithm to perform the comparing and calculating step(s) described herein, and generate a report as described herein, e.g., by displaying or printing a report to an output device at a location local or remote to the computer.

The present invention thus provides a computer program product including a computer readable storage medium having a computer program stored on it. In certain aspects, the storage medium is non-transitory (e.g., a storage medium that is not a transitory wave or signal). The program can, when read by a computer, execute relevant calculations based on values obtained from analysis of one or more biological sample from an individual. The computer program product has stored therein a computer program for performing the calculation(s).

The present disclosure provides systems for executing the program described above, which system generally includes: a) a central computing environment; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) an algorithm executed by the central computing environment (e.g., a processor), where the algorithm is executed based on the data received by the input device, and wherein the algorithm calculates a value, which value is indicative of the likelihood the subject has a liver disease of at least one of AIH, PBC, and PSC as described herein.

Computer Systems

A generalized example of a computerized embodiment in which programs to facilitate execution of the methods of the present disclosure can be implemented is depicted in FIG. 1, which illustrates a processing system 100 which generally comprises at least one processor 102, or processing unit or plurality of processors, memory 104, at least one input device 106 and at least one output device 108, coupled together via a bus or group of buses 110. In certain embodiments, input device 106 and output device 108 can be the same device. An interface 112 can also be provided for coupling the processing system 100 to one or more peripheral devices, for example interface 112 can be a PCI card or PC card. At least one storage device 114 which houses at least one database 116 can also be provided.

The memory 104 can be any form of memory device, for example, volatile or non-volatile memory, solid state storage devices, magnetic devices, etc. In certain aspects, the memory includes a non-transitory storage medium (e.g., a storage medium that is not a transitory wave or signal). The processor 102 can comprise more than one distinct processing device, for example to handle different functions within the processing system 100. Input device 106 receives input data 118 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 118 can come from different sources, for example keyboard instructions in conjunction with data received via a network.

Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 can be distinct and derived from different output devices, for example a visual display on a monitor in conjunction with data transmitted to a network. A user can view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. The processing system 100 may be any suitable form of terminal, server, specialized hardware, or the like.

The processing system 100 may be a part of a networked communications system. Processing system 100 can connect to a network, for example the Internet or a WAN. Input data 118 and output data 120 can be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 3 may operate in a networked environment using logical connections to one or more remote computers. The remote computer may be a personal computer, a server, a router, a network PC, a peer device, or other common network node, and typically includes many or all of the elements described above.

The logical connections depicted in FIG. 3 may include a local area network (LAN) and a wide area network (WAN), but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 3 are examples and other means of establishing a communications link between multiple computers may be used.

FIG. 3 is intended to provide a brief, general description of an illustrative and/or suitable example of a computing environment in which embodiments of the methods disclosed herein may be implemented. FIG. 3 is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

Certain embodiments may be described with reference to acts and symbolic representations of operations that are performed by one or more computing devices, such as the computing system environment 100 of FIG. 3. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, multiprocessor systems, microprocessor-based systems, programmable consumer electronics, network, minicomputers, server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media (e.g., non-transitory storage media, where the medium is not a transitory wave or signal) including memory storage devices.

Computer Program Products

The present disclosure provides computer program products that, when executed on a programmable computer such as that described above with reference to FIG. 3, can carry out the methods of the present disclosure. As discussed above, the subject matter described herein may be embodied in systems, apparatus, methods, and/or articles depending on the desired configuration. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. video camera, microphone, joystick, keyboard, and/or mouse), and at least one output device (e.g. display monitor, printer, etc.).

Computer programs (also known as programs, software, software applications, applications, components, or code) include instructions for a programmable processor, and may be implemented in a high-level procedural and/or object-oriented programming language, and/or in assembly/machine language. As used herein, the term "machine-readable medium" (e.g., "computer-readable medium") refers to any computer program product, apparatus and/or device (e.g., magnetic discs, optical disks, memory, etc.) used to provide machine instructions and/or data to a programmable processor, including a machine-readable medium that receives machine instructions as a machine-readable signal. According to certain embodiments, the machine-readable medium is non-transitory (e.g., a machine readable medium that is not a transitory wave or signal).

It will be apparent from this description that aspects of the present invention may be embodied, at least in part, in software, hardware, firmware, or any combination thereof. Thus, the techniques described herein are not limited to any specific combination of hardware circuitry and/or software, or to any particular source for the instructions executed by a computer or other data processing system. Rather, these techniques may be carried out in a computer system or other data processing system in response to one or more processors, such as a microprocessor, executing sequences of instructions stored in memory or other computer-readable medium (e.g., a non-transitory computer-readable medium) including any type of ROM, RAM, cache memory, network memory, floppy disks, hard drive disk (HDD), solid-state devices (SSD), optical disk, CD-ROM, and magnetic-optical disk, EPROMs, EEPROMs, flash memory, or any other type of media suitable for storing instructions in electronic format.

In addition, the processor(s) may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices. In alternative embodiments, special-purpose hardware such as logic circuits or other hardwired circuitry may be used in combination with software instructions to implement the techniques described herein.

Examples of Applications of Method Results

The methods of the present disclosure can provide results which can then be applied to facilitate decisions as to the care of the subject. Examples are provided below.

Assay-Guided Therapy and Monitoring of Therapy

The methods of the present disclosure can facilitate a clinician in making a treatment decision for the subject, e.g., whether the results of the method suggest the subject may or may not benefit from therapeutic intervention for treatment of an inflammatory liver disease of AIH, PSC, or PBC. For example, based on the method results, a therapy cant be selected for the subject based on the likelihood s/he has or is at risk of an inflammatory liver disease of one or more of AIH, PBC, and PSC, has or is at risk of a liver disease of one or more of AIH, PBC, and PSC, has or is at risk of AIH, has or is at risk of PBC, or has or is at risk of PSC. Clinical signs, symptoms and other factors such as presence or absence of viral hepatitis (e.g., HCV) can also be considered to facilitate selecting a therapy.

The method results can guide a clinician as to whether or not any therapy for treatment of an inflammatory liver disease should be administered.

The methods of the present disclosure can facilitate monitoring therapy of a subject undergoing treatment. For example, where the subject is already receiving a therapy, the method can provide a method of monitoring therapy. In this case, the method results can guide a clinician in adjusting therapy (e.g., whether or not to continue therapy (e.g., so as to avoid relapse), increase or decrease dose, change therapy regimen (e.g., from monotherapy to combination therapy, or from non-surgical therapy to surgical therapy) where the patient is not receiving adequate therapeutic benefit (e.g., the patient is not responding to therapy), and the like). Such methods of monitoring therapy are useful in guiding further treatment decisions, such as whether continued administration of a drug regimen indicated, or whether the patient should receive a liver transplant. The methods of monitoring therapy using the algorithms of the present disclosure may be used in combination with other methods for assessing whether a subject responds to therapy (is a "responder") or is not exhibiting a sufficient therapeutically beneficial response (is as "nonresponder"). For example, where the patient is diagnosed with PBC, patients who are responders to ursodeoxycholic acid (UDCA) achieve significant reduction in alkaline phosphatase (AP) after the first year of treatment.

The methods of the present disclosure can be useful in selecting therapy where a diagnosis of PBC is indicated. The standard of care for PBC is administration of UDCA. Liver transplantation is indicated where the subject is at risk of liver failure. The methods of the present disclosure may be used to monitor efficacy of a non-surgical therapy (e.g., UDCA) for a PBC patient. Where a diagnosis of PBC persists, the clinician may be guided to modify therapy (e.g., dose, dosage, and/or type of therapy, e.g., combination therapy versus monotherapy), including making a decision to treat the patient surgically.

The methods of the present disclosure can be useful in selecting therapy where a diagnosis of PSC is indicated. Currently, there are no available non-surgical curative therapies that have proven effective, at least in part due to the lack of therapeutic endpoints, which is in turn due to the lack of diagnostic methods until the methods of the present disclosure. Thus, where a diagnosis of PSC is indicated, the clinician may be guided to treat the patient surgically, depending on other factors, such as the severity of other patient signs and symptoms. In general, so long as a PSC patient has a functional liver, palliative and symptomatic therapies are may be administered, including antibiotic therapies and palliative surgical biliary drainage, endoscopic dilatation and stenting. Alternatively or in addition, the clinician may elect to treat the patient non-surgically and monitor efficacy of therapy using the methods of the present disclosure. Non-surgical therapies may include administration of UDCA, cholestyramine, and/or hydroxyzine HCL for alleviation of symptoms (e.g., pruritus). Administration of antibiotics may be indicated where infectious cholangitis is suspected. However, should the disease progress such that the patient is at risk of liver failure, liver transplantation is indicated.

In AIH, immunosuppressive agents such as corticosteroids (e.g., prednisone or prednisolone) with or without azathioprine can be administered to control the disease. In cases without liver cirrhosis the topical steroid budesonide can be administered. Because of the side effects associated with immunosuppressive treatments, a firm diagnosis before treatment is started would be desirable. About 40% of patients achieve complete remission meaning normal serum transaminases (ALT and AST) and normal IgG levels between months 6 and 12. A therapeutic challenge are the so called AIH non-responders to standard of care with predniso (lo)ne plus minus azathioprine. Treatment has to be continued in remission at least 2-3 years and liver biopsy has to be performed to confirm lack of disease activity by histopathology; otherwise patients will relapse after cessation of treatment. Up to 80% of patients experience relapse and then immunosuppressive treatment has to be started again. Thus, the methods of the present disclosure can find use in monitoring response to therapy and reduce risk of relapse. If a patient is at risk of relapse as indicated by use of the algorithms of the diagnostic methods disclosed herein, the clinician may be guided to reinitiate therapy, and may indicate surgical intervention (e.g., liver transplant).

Identifying Subjects for Clinical Trial Populations

The methods of the present disclosure find use in identifying subjects suitable for inclusion or exclusion in a clinical trial based on upon the likelihood the subject has one or more of AIH, PBC or PSC. For example, the methods of the present disclosure can be used to identify subjects suitable for inclusion in a clinical trial to assess efficacy of a drug on treatment of one or more of PSC, PBC, or AIH, so that subjects that do not have one of these conditions is excluded. In another example, the methods of the present disclosure can be used to identify subjects having one or more of PSC, PBC or AIH so as to excluded such subjects from a clinical trial (e.g., where the clinical trial is to assess efficacy of a drug for a disease other than PSC, PBC, or AIH). In another example, the methods of the present disclosure can be used to identify subjects suitable for inclusion in a clinical trial to assess efficacy of a drug on treatment of PBC, such that subjects having AIH or PSC are excluded. In this latter embodiment, a diagnosis of PBC may be further confirmed by other methods, e.g., by exclusion of other inflammatory liver diseases such that, more likely than not, the patient population has PBC. Such methods can facilitate identification of drugs or other therapies for treatment of one or more of AIH, PSC or PBC.

Kits

Kits of the present disclosure can include a binding reagent(s) for one or more, two or more, three or more or for each of E3, E1, MDC, and/or IL-15. The binding reagent can be, for example, and antibody that specifically binds a biomarker (e.g., an anti-E3 antibody, anti-E1 antibody, and anti-MDC antibody, an anti-IL15 antibody). In some embodiments, the kit includes a binding reagent for E3 and a reagent(s) for detection of AP. The reagent(s) for detection of AP can be reagent(s) to detect enzymatic activity of AP, or a binding reagent, e.g., an anti-AP antibody. "Binding reagent" as used here encompasses both capture reagents and detection reagents. A "capture reagent" refers to a binding partner for a biomarker that is suitable for use in, for example, enriching a sample for its respective biomarker, e.g., an anti-biomarker antibody. Where the capture reagent comprises an antibody, the antibody may be a polyclonal or monoclonal antibody. "Detection reagent" refers to a binding partner for a biomarker that is suitable for use in detection of an immobilized biomarker, e.g., an anti-biomarker antibody, and is optionally detectably labeled. Where the detection reagent comprises an antibody, the antibody may be a polyclonal or monoclonal antibody. Kits may further include one or more reagents for detection of binding of a detection reagent, e.g., detection of an anti-biomarker antibody, e.g., as when bound to an anti-biomarker binding reagent/biomarker complex.

Where the kit includes reagent(s) for detection of AP, the kit can include one or more reagents to facilitate detection of enzymatic activity of AP in a sample, e.g. by detection of cleavage of an AP substrate, such as an organic phosphate ester substrate (e.g., p-nitrophenylphosphate). Kits for detection of AP enzymatic activity are commercially available. For example, the Alkaline Phosphatase Reagent (Cat # REF 442670), used with the SYNCHRON® System and supplied by Beckman Coulter involves the organic phosphate ester substrate p-nitrophenylphosphate for detection of AP enzymatic activity. Cleavage of the colorless p-nitrophenylphosphate substrate results in production of phosphate and the yellow-colored product, p-nitrophenol. For example, AP assay kits that are commercially available include those are based on colorimetric detection of a production of the AP enzymatic reaction. Kits for detection of AP may include anti-AP antibodies (e.g., anti-AP monoclonal antibodies), which can be used for detection of AP polypeptide in a biological sample by e.g., detection of an immunocomplex formed by binding of a specific anti-AP antibody and AP of a biological sample. Anti-AP antibodies may be used as a capture reagent for immobilization of AP polypeptides in a sample, and the AP in the immunocomplex detected using a secondary anti-anti-AP antibody or by detection of AP activity, e.g., using a colorimetric assay.

Examples of kits include those having: a binding reagent for E3 (e.g., an anti-E3 antibody), and a binding reagent for E1 (e.g., an anti-E1 antibody); a binding reagent for E3 (e.g., an anti-E3 antibody), a binding reagent for E1 (e.g., an anti-E1 antibody), and a binding reagent for MDC (e.g., an anti-MDC antibody); and a binding reagent for E3 (e.g., an anti-E3 antibody), a binding reagent for E1 (e.g., an anti-E1 antibody), and a binding reagent for MDC (e.g., an anti-MDC antibody), and a binding reagent for IL-15 (e.g., an anti-IL-15 antibody). Binding reagents for a control analyte (e.g., a control biomarker) can also be included.

Capture reagents provided in a kit of the present disclosure can be immobilized on an insoluble support, e.g., an assay substrate, such as an array, bead, and the like as described herein. Detection reagents can include a detectable label. Where the detection reagents are not detectably labeled, the kit can include reagents for detecting the detection reagents, such as an antibody. For example, where the kit includes detection reagents for two or more of E1, E3, MDC and/or IL-15 (e.g., an anti-E3 antibody, anti-E1 antibody, anti-MDC antibody, and/or an anti-IL15 antibody), the kit can include antibodies that are specific for each of the detection reagents, which antibodies are differentially labeled according to the specificity for the detection reagent to which each antibody binds. The various components of the kit may be present in separate containers or certain compatible components may be pre-combined into a single container, as desired.

Kits can include instructions for using the components of the kit to practice a method of the present disclosure. The instructions are generally recorded on a suitable recording medium, such as paper, plastic, electronic storage medium, and the like. For example, the instructions may be present in the kits as a package insert, in the labeling of the container of the kit or components thereof (e.g., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In other examples, the instructions provided do not contain many or all assay details, but rather provide direction as to a remote source for obtaining detailed instructions, e.g. via the internet.

Treatment Methods

The present disclosure provides methods of treating AIH, PBC and PSC by administering to a subject in need thereof an effective amount of an antagonist of E3 and/or an antagonist of an E3 receptor. Also provided are methods of treating PSC by administering to a subject in need thereof an effective amount of an antagonist of E1 and/or an antagonist of an E1 receptor (optionally in combination with an antagonist of E3 and/or an antagonist of an E3 receptor). The present disclosure also provides methods of treating AIH by administering to a subject in need thereof an effective amount of an antagonist of IL-15 and/or an antagonist of an IL-15 receptor (optionally in combination with an antagonist of E3 and/or an antagonist of an E3 receptor).

"Antagonist" as used herein refers to a drug (e.g., antibody) that reduces or blocks activity of its target. Representative antagonists, include, but are not limited to, antibodies (including antigen-binding antibodies), nucleic acids (e.g., antisense molecules, such as ribozymes and RNA interfering agents), immunoconjugates (e.g., an antibody conjugated to a therapeutic agent), small molecule drug inhibitors, fusion proteins, aptamers, and the like. Reduction of activity of a target (e.g., of E1 and/or E3) can be accomplished by, for example, reducing an amount of active target present in the bloodstream of a subject or an E3- or E1-producing tissue of the subject, and/or reducing activity of the target.

In one embodiment, the antagonist is an antibody or an antigen-binding fragment of an antibody that specifically binds and blocks the action of E1 (see, e.g., U.S. Pat. No. 6,946,546), E3, an E1 receptor, and/or an E3 receptor.

In another embodiment, the E1, E3, E1 receptor and/or E3 receptor antagonists are small molecules. As used herein, "small molecule" refers to synthetic chemical molecules that are less than about 1000 daltons in molecular weight, such as less than 750 daltons, including molecules less than 700 daltons, and inhibit E1 or E3 activity.

In another embodiment, the E1 or E3 antagonist is an antisense nucleic acid molecule (e.g., an antisense RNA, silencing RNA (siRNA), short hairpin RNA (shRNA), microRNA (miRNA), or other nucleic acid molecule of interest) that is complementary to a mRNA encoding E1 or E3, or to a portion of that mRNA, or a recombinant expression vector encoding such a nucleic acid molecule. As used herein, an "antisense" RNA, siRNA, shRNA or miRNA nucleic acid comprises a nucleotide sequence specific to the gene and/or mRNA encoding E3 or E1.

Antisense nucleic acids can be designed according to the rules of Watson and Crick base pairing. The antisense nucleic acid molecule can be complementary to the entire coding region of E1 or E3 mRNA, or to only a portion of the coding or noncoding region of BMP9 or BMP10 mRNA. For example, the antisense oligonucleotide can be complementary to the region surrounding the translation start site of E1 or E3 mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Antisense nucleic acid can be produced biologically using an expression vector into which a nucleic acid has been subcloned in an antisense orientation, e.g., such that RNA transcribed from the inserted nucleic acid will be if an antisense orientation to a target nucleic acid of interest.

The antagonists of E1 or E3 include RNA interfering agents (RNAi), which include, but are not limited to, nucleic acid molecules including RNA molecules which are homologous to E1 or E3, "short interfering RNA" (siRNA), "short hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA.

In general, the methods of treatment involve identifying a subject as having one or more of AIH, PBC, or PSC, and administering an amount of an E1 antagonist, an E3 antagonist, or both, effective to provide a therapeutic benefit in the patient. "Therapeutic benefit", "treat", "treatment" includes at least reduction the severity of, or amelioration of one or more symptoms of a disease. Therapy can optionally be combined with other therapy for AIH, PBC or PSC, as appropriate. E1 and E3 antagonists can be administered by any appropriate route, which may be selected according to the agent to be administered. Administration is normally parenteral, and includes injection by an intravenous routes as well as injection into tissue, e.g., involved liver tissue of the subject. In one embodiment, the E1 or E3 antagonist is administered by intravenous infusion, and may be administered by injection for delivery to liver (e.g., via a hepatic artery).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Analysis of Cytokines/Chemokines

Sera samples were collected from healthy individuals and from patients diagnosed with HCV, AIH, PBC, or PSC and evaluated for the level of cytokines/chemokines.

The number of patients in each group included 50 healthy controls, 54 HCV-infected patients, 80 PSC patients (which included 20 patients having PSC only, 22 patients with PSC and ulcerative colitis (UC) 16 patients with PSC and CD (Crohn's disease), 13 patients with PSC+AIH, and 9 patients with PSC, UC, and AIH), 50 patients with PBC and 40 patients with AIH. Diagnosis for HCV was based on serology and PCR. Diagnosis of PSC, UC, CD, and AIH were made by clinical examination and paraclinical testing that could include testing for AMA for PBC and other autoantibodies for AIH, as well as ERC/MRC for PSC, and, in some instance, liver pathology. All HCV patients were chronic HCV patients that were either not responders to treatment or not candidates for treatment. Since PSC is accompanied with UC in up to 80% of cases in the study population, PSC patients with and without IBD were included as a single patient group, but while excluding patients with AIH. Twenty-six cytokines and chemokines were tested and all samples were used in duplicate.

Samples were assayed using the multiplex ELISA kit from Meso Scale Discovery Company (MSD; Meso Scale Discovery, Gaithersburg, Md., USA), which provides a high sensitivity of detection, with wide dynamic range as well as linear standard curve within the area of expected concentrations. All experiments were performed according to the manufacturer's instruction with minimal modifications and optimization.

In brief, after incubation of the Multiplex plate (MSD) with blocking solution Diluent 2 (MSD), standards and samples were dispensed into the wells of a 96-well plate and incubated for 3 h at room temperature (RT) with continuous shaking. The plates were washed and incubated with Anti-cytokine Antibodies Cocktail Labeled with SULFO-TAG (MSD) for additional 3 h followed by washing and adding the 2× Read Buffer T (MSD). The plates were then scanned by SECTOR Imager 6000 Reader (MSD), results were analyzed, and obtained concentrations were corrected for dilution.

Figure 2:
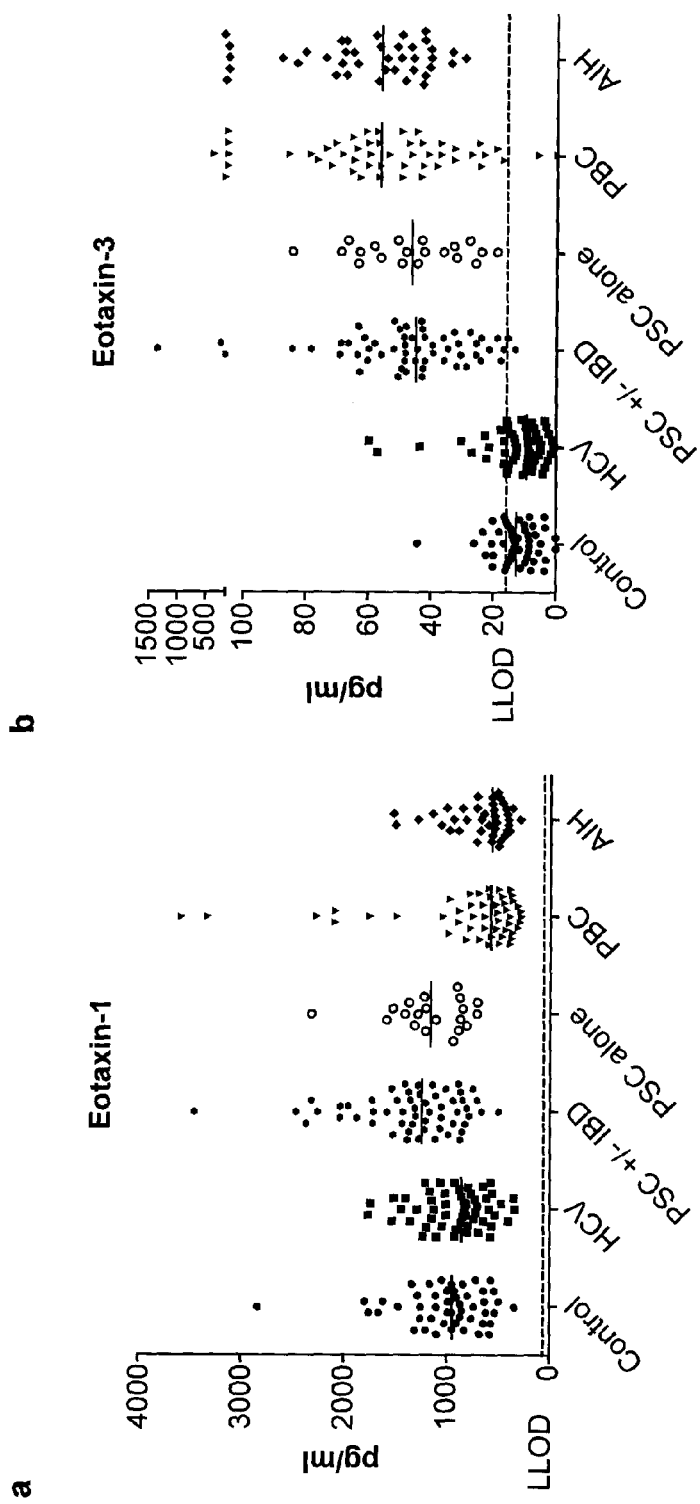
FIG. 2 is a set of graph showing a comparison of the levels of serum eotaxin-1 (panel a), eotaxin-3 (panel b), CCL22 (panel c) and IL-15 (panel d) among control, HCV, AIH, PBC, PSC alone and PSC+/−IBD groups. PSC+/−IBD includes all PSC alone, as well as PSC with UC+PSC with CD; any comorbidity of PSC with AIH was excluded from PSC alone and from PSC+/−IBD. The lower limit of detection (LLOD) for each marker is indicated for each analyte as a long horizontal dashed line across data for all patients. Median values for the marker in each group are indicated by a short horizontal line.
Figure 2:
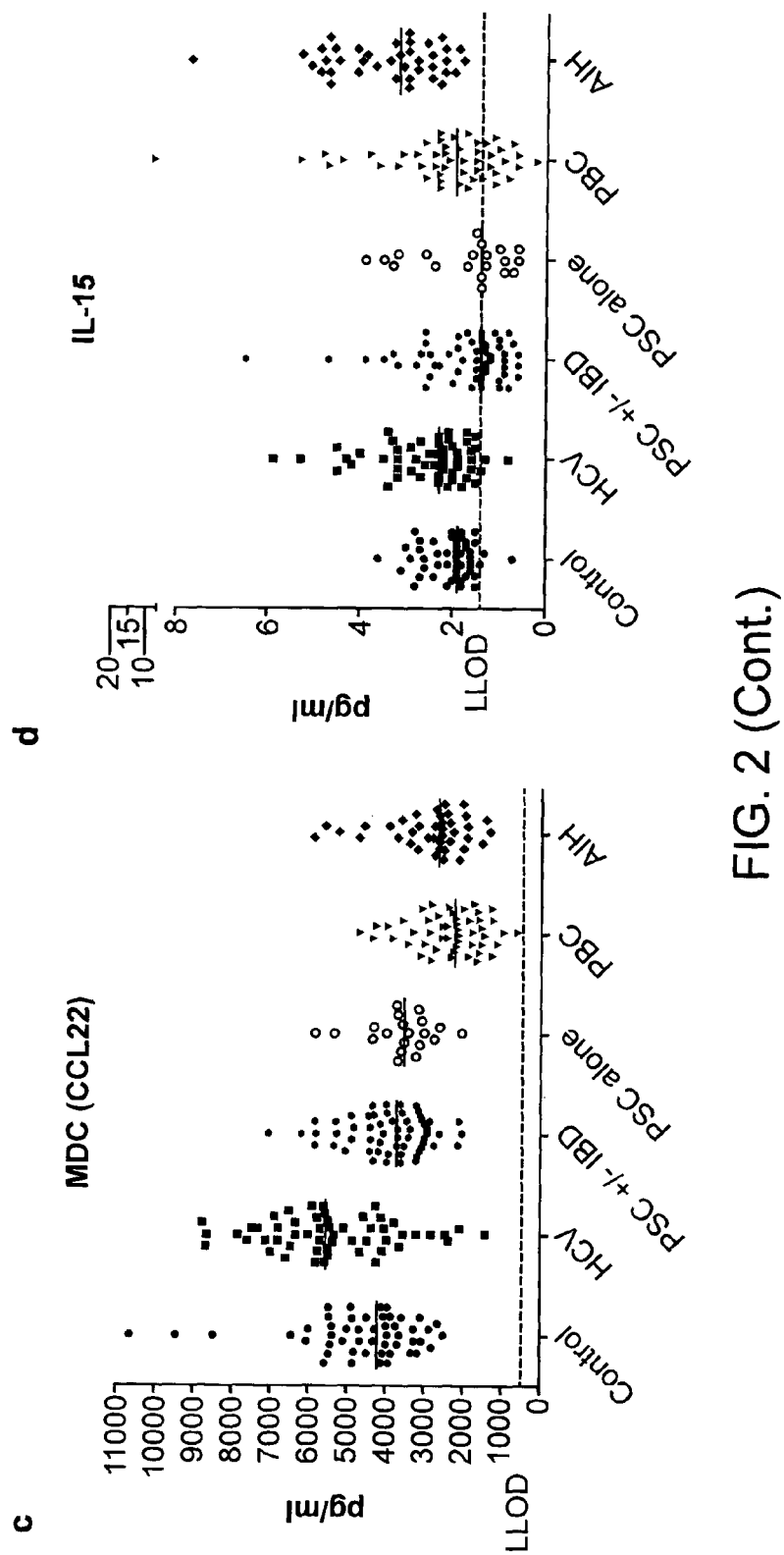
Figure 9:
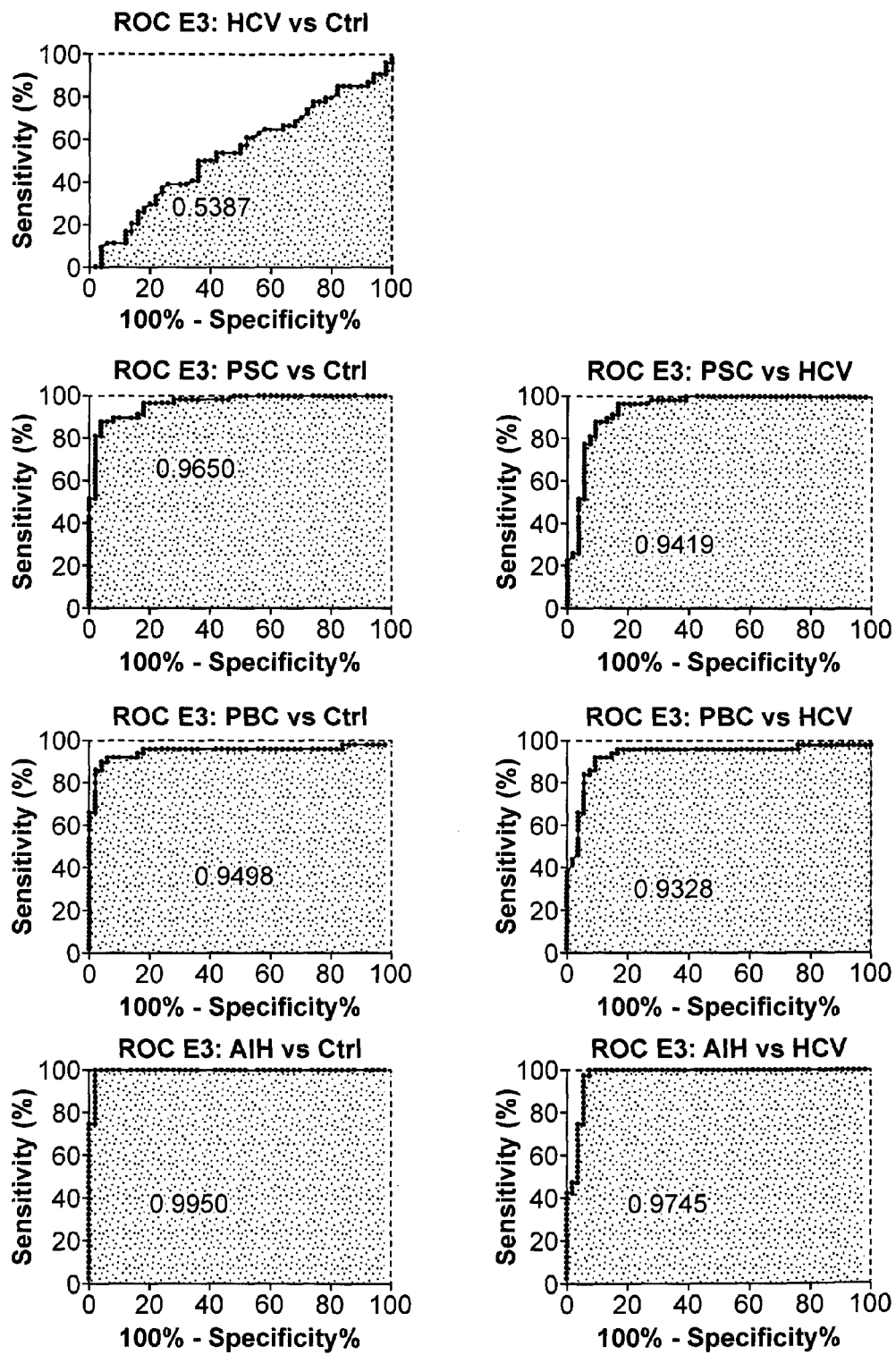
FIGS. 9-13 provide receiver-operator characteristic (ROC) curves for eotaxin-3 (E3.
Figure 10:
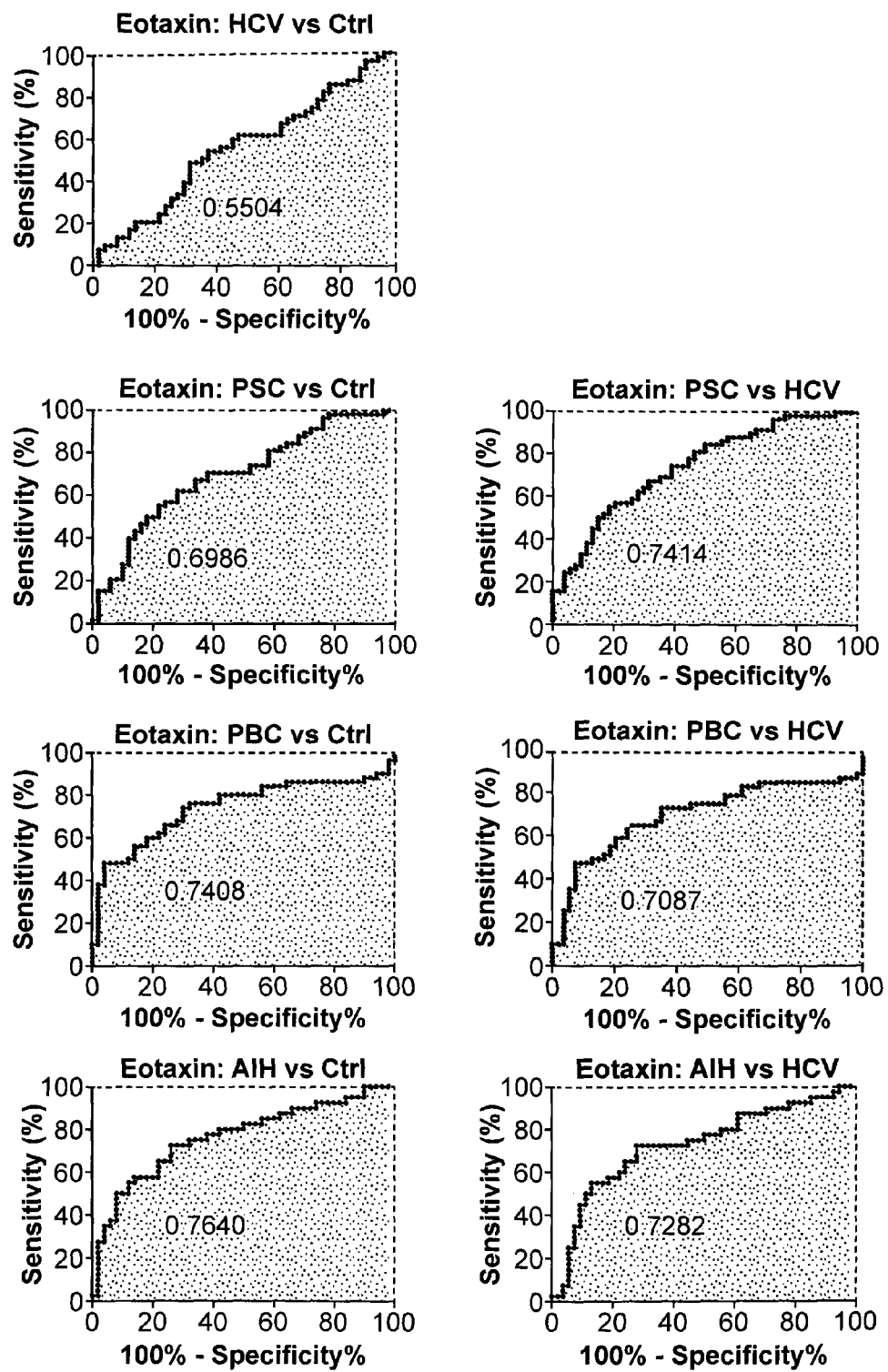
Figure 11:
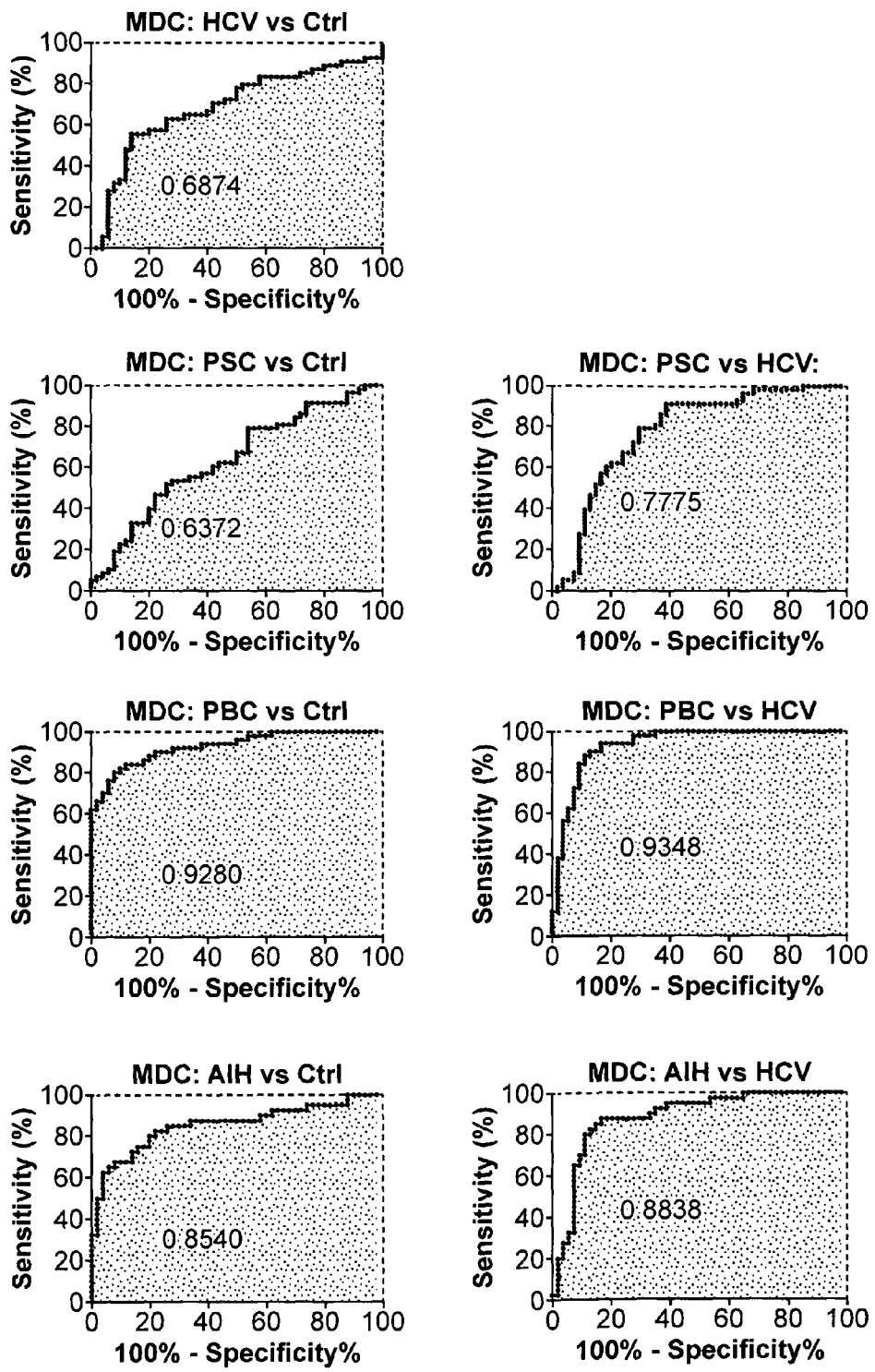
Figure 12:
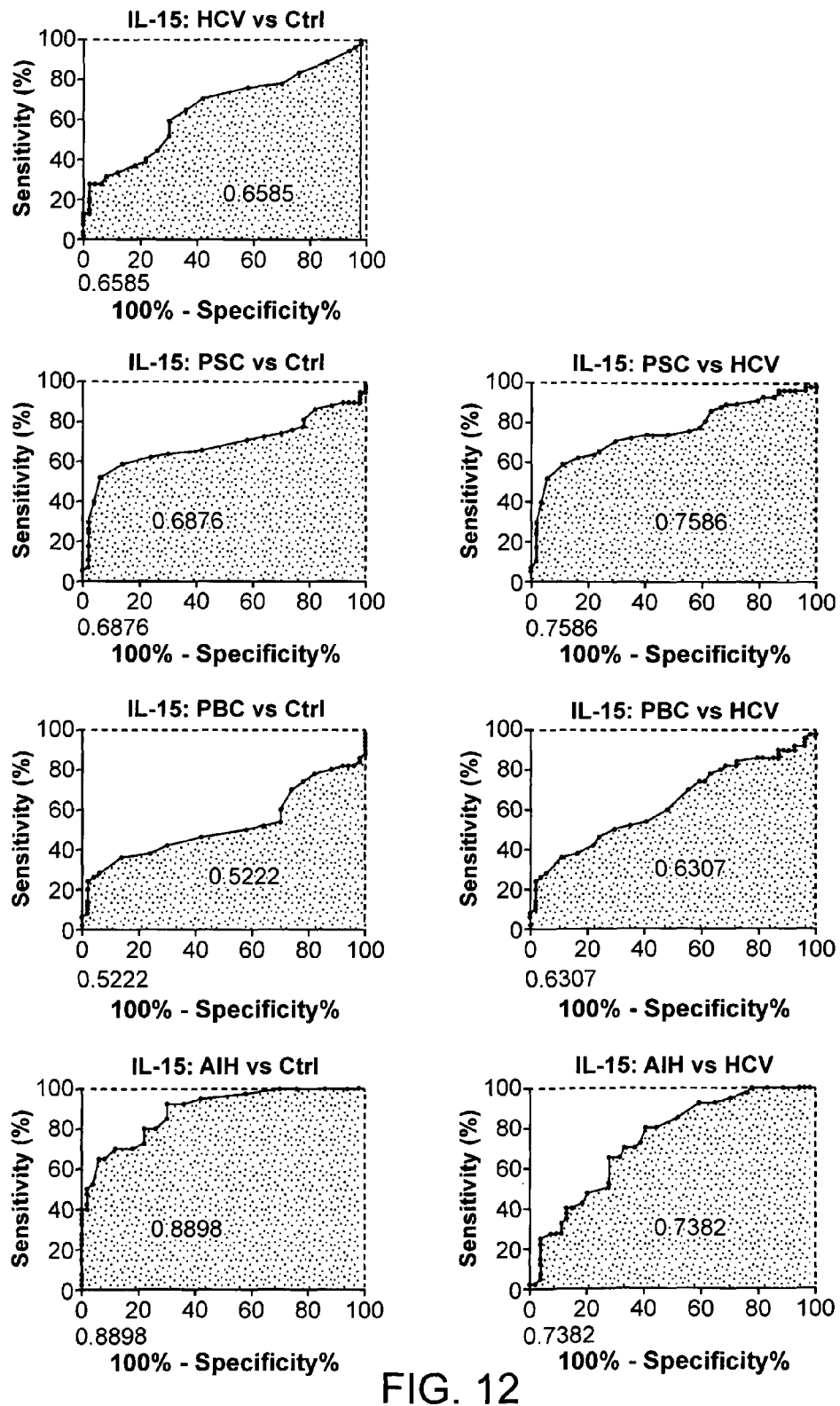
Figure 13:
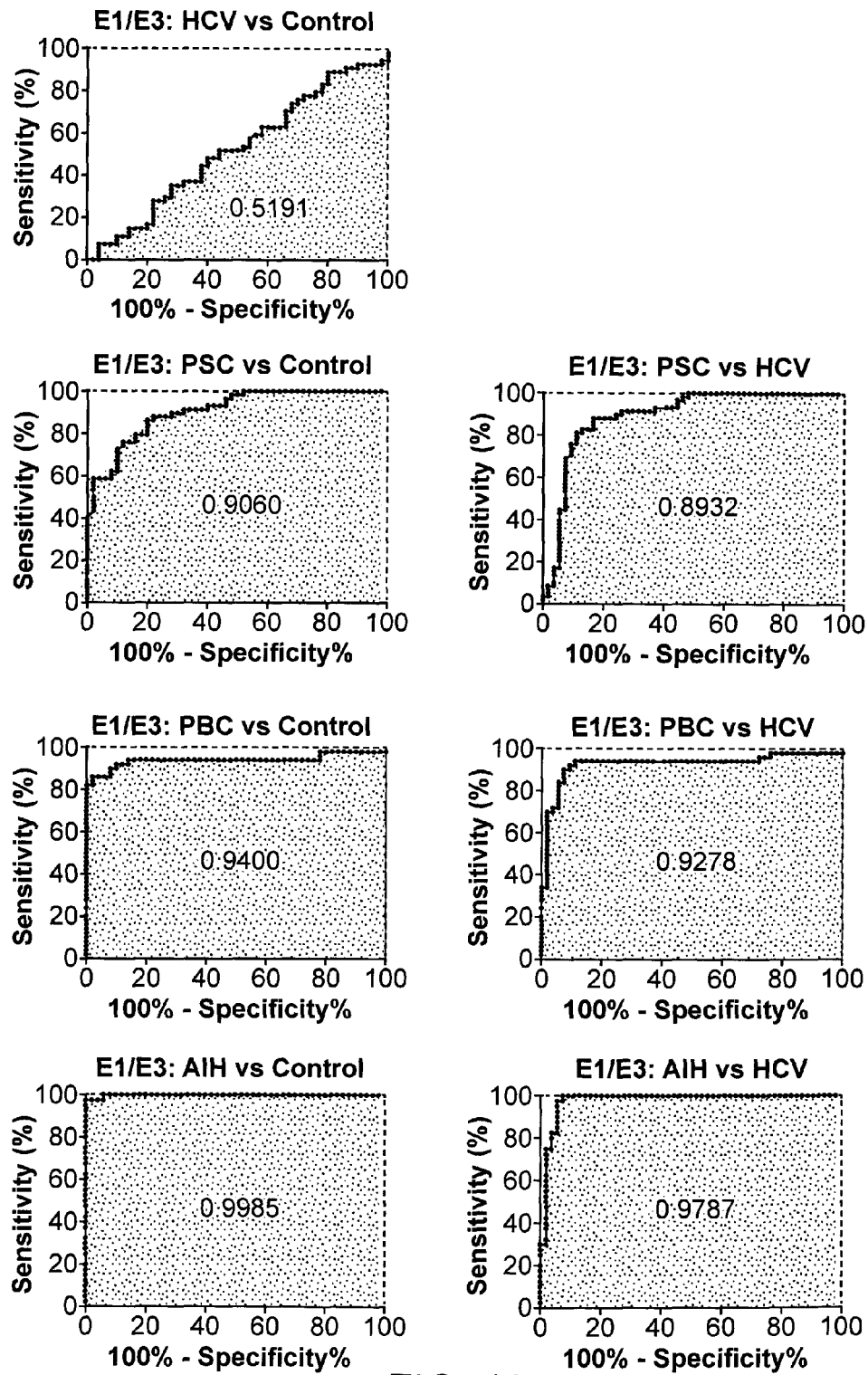

After analysis, the results were compared and cytokines/chemokines exhibiting statistically significant differences between the healthy control, HCV, AIH, PBC, and PSC groups were identified. Significant differences were identified for eotaxin-1 (E1, also known as CCL11), exotoxin-3 (E3, also known as CCL26), macrophage-derived chemokine (MDC, also known as CCL22), and interleukin-15 (IL-15) serum levels. The results are show in FIG. 2, panels A-D, respectively.

The results for HCV patients for all cytokine and chemokines were highly compatible with previous reports in the literature, thus confirming the validity and reproducibility of the assays.

Example 2

Analysis of E3, E1, MDC and IL-15 Serum Levels

The data obtained from Example 1 were subjected to statistical analysis. Different threshold values were selected so as to discriminate between selected conditions (e.g., between a control (e.g., healthy or HCV-infected) and a liver disease of at least AIH, PBC and/or PSC).

FIGS. 3-8 provide tables summarizing the results of this analysis. The percentage values indicate the percentage of individuals of the group in that row that met the criteria set out at the top of the column. The values in the columns adjacent and to the left of the percentage values provide the numbers of individuals in each group that were positive (top value) of the total tested (bottom value). "Ctrl/HCV" indicates patients in the healthy control and HCV-infected groups were combined. "PSC, PBC or AIH" refers to a combination of all patients with AIH, PBC, and PSC. "PSC+/−IBD+/−AIH" included PSC patients whether having PSC alone, PSC with or without IBD, and PSC with or without AIH. "PSC alone" included patients with diagnosis of PSC alone and no comorbidity with other liver diseases. "PSC+/−IBD no AIH" included having PSC alone as well as those having PSC with UC, or PSC with CD, but without comorbidity with AIH. "PSC+AIH+/−IBD" included patients having PSC with AIH, and with or without IBD. "PSC+AIH no IBD" included patients PSC in combination with AIH, but without IBD.

The serum concentrations of E1 and E3 were prominently different between all patient groups tested. Thus E1 and E3 are useful as diagnostic biomarkers for 1) differentiating the AIH, PBC, and PSC from healthy controls and HCV patients and 2) for the discrimination of PSC from AIH and PBC.

As shown in the table of FIG. 3, when a cutoff value of greater than 25 pg/ml serum for E3 distinguishes AIH, PBC, and PSC from healthy controls and HCV patients with a sensitivity of 89% and a specificity of 93%. A cutoff value of greater than 28 pg/ml serum for E3 distinguishes AIH, PBC, and PSC from healthy controls and HCV patients with a sensitivity of 85% and a specificity of 95%.

As shown in FIG. 3, PSC can be discriminated from AIH and PBC by use of the algorithm of $$E3>25+E1/E3>15+MDC>2800$$

(an E3 serum concentration of greater than 25 pg/ml serum, a ratio of E1 serum concentration and E3 concentration (E1/E3 ratio) of greater than 15, and a MDC serum concentration greater than 2800 pg/ml serum). This algorithm discriminated PSC from HCV and healthy controls, and from AIH and PBC with a sensitivity of 72% to 75%, and a specificity of between 92% to 96%.

As shown in FIG. 3, AIH can be distinguished from controls and from PBC by applying the following algorithm to the data:

$$E3>25+E1/E3<15+MDC>1870+IL\text{-}15>2.4 \text{ pg/ml}$$

(an E3 serum concentration greater than 25 pg/ml, a ratio of E1/E3 serum concentrations less than 15, MDC serum concentration greater than 1870 pg/ml, and IL-15 serum concentration is greater than 2.4 pg/ml). This algorithm provided a sensitivity of 60% for AIH with a high specificity of 95-100% against healthy controls, HCV, and PSC and a specificity of 90% against PBC.

Figure 4:
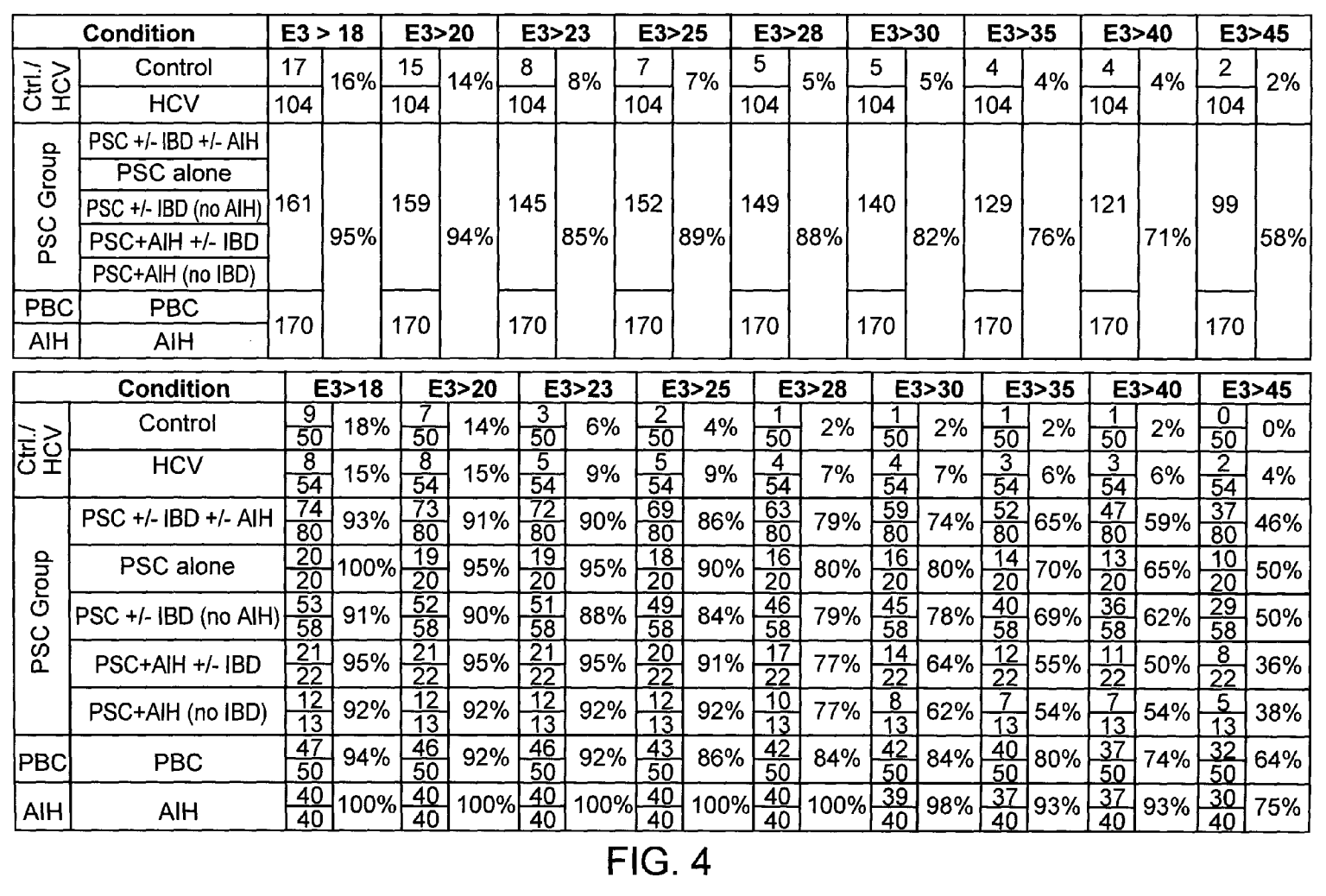

FIG. 4 provides a summary of the results of analysis using different cutoff (or threshold) E3 serum concentrations to facilitate a diagnosis of a liver disease of AIH, PBC, and/or PSC as compared to controls, which included healthy and HCV-infected individuals. The top panel of FIG. 4 shows results using E3 control values of E3>18, E3>20, E3>23, E3>25, E3>28, E3>30, E3>35, E3>40, and E3>45. The bottom panel of FIG. 4 provides a more detailed analysis of the results of the top panel of FIG. 4.

FIG. 5 provides a summary of the results of analysis using various E3 control values with various control E1/E3 ratio values.

FIG. 6 provides a summary of the results of analysis using various E3 control values, various control E1/E3 ratio values, and various MDC control values.

FIG. 7 provides a summary of the results of analysis using (E3/E1×100) values.

FIG. 8 provides a summary of the results of analysis using various E3 control values, various control E1/E3 ratio values, and various IL-15 control values along with an MDC value of 1870 pg/ml.

In addition, the algorithm $$(E3>29)+(E1/E3 \text{ ratio}<15)+(\text{IL-}15>1.7)$$

discriminated AIH from healthy controls and PSC with a sensitivity of 75% and a specificity of 100% and 98%, respectively. Although this algorithm has increased sensitivity for AIH and is simpler that other algorithms for AIH, but with less specificity against PBC and chronic hepatitis C, but this may still be practical if the AMA test is performed and viral hepatitis is ruled out using conventional diagnostics for viruses such the HAV, HBV, HCV, HDV, HEV, EBV, and CMV.

Example 3

Roc Curve Analyses

The data obtained from Example 1 were subjected to analysis using Prism (GraphPad Prism Version 5.00, Prism Software Corporation, Irvine, Calif., USA) to generate a receiver-operator curve (ROC). ROC curves are a standard way of illustrating the relationship between sensitivity and specificity for a specific test, thus providing guidance as to values for desired sensitivity and specificity, e.g., when comparing values from normal and abnormal. Prism was used to generate ROC curves for sensitivity and specificity of each of the E3, E1, MDC, and IL-15 at various cut-offs for HCV, PSC, PBC, and AIH against healthy control (left columns for each of FIGS. 9-13) as well as PSC, PBC, and AIH against HCV (right columns for each of FIGS. 9-13). Prism automatically calculates many pairs of sensitivity and specificity using each value in the data table as the cut-off value. The confidence interval for each possible cut-off in our calculation is 95%.

The area under the curve (AUC) of an ROC curve quantifies the overall ability of the test to discriminate between those individuals with the disease and those without the disease, where a test that is not useful has an AUC of 0.5 and a "perfect" has an AUC of 1. For example, if the AUC is 0.90, a patient will have a more abnormal test result than 90% of the controls. The Prism software provides that the AUC of a ROC curve can never be less than 0.50, since Prism will reverse the definition of abnormal from a higher test value to a lower test value if the area is first calculated as less than 0.50. These results are computed by a nonparametric method, which does not make any assumptions about the distributions of test results in the patient and control groups (Hanley, J. A., and McNeil, B. J. 1982. Radiology 143:29-36).

Where the AUC for an ROC was greater than 0.5, the AUC value is provided in the center of the graph. The AUC of an ROC comparing HCV-infected individuals (HCV) versus healthy control (Ctrl) is provided as a control for comparison purposes.

Example 4

Evaluation of Assay Accuracy

Evaluation of the accuracy of a diagnostic test is one of the characteristics that can describe the quality and usefulness of the test. In addition to sensitivity and specificity as two very common tools for this purpose, accuracy can be expressed through positive and negative predictive values (PPV & NPV), or positive and negative diagnostic likelihood ratios (PDLR & NDLR or PLR and NLR in short). These tools can address common questions that a clinician may ask when a new diagnostic is offered. Those questions are: 1) What is the probability of presence or absence of the disease in the case of a positive or negative test, respectively?; and 2) How would the test increase the pre-test probability of a diagnosis based on the clinic or other tests in order to reduce further diagnostic evaluations?

The PPV of a test expresses the probability of the presence of a disease when a positive result is observed in an individual, and the NPV of a test expresses the probability of the absence of a disease when a negative result is observed in an individual. Inherently, PPV and NPV are dependent upon the prevalence of a disease; so, the use of DLRs may be a more relevant tool as it is independent from the prevalence of a disease that is important especially in the case of a rare disease.

The DLR is a measure of the performance of a diagnostic test. It is calculated from the sensitivity and specificity of the test and expresses the magnitude, by which the odds ratios of a diagnosis in an individual is modified by the result of the test. For example, PLR expresses the power of a test to increase the odds ratio of the disease in a given individual; whereas, NLR expresses the power of a test to decrease the odds ratio of the disease in that individual. PLR ranges from one to +infinity and NLR ranges from zero to one. A test that is not clinically useful would have a PLR and NLR of one, meaning that the performance of the test would not help in diagnosis of a disease, as the result would not significantly change the pre-test odds ratio of a disease.

In general, when the PLR value for a test is above 10, the test is efficient in increasing the pre-test odds of the presence of a disease to an acceptable value for a clinician after a positive result. It means that the test would not detect any healthy individual as having the disease for which diagnosis is desired. In contrast, an NLR value of 0.2 or lower would significantly decrease the probability of the presence of a disease in healthy population. A clinician may find the PLR more important than NLR, since if a test has a high PLR, s/he could confidently label an individual as a patient in order to perform further intervention and be sure that s/he is not treating healthy individual. A test with high PLR could also reduce the number of individual in need for further diagnostic evaluation (which could be expensive and more invasive).

In the following, the PPV, NPV, PLR, and NLR for examples of diagnostic algorithms described in the present examples was examined. The values for sensitivity, specificity, PRV, NPV, PLR, and NLR are detailed in the table of FIG. 14. As it is calculated here, a positive result on E3 (E3>28; column 1) would indicate that an individual would have one of the PSC, PBC, or AIH with a high probability of 98% (PPV; column 4; rows 1-3). Similarly, a negative test result (E3<28) would indicate that an individual would not have any of the PSC, PBC, or AIH with the probability of 80%, 86%, or 100%, respectively (NPV; column 5; rows 1-3). Thus, after performing a measurement of E3 in serum of an individual that could be healthy or AIH case, a clinician could confidently conclude that if E3>28, a patient has AIH and if E3<28, there is no chance at all to have AIH.

Analysis of E3 concentration as a diagnostic for AIH (column 1; row 3), provided values of 50 for PLR (column 6; row 3) and zero for NLR (column 8; row 3). It means that the pre-test odds ratio for AIH multiplied by 50 for a positive test result (E3>28), and multiplied by zero for a negative test result (E3<28). To convert this to probability values to appreciate how performing of this test would increase the probability of AIH, a pre-test odds ratio of 1 to 1 (equal to a probability of 50%) was used as an example. After performing the test, for a positive test result (E3>28), the post-test odds ratio would increase to 50 to 1, which is equal to a probability of 98% (column 7; row 3). Similarly, for a negative test result (E3<28), the post-test odds ratio would decrease to zero to 1, which is equal to a probability value of 0% (column 9; row 3).

Other values in columns 7 and 9 are also showing the post-test probability values for other algorithms by a presumptuous pre-test odds ratio of 1 to 1 (equal to a pre-test probability value of 50%). In brief, it indicates that all of our diagnostic algorithms are able to increase a pre-test probability value of 50% to the values from 95% to 100% for a positive test result and decrease that to 0% to 29% for a negative test result. This analysis confirms the high magnitude of these diagnostic tests/algorithms to specifically detect patients rather than healthy individual (when positive results are observed; PLR). This would provide confidence for treating those that are labeled as patients and significantly reduce the number of individuals in need of further diagnostic evaluation that are sometimes invasive and expensive.

Example 5

Analysis of E3 and Alkaline Phosphatase (AP)

The measurement of the level of alkaline phosphatase (AP) in the serum is often included in the initial work-up panel for patients presenting with symptoms of liver diseases. AP levels are usually indicative of a cholestatic type of liver disease, although AP levels may not be consistently elevated throughout disease. Thus, detection of AP levels alone is usually insufficient to make a definitive diagnosis of disease such as PSC. As the level of E3 was shown to be significantly elevated in PSC patients as compared to chronic hepatitis C (CHC) patients and healthy controls (HCs), a study was conducted to determine if detection of E3 and AP might further facilitate diagnosis of PSC.

In this study, the level of total AP and E3 levels were measured in serum samples from patients having PSC. AP levels were assayed as total AP using an enzymatic assay for detection of AP enzymatic activity. Normal (control) ranges for AP were 40-129 IU/liter for men and 35-104 IU/liter for women. Patients having serum AP elevated above the normal level were denoted as AP positive (AP+). E3 was detected serum as described above. A serum E3 level above a control E3 level is referred to as E3 positive (E3+). The level of AP was measured in patients over four different office visits. The time between office visits varied from a few months to few years.

The results are show in FIG. 15. 55% of PSC patients were AP+ at all four time-points. 88% of PSC patients were AP+ for at least one of the four time points, with an average positivity of 70% for all four time-points (FIG. 15, lower panel).

In contrast, elevated E3 serum levels detected 79%, 84%, or 88% of PSC patients, if E3>28 pg/ml, E3>25 pg/ml, or E3>23 pg/ml, respectively. 97% of PSC patients had elevated E3 (E3>28 pg/ml) or had elevated AP at all four times points, and 98% of PSC patients had elevated E3 or elevated AP in at least one time-point (E3+ or any AP+) (FIG. 15, top and bottom panels). E3 has high specificity for PSC, with a false positive in CHC and HC cases of only 7% and 2%, respectively. This indicates that monitoring E3 levels and AP levels will facilitates diagnosis of PSC patients. This study is evidence of the value of including E3 in a liver panel along with AP as part of a routine set of markers to facilitate a diagnosis of, liver disease. Furthermore, where E3 is not part of an initial panel of markers in the course of diagnosis of a suspected liver disease, assessment of E3 levels with AP levels can identify patients having PSC who might otherwise escape accurate diagnosis using AP alone. Stated differently, in patients negative for AIH and negative for PBC, an E3 level greater than a control E3 level and/or an AP level greater than a control AP level is indicative of a diagnosis of PSC.

In summary, the measurement of E3 is able to differentiate PSC, PBC and AIH from healthy controls and HCV patients. Assaying for E3 in serum, as well as assaying for E1 serum concentration and using the E1/E3 ratio in addition with MDC serum levels is able to further differentiate PSC from PBC and/or AIH. By including IL-15 serum concentration as a parameter in addition to E3 level, E1/E3 ratio, and MDC level, PBC and AIH can be distinguished from each other. Finally, where a diagnosis of PSC is suspected, assaying of AP and E3 levels can increase the likelihood of making an accurate diagnosis of PSC in a subject.

Since the changes in the level of chemokines and cytokines normally precede the infiltration of leukocytes that cause damage to the liver, these diagnostics can facilitate early diagnosis, thus aiding in the treatment and management of patients. In addition, if viral hepatitis from known viruses is initially ruled out using available conventional diagnostics for viruses such the hepatitis A, B, C, D and E viruses plus EBV and CMV viruses, the differential diagnosis of PSC form PBC and AIH can be done by using the E1/E3 ratio in combination with the cutoff value for MDC followed by discrimination of PBC from AIH by adding IL-15 to the algorithm.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method detecting eotaxin-3 in a subject, the method comprising:
   obtaining a biological sample obtained from a subject suspected of having at least one of autoimmune hepatitis (AIH), primary sclerosing cholangitis (PSC), and primary biliary cirrhosis (PBC); and
   detecting eotaxin-3 (E3) in the biological sample by contacting the biological sample with an anti-E3 antibody and detecting binding between E3 and the antibody.

2. The method of claim 1, wherein the method comprises:
   detecting a level of eotaxin-1 (E1) in a biological sample of the subject by contacting the sample with an anti-E1 antibody and detecting binding between E1 and the antibody.

3. The method of claim 2, wherein the method comprises:
   detecting a level of macrophage-derived chemokine (MDC) in a biological sample of the subject by contacting the sample with an anti-MDC antibody and detecting binding between MDC and the antibody.

4. The method of claim 3, wherein the method comprises:
   detecting a level of interleukin-15 (IL-15) in a biological sample of the subject by contacting the sample with an anti-IL-15 antibody and detecting binding between IL-15 and the antibody.

5. The method of claim 1, wherein the method comprises:
   detecting a level of alkaline phosphatase (AP) in a biological sample of the subject by detecting AP enzymatic activity in the sample.

6. The method of claim 2, wherein the method comprises:
   calculating a ratio of E1 and E3 levels using the level of E1 and the level of E3; and
   detecting a level of macrophage-derived chemokine (MDC) in a biological sample from the subject by contacting the sample with an anti-MDC antibody and detecting binding between MDC and the antibody.

7. The method of claim 6, wherein the method comprises:
    detecting a level of interleukin-15 (IL-15) in a biological sample from the subject by contacting the sample with an anti-IL-15 antibody and detecting binding between IL-15 and the antibody.
8. The method of claim 1, wherein the subject is suspected of having PSC, and wherein the method comprises:
    detecting a level of alkaline phosphatase (AP) in a biological sample of the subject by detecting AP enzymatic activity in the sample.
9. The method of claim 1, wherein the biological sample is blood or blood product.
10. The method of claim 9, wherein the blood product is serum or plasma.
11. The method of claim 1, wherein the anti-E3 antibody is detectably labeled.
12. The method of claim 1, wherein the anti-E3-antibody is bound to a solid support.
13. The method of claim 2, wherein the anti-E1 antibody is detectably labeled.
14. The method of claim 2, wherein the anti-E1 antibody is bound to a solid support.
15. The method of claim 3, wherein the anti-MDC antibody is detectably labeled.
16. The method of claim 3, wherein the anti-MDC antibody is bound to a solid support.
17. The method of claim 4, wherein the anti-IL-15 antibody is detectably labeled.
18. The method of claim 4, wherein the anti-IL-15 antibody is bound to a solid support.
19. A method of detecting eotaxin-3 and alkaline phosphatase in a subject, the method comprising:
    obtaining a serum sample obtained from a subject suspected of having primary sclerosing cholangitis (PSC);
    assaying a level of eotaxin-3 (E3) in the serum sample by contacting the sample with an anti-PSC antibody and detecting binding between PSC and the antibody; and
    assaying a level of alkaline phosphatase (AP) in the serum sample by detecting AP enzymatic activity in the serum sample.
20. A method of detecting eotaxin-3, eotaxin-1 and macrophage-derived chemokine in a subject, the method comprising:
    obtaining a serum sample from a subject suspected of having at least one of autoimmune hepatitis (AIH), primary sclerosing cholangitis (PSC), and primary biliary cirrhosis (PBC);
    assaying a level of eotaxin-3 (E3) in the serum sample by contacting the serum sample with an anti-E3 antibody and detecting binding between E3 and the antibody;
    assaying a level of eotaxin-1 (E1) in the serum sample by contacting the serum sample with an anti-E1 antibody and detecting binding between E1 and the antibody; and
    assaying a level of macrophage-derived chemokine (MDC) in the serum sample by contacting the serum sample with an anti-MDC antibody and detecting binding between MDC and the antibody.
21. The method of claim 19, wherein the anti-E3 antibody is detectably labeled.
22. The method of claim 19, wherein the anti-E3 antibody is bound to a solid support.
23. The method of claim 20, wherein the anti-E3 antibody, anti-E1 antibody, and the anti-MDC antibody are detectably labeled.
24. The method of claim 20, wherein the anti-E3 antibody, anti-E1 antibody, and the anti-MDC antibody are bound to a solid support.
25. A method of detecting eotaxin-3, eotaxin-1, macrophage-derived chemokine, and interleukin-15 in a subject, the method comprising:
    obtaining a serum sample obtained from a subject suspected of having at least one of autoimmune hepatitis (AIH), primary sclerosing cholangitis (PSC), and primary biliary cirrhosis (PBC);
    assaying a level of eotaxin-3 (E3) in the serum sample by contacting the serum sample with an anti-E3 antibody and detecting binding between E3 and the antibody;
    assaying a level of eotaxin-1 (E1) in the serum sample by contacting the serum sample with an anti-E1 antibody and detecting binding between E1 and the antibody;
    assaying a level of macrophage-derived chemokine (MDC) in the serum sample by contacting the serum sample with an anti-MDC antibody and detecting binding between MDC and the antibody; and
    assaying a level of interleukin-15 (IL-15) in the serum sample by contacting the serum sample with an anti-IL-15 antibody and detecting binding between IL-15 and the antibody.
26. The method of claim 25, wherein the control E3 level is about 18 pg/ml-45 pg/ml serum.
27. The method of claim 25, wherein the anti-E3 antibody, anti-E1 antibody, the anti-MDC antibody, and the anti-IL-15 antibody are detectably labeled.
28. The method of claim 25, wherein the anti-E3 antibody, anti-E1 antibody, the anti-MDC antibody, and the anti-IL-15 antibody are bound to a solid support.
29. The method of claim 1, wherein the method comprises:
    inputting the E3 level, the E1 level, the MDC level, and/or IL-15 level into a computer programmed to execute an algorithm to perform the comparing and calculating step(s), wherein said inputting generates a result for a report.
30. The method of claim 29, wherein said generating a report is performed by the computer.
31. The method of claim 29, wherein the report is displayed to an output device at a location remote to the computer.

* * * * *